(12) United States Patent
Vernier et al.

(10) Patent No.: US 9,174,949 B2
(45) Date of Patent: Nov. 3, 2015

(54) HEDGEHOG INHIBITORS

(75) Inventors: Jean-Michel Vernier, San Diego, CA (US); John May, San Diego, CA (US); Patrick O'Connor, San Diego, CA (US); William Ripka, San Diego, CA (US); Anthony Pinkerton, San Diego, CA (US); Pierre-Yves Bounaud, San Diego, CA (US); Stephanie Hopkins, Poway, CA (US)

(73) Assignee: SELEXAGEN THERAPEUTICS, INC., San Diego, CA (US)

( * ) Notice: Subject to any disclaimer, the term of this patent is extended or adjusted under 35 U.S.C. 154(b) by 332 days.

(21) Appl. No.: 13/520,150

(22) PCT Filed: Jan. 6, 2011

(86) PCT No.: PCT/US2011/020416
§ 371 (c)(1),
(2), (4) Date: Sep. 24, 2012

(87) PCT Pub. No.: WO2011/085128
PCT Pub. Date: Jul. 14, 2011

(65) Prior Publication Data
US 2013/0012513 A1    Jan. 10, 2013

Related U.S. Application Data

(60) Provisional application No. 61/293,128, filed on Jan. 7, 2010.

(51) Int. Cl.
| | |
|---|---|
| *A61K 31/496* | (2006.01) |
| *A61K 31/5377* | (2006.01) |
| *A61K 31/427* | (2006.01) |
| *C07D 417/12* | (2006.01) |
| *C07D 277/22* | (2006.01) |
| *C07D 277/28* | (2006.01) |
| *C07D 263/32* | (2006.01) |
| *C07D 277/24* | (2006.01) |
| *C07D 277/30* | (2006.01) |

(52) U.S. Cl.
CPC ............ *C07D 277/28* (2013.01); *C07D 263/32* (2013.01); *C07D 277/24* (2013.01); *C07D 277/30* (2013.01)

(58) Field of Classification Search
CPC ............ A61K 31/496; A61K 31/5377; A61K 31/427; C07D 417/12; C07D 277/22
USPC ................... 514/366, 393; 548/150, 302.1
See application file for complete search history.

(56) References Cited

U.S. PATENT DOCUMENTS

| | | | |
|---|---|---|---|
| 6,552,016 B1 | 4/2003 | Baxter et al. | |
| 2001/0041814 A1* | 11/2001 | Tohnishi et al. | ............... 564/156 |
| 2006/0058302 A1 | 3/2006 | Duplantier et al. | |
| 2007/0105899 A1 | 5/2007 | Suzuki et al. | |
| 2009/0209573 A1 | 8/2009 | Wu et al. | |

FOREIGN PATENT DOCUMENTS

| | | |
|---|---|---|
| CA | 2658782 A1 | 1/2008 |
| EP | 1725544 B1 | 11/2006 |
| WO | WO-2006-028958 A2 | 3/2006 |
| WO | WO-2007-059157 A1 | 5/2007 |
| WO | WO-2009-027746 A1 | 3/2009 |
| WO | WO-2009-030952 A2 | 3/2009 |
| WO | WO-2009-146013 | 12/2009 |
| WO | WO 2009/151495 A2 | 12/2009 |
| WO | WO2010/127152 A2 | 11/2010 |
| WO | WO 2011/014888 | 2/2011 |
| WO | WO 2011/085128 | 7/2011 |
| WO | WO 2011/085261 | 7/2011 |

OTHER PUBLICATIONS

CN 201180005550.7 office action dated Jul. 30, 2014.
Database Caplus [Online] Chemical Abstracts Service, Columbus, Ohio, US; 2009,Goldfarb, David Scott: "Method of using lifespan-altering compounds for altering the lifespan of eukaryotic organisms and screening for such compounds", XP002698895. Database accession No. 2009:846104.
Database Registry [Online] Chemical Abstracts Service, Columbus, Ohio, US; 2005, XP002700134.
Database Registry [Online] Chemical Abstracts Service, Columbus, Ohio, US; 2009, XP002700135.
Database Registry [Online] Chemical Abstracts Service, Columbus, Ohio, US; 2009, XP002700136.
Database Registry [Online] Chemical Abstracts Service, Columbus, Ohio, US; 2005, XP002698897.
Database Registry [Online] Chemical Abstracts Service, Columbus, Ohio, US; Apr. 16, 2008, Database accession No. 1014831-09-4.
EP 11732162.0 Office action dated Jul. 8, 2014.
Chan, D.M.T. et al., "New N- and O-Arylations with Phenylboronic Acids and Cupric Acetate." Tetrahedron Letters, 1998, 39, 2933-2936.
Couve-Privat, et al. "Functional analysis of novel sonic hedgehog gene mutations identified in basal cell carcinomas from xeroderma pigmentosum patients." Cancer Research, 2004, 64, 3559-3565.
Cwik et al., "Suzuki-Miyaura cross-coupling reaction catalyzed by Pd/MgLa mixed oxide." Org. Biomol. Chem., 2005, 3, 4307-4309.
Dai, et al., "Thienopyrimidine ureas as novel and potent multitargeted receptor tyrosine kinase inhibitors." J. Med. Chem, 2005, 48, 6066.
Dwyer et al,, "Oxysterols are novel activators of the hedgehog signaling pathway in pluripotent mesenchymal cells." J. Biological Chemistry, 2007, 282, 8959-8968.

(Continued)

*Primary Examiner* — Sreeni Padmanabhan
*Assistant Examiner* — Sahar Javanmard
(74) *Attorney, Agent, or Firm* — Wilson, Sonsini, Goodrich & Rosati

(57) ABSTRACT

Described herein are compounds, pharmaceutical compositions and methods for the inhibition of Hedgehog signaling. Said compounds, pharmaceutical compositions and methods have utility in the treatment of human and veterinary disease and disorders.

17 Claims, 2 Drawing Sheets

(56) References Cited

OTHER PUBLICATIONS

Evans, D.A. et al., "Synthesis of Diaryl Ethers through the Copper-Promoted Arylation of Phenols with Arylboronic Acids. An Expedient Synthesis of Thyroxine." Tetrahendron Letters, 1998, 39,2937-2940.
Ishiyama, T., et al, "Palladium (0)-Catalyzed Cross-Coupling Reaction of Alkoxydiboron with Haloarenes: A Direct Procedure for Arylboronic Esters." J. Org. Chem., 1995, 60, 7508-7510.
Kulkarni, et al., "Chemotherapy of Tuberculosis, Part IX: Synthesis and Screening of New Thiazolyl Thiocarbanilides." Journal of Pharmaceutical Sciences (1969), 58(7), 852-7.
Kuwano, R. et al., "Suzuki-Miyaura Cross-Coupling of Benzylic Carbonates with Arylboronic Acids." Org. Lett., 2005,7, 945-947.
Lam, P.Y.S, et al., "New Aryl/Heteroaryl C-N Bond Cross-coupling Reactions via Arylboronic Acid/Cupric Acetate Arylation." Tetrahedron Letters, 1998, 39,2941-2944.
M. McLaughlin, "Suzuki-Miyaura Cross-Coupling of Benzylic Phosphates with Arylboronic Acids." Orig Lett, 2005, 7, 4875-4878.
Nilsson et al., "Base-Catalyzed Cyclization of N-Propargylamides to Oxazoles." Journal of Heterocyclic Chemistry (1989), 26(2), 269-75.
Pasca, et al., "Hedgehog signaling in Cancer Formation and Maintenance" Nature Reviews Cancer, Dec. 2003, vol. 3, pp. 903-911. p. 905, para 3.
PCT/US2010/044168 International Search Report dated Oct. 7, 2010.
PCT/US2011/020416 International Search Report dated Mar. 15, 2011.
PCT/US2011/020593 International Search Report dated Mar. 25, 2011.
Weissman, S.A. et al., "Ligand-free palladium-catalyzed cyanation of aryl halides." Org. Chem, 2005, 70, 1508-1510.
Wong, YC. et al., "Cobalt-catalyzed aryl-sulfur bond formation." Org. Lett., 2006, 8, 5613-5616.
Wu et al., "Purmorphamine induces osteogenesis by activation of the hedgehog signaling pathway." Chemistry & Biology, 2004, 11, 1229-1238.
JP Patent Application No. 2012-548127, Office Action dated Nov. 25, 2014.
Robarge et al., GDC-0449-A Potent inhibitor of the hedgehog pathway. Bioorganic & Medicinal Chemistry Letters, 19:5576-5581 (2009).
AU2011204370 patent examination report dated May 16, 2013.
Brown, et al. Discovery of amide replacements that improve activity and metabolic stability of a bis-amide smoothened antagonist hit. Bioorg Med Chem Lett. Sep. 15, 2011;21(18):5206-5209.
CA 2,785,204 office action dated Jun. 3, 2013.
CA 2,785,204 office action dated Apr. 10, 2014.
CN 201180005550.7 office action dated Jul. 12, 2013.
CN 201180005550.7 office action dated Feb. 21, 2014.
Douard et al, Surgery 136, 665-670 (2006).
EP 11732162.0 Extended European search report dated Jul. 24, 2013.
Huang et al Carcinogenesis 27, 1334-1340 (2006).
Ma et al, Carcinogenesis 26, 1698-1705 (2005).
Sanchez et al, PNAS 101, 12561-12566 (2004).
Thayer et al, Nature 425, 851-855. (2003).
TH 1201003201 Office action dated Sep. 12, 2013.
Watkins et al, Nature 422, 313-317 (2003).
XP002698894 Chemical Abstracts Service accession No. 1982:471688, 1981.
XP002698895 Chemical Abstracts Service accession No. 2009:846104, 2009.
XP002698896 Chemical Abstracts Service accession No. 1325508-40-4, 2011.
XP002698897 Chemical Abstracts Service accession No. 832688-06-9, 2005.
XP002700133 Chemical Abstracts Service accession No. 1100228-91-8, 2009.
XP002700134 Chemical Abstracts Service accession No. 694460-58-7, 2004.
XP002700135 Chemical Abstracts Service accession No. 1030204-60-4, 2008.
XP002700136 Chemical Abstracts Service accession No. 1036693-42-1, 2008.

* cited by examiner

HEDGEHOG INHIBITORS

CROSS REFERENCE

This application is filed pursuant to 35 U.S.C. §371 as a United States National Phase Application of International Application No. PCT/US2011/020416, filed on Jan. 6, 2011, which claims the benefit of U.S. Provisional Application No. 61/293,128, filed Jan. 7, 2010 which is incorporated herein by reference in its entirety.

BACKGROUND OF THE INVENTION

Described herein are compounds, pharmaceutical compositions and methods for the inhibition of Hedgehog signaling. Said compounds, pharmaceutical compositions and methods have utility in the treatment of human and veterinary disease and disorders.

SUMMARY OF THE INVENTION

One embodiment provides a compound having the structure of Formula (I):

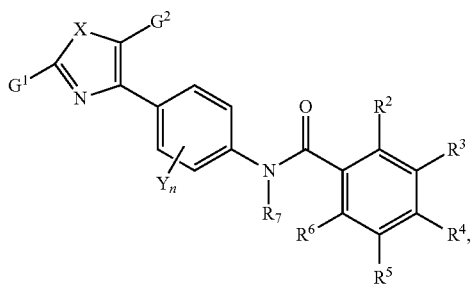

(I)

or a stereoisomer, tautomer, hydrate, solvate or pharmaceutically acceptable salt thereof, wherein:
X is —S—, —O—, —N(H)— or —N($R^1$)—;
Y is halogen, $C_1$-$C_3$ alkyl, —CN, or —$CF_3$;
n is 0, 1, 2 or 3;
$G^1$ is hydrogen, halogen, $C_1$-$C_6$ alkyl, $C_3$-$C_6$ cycloalkyl, —CN, —$CF_3$, or aryl;
$G^2$ is hydrogen, halogen, $C_1$-$C_3$ alkyl, —CN, or —$CF_3$;
$R^1$ is H or $C_1$-$C_3$ alkyl;
$R^2$ is selected from hydrogen, halogen, —CN, alkyl, —$CF_3$, aryl, —O-alkyl, —O-aryl, —O-heteroaryl, —$CH_2$-aryl, —$CH_2$-heteroaryl, —NH-aryl, —$SO_2$-aryl, $SO_2$-alkyl-NH-heteroaryl, —NH-alkyl, —$CH_2$—NH-alkyl, —$CH_2$—N(alkyl)$_2$, —$CH_2$—(N-linked heterocycle), —$CH_2$—(C-linked heterocycle), N-linked heterocycle, and C-linked heterocycle;
$R^4$ is selected from hydrogen, halogen, alkyl, alkoxy, —CN, —$CF_3$, —$SO_2$-alkyl, —$SO_2NH_2$, —$NHSO_2$-alkyl, —$NHSO_2$-aryl, —NHCO-alkyl, —NHCO-aryl, —NHCONH-alkyl, —NHCONH-aryl, —$CONH_2$, —CONH-alkyl, —CONH-aryl, —CON(alkyl)$_2$, —CON(aryl)$_2$, —$CO_2H$, and —$CO_2$alkyl;
$R^3$, $R^5$ and $R^6$ are each independently selected from hydrogen, halogen, —CN, alkyl, aryl, heteroaryl, C-linked heterocycle, —O-alkyl, —O-aryl, —O-heteroaryl, N-linked heterocycle, —NH-alkyl, —N(alkyl)$_2$, —NH-aryl, —NHheteroaryl, —$CO_2H$, —$CO_2$alkyl, —$SO_2$alkyl, —$SO_2NH_2$, —$SO_2$NHalkyl, —$SO_2$N(alkyl)$_2$, —$NHSO_2$alkyl, —$NHSO_2$aryl, —NHCONH-alkyl, —NHCON(alkyl)$_2$, —N(alkyl)CONH$_2$, —N(alkyl)CONH(alkyl), and —N(alkyl)CON(alkyl)$_2$; and
$R^7$ is H or $C_1$-$C_3$ alkyl.

Another embodiment provides a compound having the structure of Formula (I) wherein X is —S—, —O—.

Another embodiment provides a compound having the structure of Formula (I) wherein $G^1$ and $G^2$ can not both be hydrogen.

Another embodiment provides a compound having the structure of Formula (I) wherein:
X is —S—, —O—, —N(H)— or —N($R^1$)—;
Y is halogen, $C_1$-$C_3$ alkyl, —CN, or —$CF_3$;
n is 0, 1, 2 or 3;
$G^1$ is hydrogen, halogen, $C_1$-$C_3$ alkyl, —CN, or —$CF_3$;
$G^2$ is hydrogen, halogen, $C_1$-$C_3$ alkyl, —CN, or —$CF_3$, and wherein $G^1$ and $G^2$ can not both be hydrogen;
$R^1$ is H or $C_1$-$C_3$ alkyl;
$R^2$ is selected from halogen, —CN, alkyl, aryl, —O-aryl, —O-heteroaryl, —$CH_2$-aryl, —$CH_2$-heteroaryl, —NH-aryl, —$SO_2$-aryl, —NH-heteroaryl, —NH-alkyl, —$CH_2$—NH-alkyl, —$CH_2$—N(alkyl)$_2$, —$CH_2$—(N-linked heterocycle), —$CH_2$—(C-linked heterocycle), N-linked heterocycle, and C-linked heterocycle;
$R^4$ is selected from alkoxy, —CN, —$SO_2$-alkyl, —$SO_2NH_2$, —$NHSO_2$-alkyl, —$NHSO_2$-aryl, —NHCO-alkyl, —NHCO-aryl, —NHCONH-alkyl, —NHCONH-aryl, —$CONH_2$, —CONH-alkyl, —CONH-aryl, —CON(alkyl)$_2$, —CON(aryl)$_2$, —$CO_2H$, and —$CO_2$alkyl; and
$R^3$, $R^5$ and $R^6$ are each independently selected from hydrogen, halogen, —CN, alkyl, aryl, heteroaryl, C-linked heterocycle, —O-alkyl, —O-aryl, —O-heteroaryl, N-linked heterocycle, —NH-alkyl, —N(alkyl)$_2$, —NH-aryl, —NHheteroaryl, —$CO_2H$, —$CO_2$alkyl, —$SO_2$alkyl, —$SO_2NH_2$, —$SO_2$NHalkyl, —$SO_2$N(alkyl)$_2$, —$NHSO_2$alkyl, —$NHSO_2$aryl, —NHCONH-alkyl, —NHCON(alkyl)$_2$, —N(alkyl)CONH$_2$, —N(alkyl)CONH(alkyl), and —N(alkyl)CON(alkyl)$_2$.

Another embodiment provides a compound having the structure of Formula (I) wherein n is 0.

Another embodiment provides a compound having the structure of Formula (I) wherein n is 1.

Another embodiment provides a compound having the structure of Formula (I) wherein $G^2$ is H.

Another embodiment provides a compound having the structure of Formula (I) wherein $G^2$ is H and $G^1$ is alkyl.

Another embodiment provides a compound having the structure of Formula (I) wherein X is —S—.

Another embodiment provides a compound having the structure of Formula (I) wherein $R^2$ is —$CH_2$—NH-alkyl, —$CH_2$—N(alkyl)$_2$, —$CH_2$—(N-linked heterocycle), or —$CH_2$—(C-linked heterocycle).

Another embodiment provides a compound having the structure of Formula (I) wherein $R^2$ is halogen, —CN, -alkyl, or —$CF_3$.

Another embodiment provides a compound having the structure of Formula (I) wherein $R^4$ is —$SO_2$Me or —OMe.

Another embodiment provides a compound having the structure of Formula (I) wherein $R^2$ is halogen and $R^4$ is —$SO_2$Me.

Another embodiment provides a compound having the structure of Formula (I) wherein $R^2$ is halogen and $R^4$ is —OMe.

Another embodiment provides a compound having the structure of Formula (I) wherein n is 0; $G^2$ is H; $G^1$ is alkyl; X is —S—; $R^2$ is halogen and $R^4$ is —OMe.

Another embodiment provides a compound having the structure of Formula (I) wherein n is 0; $G^2$ is H; $G^1$ is alkyl; X is —S—; $R^2$ is halogen and $R^4$ is —$SO_2$Me.

One embodiment provides a pharmaceutical composition comprising a compound of Formula (I), or a stereoisomer, hydrate, solvate or pharmaceutically acceptable salt thereof, and at least one pharmaceutically acceptable excipient, wherein the compound of Formula (I) has the following structure:

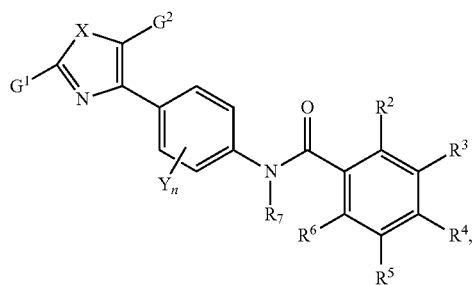

(I)

or a stereoisomer, tautomer, hydrate, solvate or pharmaceutically acceptable salt thereof, wherein:

X is —S—, —O—, —N(H)— or —N($R^1$)—;

Y is halogen, $C_1$-$C_3$ alkyl, —CN, or —$CF_3$;

n is 0, 1, 2 or 3;

$G^1$ is hydrogen, halogen, $C_1$-$C_6$ alkyl, $C_3$-$C_6$ cycloalkyl, —CN, —$CF_3$, or aryl;

$G^2$ is hydrogen, halogen, $C_1$-$C_3$ alkyl, —CN, or —$CF_3$;

$R^1$ is H or $C_1$-$C_3$ alkyl;

$R^2$ is selected from hydrogen, halogen, —CN, alkyl, —$CF_3$, aryl, —O-alkyl, —O-aryl, —O-heteroaryl, —$CH_2$-aryl, —$CH_2$-heteroaryl, —NH-aryl, —$SO_2$-aryl, $SO_2$-alkyl-NH-heteroaryl, —NH-alkyl, —$CH_2$—NH-alkyl, —$CH_2$—N(alkyl)$_2$, —$CH_2$—(N-linked heterocycle), —$CH_2$—(C-linked heterocycle), N-linked heterocycle, and C-linked heterocycle;

$R^4$ is selected from hydrogen, halogen, alkyl, alkoxy, —CN, —$CF_3$, —$SO_2$-alkyl, —$SO_2NH_2$, —$NHSO_2$-alkyl, —$NHSO_2$-aryl, —NHCO-alkyl, —NHCO-aryl, —NHCONH-alkyl, —NHCONH-aryl, —$CONH_2$, —CONH-alkyl, —CONH-aryl, —CON(alkyl)$_2$, —CON(aryl)$_2$, —$CO_2$H, and —$CO_2$alkyl;

$R^3$, $R^5$ and $R^6$ are each independently selected from hydrogen, halogen, —CN, alkyl, aryl, heteroaryl, C-linked heterocycle, —O-alkyl, —O-aryl, —O-heteroaryl, linked heterocycle, —NH-alkyl, —N(alkyl)$_2$, —NH-aryl, —NHheteroaryl, —$CO_2$H, —$CO_2$alkyl, —$SO_2$alkyl, —$SO_2NH_2$, —$SO_2$NHalkyl, —$SO_2$N(alkyl)$_2$, —$NHSO_2$alkyl, —$NHSO_2$aryl, —NHCONH-alkyl, —NHCON(alkyl)$_2$, —N(alkyl)$CONH_2$, —N(alkyl)CONH(alkyl), and —N(alkyl)CON(alkyl)$_2$; and $R^7$ is H or $C_1$-$C_3$ alkyl.

One embodiment provides a method of inhibiting the Hedgehog pathway in a cell comprising contacting the cell with an inhibitory concentration of a compound of Formula (I):

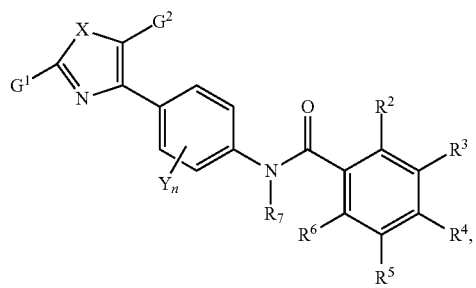

(I)

or a stereoisomer, tautomer, hydrate, solvate or pharmaceutically acceptable salt thereof, wherein:

X is —S—, —O—, —N(H)— or —N($R^1$)—;

Y is halogen, $C_1$-$C_3$ alkyl, —CN, or —$CF_3$;

n is 0, 1, 2 or 3;

$G^1$ is hydrogen, halogen, $C_1$-$C_6$ alkyl, $C_3$-$C_6$ cycloalkyl, —CN, —$CF_3$, or aryl;

$G^2$ is hydrogen, halogen, $C_1$-$C_3$ alkyl, —CN, or —$CF_3$;

$R^1$ is H or $C_1$-$C_3$ alkyl;

$R^2$ is selected from hydrogen, halogen, —CN, alkyl, —$CF_3$, aryl, —O-alkyl, —O-aryl, —O-heteroaryl, —$CH_2$-aryl, —$CH_2$-heteroaryl, —NH-aryl, —$SO_2$-aryl, $SO_2$-alkyl-NH-heteroaryl, —NH-alkyl, —$CH_2$—NH-alkyl, —$CH_2$—N(alkyl)$_2$, —$CH_2$—(N-linked heterocycle), —$CH_2$—(C-linked heterocycle), N-linked heterocycle, and C-linked heterocycle;

$R^4$ is selected from hydrogen, halogen, alkyl, alkoxy, —CN, —$CF_3$, —$SO_2$-alkyl, —$SO_2NH_2$, —$NHSO_2$-alkyl, —$NHSO_2$-aryl, —NHCO-alkyl, —NHCO-aryl, —NHCONH-alkyl, —NHCONH-aryl, —$CONH_2$, —CONH-alkyl, —CONH-aryl, —CON(alkyl)$_2$, —CON(aryl)$_2$, —$CO_2$H, and —$CO_2$alkyl;

$R^3$, $R^5$ and $R^6$ are each independently selected from hydrogen, halogen, —CN, alkyl, aryl, heteroaryl, C-linked heterocycle, —O-alkyl, —O-aryl, —O-heteroaryl, N-linked heterocycle, —NH-alkyl, —N(alkyl)$_2$, —NH-aryl, —NHheteroaryl, —$CO_2$H, —$CO_2$alkyl, —$SO_2$alkyl, —$SO_2NH_2$, —$SO_2$NHalkyl, —$SO_2$N(alkyl)$_2$, —$NHSO_2$alkyl, —$NHSO_2$aryl, —NHCONH-alkyl, —NHCON(alkyl)$_2$, —N(alkyl)$CONH_2$, —N(alkyl)CONH(alkyl), and —N(alkyl)CON(alkyl)$_2$; and $R^7$ is H or $C_1$-$C_3$ alkyl.

Another embodiment provides the method wherein the cell is characterized by a patched loss-of-function phenotype. Another embodiment provides the method wherein the cell is characterized by a smoothened gain-of-function phenotype. Another embodiment provides the method wherein the cell is characterized by a constitutively active smoothened phenotype. Another embodiment provides the method wherein the cell is characterized by expression of Gli.

One embodiment provides a method of inhibiting the activity of smoothened protein in a cell comprising contacting the smoothened protein with an inhibitory concentration of a compound of Formula (I):

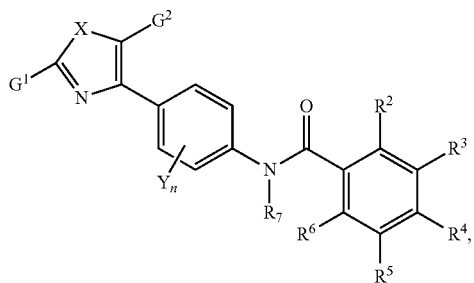

(I)

or a stereoisomer, tautomer, hydrate, solvate or pharmaceutically acceptable salt thereof, wherein:

X is —S—, —O—, —N(H)— or —N($R^1$)—;
Y is halogen, $C_1$-$C_3$ alkyl, —CN, or —$CF_3$;
n is 0, 1, 2 or 3;
$G^1$ is hydrogen, halogen, $C_1$-$C_6$ alkyl, $C_3$-$C_6$ cycloalkyl, —CN, —$CF_3$, or aryl;
$G^2$ is hydrogen, halogen, $C_1$-$C_3$ alkyl, —CN, or —$CF_3$;
$R^1$ is H or $C_1$-$C_3$ alkyl;
$R^2$ is selected from hydrogen, halogen, —CN, alkyl, —$CF_3$, aryl, —O-alkyl, —O-aryl, —O-heteroaryl, —$CH_2$-aryl, —$CH_2$-heteroaryl, —NH-aryl, —$SO_2$-aryl, $SO_2$-alkyl-NH-heteroaryl, —NH-alkyl, —$CH_2$—NH-alkyl, —$CH_2$—N(alkyl)$_2$, —$CH_2$—(N-linked heterocycle), —$CH_2$—(C-linked heterocycle), N-linked heterocycle, and C-linked heterocycle;
$R^4$ is selected from hydrogen, halogen, alkyl, alkoxy, —CN, —$CF_3$, —$SO_2$-alkyl, —$SO_2NH_2$, —$NHSO_2$-alkyl, —$NHSO_2$-aryl, —NHCO-alkyl, —NHCO-aryl, —NHCONH-alkyl, —NHCONH-aryl, —$CONH_2$, —CONH-alkyl, —CONH-aryl, —CON(alkyl)$_2$, —CON(aryl)$_2$, —$CO_2H$, and —$CO_2$alkyl;
$R^3$, $R^5$ and $R^6$ are each independently selected from hydrogen, halogen, —CN, alkyl, aryl, heteroaryl, C-linked heterocycle, —O-alkyl, —O-aryl, —O-heteroaryl, N-linked heterocycle, —NH-alkyl, —N(alkyl)$_2$, —NH-aryl, —NHheteroaryl, —$CO_2H$, —$CO_2$alkyl, —$SO_2$alkyl, —$SO_2NH_2$, —$SO_2$NHalkyl, —$SO_2$N(alkyl)$_2$, —$NHSO_2$alkyl, —$NHSO_2$aryl, —NHCONH-alkyl, —NHCON(alkyl)$_2$, —N(alkyl)CONH$_2$, —N(alkyl)CONH(alkyl), and —N(alkyl)CON(alkyl)$_2$; and
$R^7$ is H or $C_1$-$C_3$ alkyl.

Another embodiment provides the method wherein the cell is characterized by a patched loss-of-function phenotype. Another embodiment provides the method wherein the cell is characterized by a smoothened gain-of-function phenotype. Another embodiment provides the method wherein the cell is characterized by a constitutively active smoothened phenotype. Another embodiment provides the method wherein the cell is characterized by expression of Gli.

One embodiment provides a method of inhibiting the transcriptional activity of Gli transcription factor in a cell comprising contacting the cell with an inhibitory concentration of a compound of Formula (I):

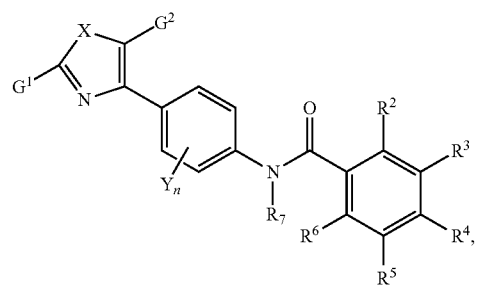

(I)

or a stereoisomer, tautomer, hydrate, solvate or pharmaceutically acceptable salt thereof, wherein:

X is —S—, —O—, —N(H)— or —N($R^1$)—;
Y is halogen, $C_1$-$C_3$ alkyl, —CN, or —$CF_3$;
n is 0, 1, 2 or 3;
$G^1$ is hydrogen, halogen, $C_1$-$C_6$ alkyl, $C_3$-$C_6$ cycloalkyl, —CN, —$CF_3$, or aryl;
$G^2$ is hydrogen, halogen, $C_1$-$C_3$ alkyl, —CN, or —$CF_3$;
$R^1$ is H or $C_1$-$C_3$ alkyl;
$R^2$ is selected from hydrogen, halogen, —CN, alkyl, —$CF_3$, aryl, —O-alkyl, —O-aryl, —O-heteroaryl, —$CH_2$-aryl, —$CH_2$-heteroaryl, —NH-aryl, —$SO_2$-aryl, $SO_2$-alkyl-NH-heteroaryl, —NH-alkyl, —$CH_2$—NH-alkyl, —$CH_2$—N(alkyl)$_2$, —$CH_2$—(N-linked heterocycle), —$CH_2$—(C-linked heterocycle), N-linked heterocycle, and C-linked heterocycle;
$R^4$ is selected from hydrogen, halogen, alkyl, alkoxy, —CN, —$CF_3$, —$SO_2$-alkyl, —$SO_2NH_2$, —$NHSO_2$-alkyl, —$NHSO_2$-aryl, —NHCO-alkyl, —NHCO-aryl, —NHCONH-alkyl, —NHCONH-aryl, —$CONH_2$, —CONH-alkyl, —CONH-aryl, —CON(alkyl)$_2$, —CON(aryl)$_2$, —$CO_2H$, and —$CO_2$alkyl;
$R^3$, $R^5$ and $R^6$ are each independently selected from hydrogen, halogen, —CN, alkyl, aryl, heteroaryl, C-linked heterocycle, —O-alkyl, —O-aryl, —O-heteroaryl, N-linked heterocycle, —NH-alkyl, —N(alkyl)$_2$, —NH-aryl, —NHheteroaryl, —$CO_2H$, —$CO_2$alkyl, —$SO_2$alkyl, —$SO_2NH_2$, —$SO_2$NHalkyl, —$SO_2$N(alkyl)$_2$, —$NHSO_2$alkyl, —$NHSO_2$aryl, —NHCONH-alkyl, —NHCON(alkyl)$_2$, —N(alkyl)CONH$_2$, —N(alkyl)CONH(alkyl), and —N(alkyl)CON(alkyl)$_2$; and
$R^7$ is H or $C_1$-$C_3$ alkyl.

Another embodiment provides the method wherein the cell is characterized by a patched loss-of-function phenotype. Another embodiment provides the method wherein the cell is characterized by a smoothened gain-of-function phenotype. Another embodiment provides the method wherein the cell is characterized by a constitutively active smoothened phenotype. Another embodiment provides the method wherein the cell is characterized by expression of Gli.

One embodiment provides a method of inhibiting Gli-mediated gene transcription in a cell comprising contacting the cell with an inhibitory concentration of a compound of Formula (I):

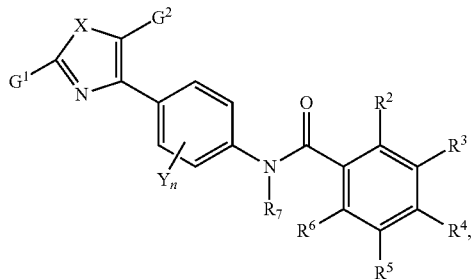
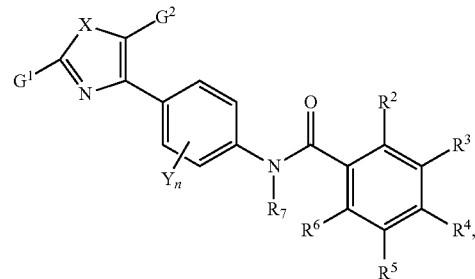

or a stereoisomer, tautomer, hydrate, solvate or pharmaceutically acceptable salt thereof, wherein:

X is —S—, —O—, —N(H)— or —N($R^1$)—;

Y is halogen, $C_1$-$C_3$ alkyl, —CN, or —$CF_3$;

n is 0, 1, 2 or 3;

$G^1$ is hydrogen, halogen, $C_1$-$C_6$ alkyl, $C_3$-$C_6$ cycloalkyl, —CN, —$CF_3$, or aryl;

$G^2$ is hydrogen, halogen, $C_1$-$C_3$ alkyl, —CN, or —$CF_3$;

$R^1$ is H or $C_1$-$C_3$ alkyl;

$R^2$ is selected from hydrogen, halogen, —CN, alkyl, —$CF_3$, aryl, —O-alkyl, —O-aryl, —O-heteroaryl, —$CH_2$-aryl, —$CH_2$-heteroaryl, —NH-aryl, —$SO_2$-aryl, $SO_2$-alkyl-NH-heteroaryl, —NH-alkyl, —$CH_2$—NH-alkyl, —$CH_2$—N(alkyl)$_2$, —$CH_2$—(N-linked heterocycle), —$CH_2$—(C-linked heterocycle), N-linked heterocycle, and C-linked heterocycle;

$R^4$ is selected from hydrogen, halogen, alkyl, alkoxy, —CN, —$CF_3$, —$SO_2$-alkyl, —$SO_2NH_2$, —$NHSO_2$-alkyl, —$NHSO_2$-aryl, —NHCO-alkyl, —NHCO-aryl, —NHCONH-alkyl, —NHCONH-aryl, —$CONH_2$, —CONH-alkyl, —CONH-aryl, —CON(alkyl)$_2$, —CON(aryl)$_2$, —$CO_2$H, and —$CO_2$alkyl;

$R^3$, $R^5$ and $R^6$ are each independently selected from hydrogen, halogen, —CN, alkyl, aryl, heteroaryl, C-linked heterocycle, —O-alkyl, —O-aryl, —O-heteroaryl, linked heterocycle, —NH-alkyl, —N(alkyl)$_2$, —NH-aryl, —NHheteroaryl, —$CO_2$H, —$CO_2$alkyl, —$SO_2$alkyl, —$SO_2NH_2$, —$SO_2$NHalkyl, —$SO_2$N(alkyl)$_2$, —$NHSO_2$alkyl, —$NHSO_2$aryl, —NHCONH-alkyl, —NHCON(alkyl)$_2$, —N(alkyl)$CONH_2$, —N(alkyl)CONH(alkyl), and —N(alkyl)CON(alkyl)$_2$; and $R^7$ is H or $C_1$-$C_3$ alkyl.

Another embodiment provides the method wherein the cell is characterized by a patched loss-of-function phenotype. Another embodiment provides the method wherein the cell is characterized by a smoothened gain-of-function phenotype. Another embodiment provides the method wherein the cell is characterized by a constitutively active smoothened phenotype. Another embodiment provides the method wherein the cell is characterized by expression of Gli.

One embodiment provides a method of treating a human disease or disorder mediated by Hedgehog pathway comprising administering to a patient a therapeutically effective amount of a composition comprising a compound of Formula (I), or a stereoisomer, tautomer, hydrate, solvate or pharmaceutically acceptable salt thereof, wherein the compound of Formula (I) has the following structure:

or a stereoisomer, tautomer, hydrate, solvate or pharmaceutically acceptable salt thereof, wherein:

X is —S—, —O—, —N(H)— or —N($R^1$)—;

Y is halogen, $C_1$-$C_3$ alkyl, —CN, or —$CF_3$;

n is 0, 1, 2 or 3;

$G^1$ is hydrogen, halogen, $C_1$-$C_6$ alkyl, $C_3$-$C_6$ cycloalkyl, —CN, —$CF_3$, or aryl;

$G^2$ is hydrogen, halogen, $C_1$-$C_3$ alkyl, —CN, or —$CF_3$;

$R^1$ is H or $C_1$-$C_3$ alkyl;

$R^2$ is selected from hydrogen, halogen, —CN, alkyl, —$CF_3$, aryl, —O-alkyl, —O-aryl, —O-heteroaryl, —$CH_2$-aryl, —$CH_2$-heteroaryl, —NH-aryl, —$SO_2$-aryl, $SO_2$-alkyl —NH-heteroaryl, —NH-alkyl, —$CH_2$—NH-alkyl, —$CH_2$—N(alkyl)$_2$, —$CH_2$—(N-linked heterocycle), —$CH_2$—(C-linked heterocycle), N-linked heterocycle, and C-linked heterocycle;

$R^4$ is selected from hydrogen, halogen, alkyl, alkoxy, —CN, —$CF_3$, —$SO_2$-alkyl, —$SO_2NH_2$, —$NHSO_2$-alkyl, —$NHSO_2$-aryl, —NHCO-alkyl, —NHCO-aryl, —NHCONH-alkyl, —NHCONH-aryl, —$CONH_2$, —CONH-alkyl, —CONH-aryl, —CON(alkyl)$_2$, —CON(aryl)$_2$, —$CO_2$H, and —$CO_2$alkyl;

$R^3$, $R^5$ and $R^6$ are each independently selected from hydrogen, halogen, —CN, alkyl, aryl, heteroaryl, C-linked heterocycle, —O-alkyl, —O-aryl, —O-heteroaryl, N-linked heterocycle, —NH-alkyl, —N(alkyl)$_2$, —NH-aryl, —NHheteroaryl, —$CO_2$H, —$CO_2$alkyl, —$SO_2$alkyl, —$SO_2NH_2$, —$SO_2$NHalkyl, —$SO_2$N(alkyl)$_2$, —$NHSO_2$alkyl, —$NHSO_2$aryl, —NHCONH-alkyl, —NHCON(alkyl)$_2$, —N(alkyl)$CONH_2$, —N(alkyl)CONH(alkyl), and —N(alkyl)CON(alkyl)$_2$; and $R^7$ is H or $C_1$-$C_3$ alkyl.

Another embodiment provides the method wherein the disease or disorder is a proliferative disease. Another embodiment provides the method wherein the proliferative disease is selected from colon cancer, lung cancer, pancreatic cancer, gastric cancer, prostate cancer, and hepatocellular carcinoma. Another embodiment provides the method wherein the proliferative disease is selected from basal cell carcinoma, breast cancer, bone sarcoma, soft tissue sarcoma, chronic myeloid leukemia, acute myeloid leukemia, hematological cancer, medulloblastoma, rhabdomyosaracoma, neuroblastoma, pancreatic cancer, breast carcinoma, meningioma, glioblastoma, astrocytoma, melanoma, stomach cancer, esophageal cancer, biliary tract cancer, prostate cancer, small cell lung cancer, non-small cell lung cancer, glial cell cancer, multiple myeloma, colon cancer, neuroectodermal tumor, neuroendocrine tumor, mastocytoma and Gorlin syndrome. Another embodiment provides the method wherein the proliferative disease is basal cell carcinoma.

One embodiment provides a method of treating a veterinary disease or disorder mediated by Hedgehog pathway comprising administering to a subject a therapeutically effective amount of a composition comprising a compound of Formula (I), or a stereoisomer, tautomer, hydrate, solvate or pharmaceutically acceptable salt thereof, wherein the compound of Formula (I) has the following structure:

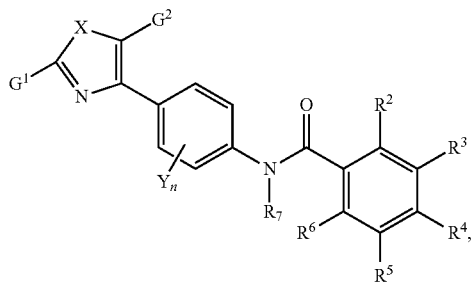

(I)

or a stereoisomer, tautomer, hydrate, solvate or pharmaceutically acceptable salt thereof, wherein:
X is —S—, —O—, —N(H)— or —N($R^1$)—;
Y is halogen, $C_1$-$C_3$ alkyl, —CN, or —$CF_3$;
n is 0, 1, 2 or 3;
$G^1$ is hydrogen, halogen, $C_1$-$C_6$ alkyl, $C_3$-$C_6$ cycloalkyl, —CN, —$CF_3$, or aryl;
$G^2$ is hydrogen, halogen, $C_1$-$C_3$ alkyl, —CN, or —$CF_3$;
$R^1$ is H or $C_1$-$C_3$ alkyl;
$R^2$ is selected from hydrogen, halogen, —CN, alkyl, —$CF_3$, aryl, —O-alkyl, —O-aryl, —O-heteroaryl, —$CH_2$-aryl, —$CH_2$-heteroaryl, —NH-aryl, —$SO_2$-aryl, $SO_2$-alkyl-NH-heteroaryl, —NH-alkyl, —$CH_2$—NH-alkyl, —$CH_2$—N(alkyl)$_2$, —$CH_2$—(N-linked heterocycle), —$CH_2$—(C-linked heterocycle), N-linked heterocycle, and C-linked heterocycle;
$R^4$ is selected from hydrogen, halogen, alkyl, alkoxy, —CN, —$CF_3$, —$SO_2$-alkyl, —$SO_2NH_2$, —$NHSO_2$-alkyl, —$NHSO_2$-aryl, —NHCO-alkyl, —NHCO-aryl, —NHCONH-alkyl, —NHCONH-aryl, —$CONH_2$, —CONH-alkyl, —CONH-aryl, —CON(alkyl)$_2$, —CON(aryl)$_2$, —$CO_2$H, and —$CO_2$alkyl;
$R^3$, $R^5$ and $R^6$ are each independently selected from hydrogen, halogen, —CN, alkyl, aryl, heteroaryl, C-linked heterocycle, —O-alkyl, —O-aryl, —O-heteroaryl, N-linked heterocycle, —NH-alkyl, —N(alkyl)$_2$, —NH-aryl, —NHheteroaryl, —$CO_2$H, —$CO_2$alkyl, —$SO_2$alkyl, —$SO_2NH_2$, —$SO_2$NHalkyl, —$SO_2$N(alkyl)$_2$, —$NHSO_2$alkyl, —$NHSO_2$aryl, —NHCONH-alkyl, —NHCON(alkyl)$_2$, —N(alkyl)CONH$_2$, —N(alkyl)CONH(alkyl), and —N(alkyl)CON(alkyl)$_2$; and
$R^7$ is H or $C_1$-$C_3$ alkyl.

Another embodiment provides a method of treating a veterinary disease or disorder wherein the disease or disorder is a proliferative disease selected from mast cell tumors or osteosarcoma.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Heterocyclic Benzamide Hedgehog Inhibitors

Figure 1:
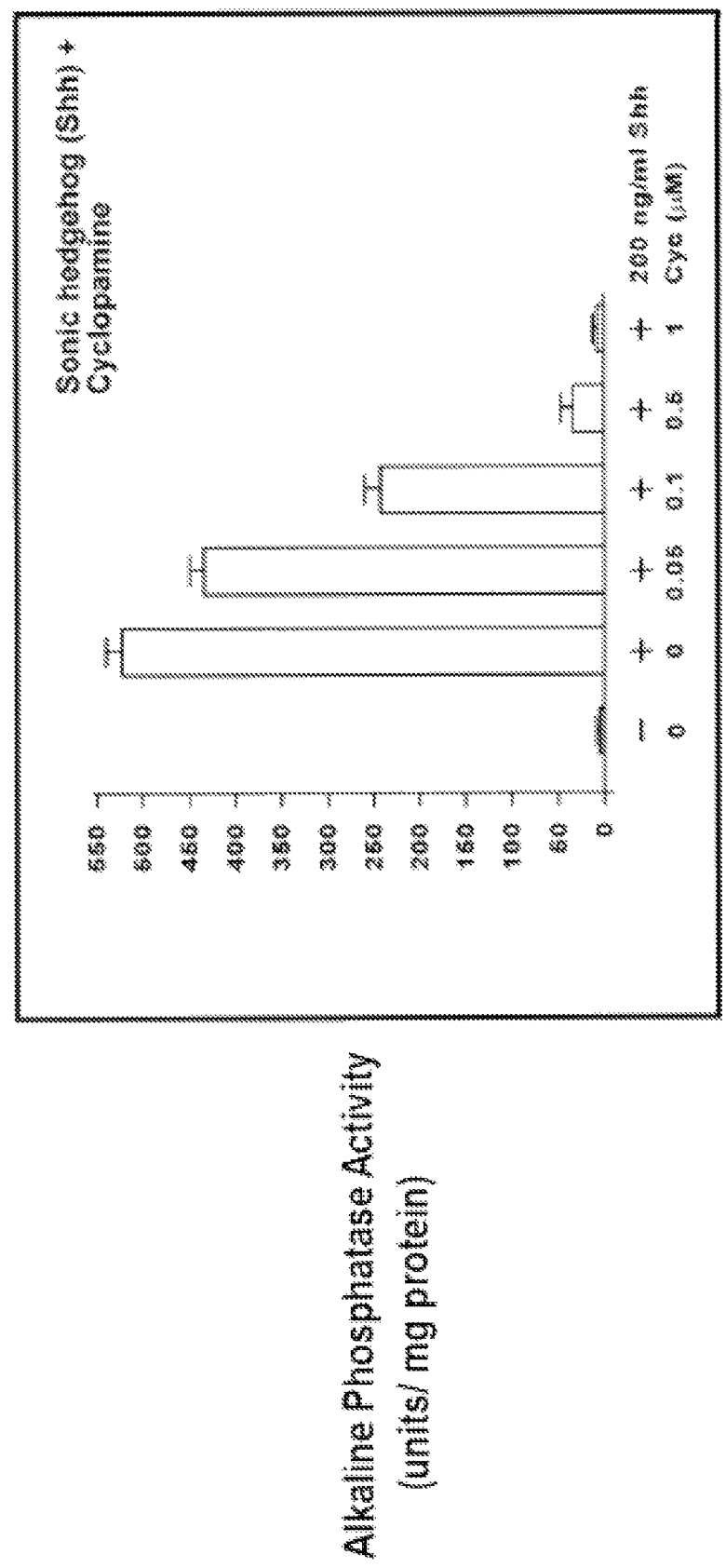
FIG. 1 shows the dose-response of cyclopamine, a positive control, in the alkaline phosphatase assay described herein.

One embodiment provides a compound having the structure of Formula (I):

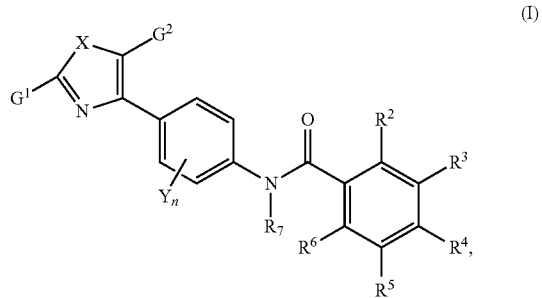

(I)

or a stereoisomer, tautomer, hydrate, solvate or pharmaceutically acceptable salt thereof, wherein:
X is —S—, —O—, —N(H)— or —N($R^1$)—;
Y is halogen, $C_1$-$C_3$ alkyl, —CN, or —$CF_3$;
n is 0, 1, 2 or 3;
$G^1$ is hydrogen, halogen, $C_1$-$C_6$ alkyl, $C_3$-$C_6$ cycloalkyl, —CN, —$CF_3$, or aryl;
$G^2$ is hydrogen, halogen, $C_1$-$C_3$ alkyl, —CN, or —$CF_3$;
$R^1$ is H or $C_1$-$C_3$ alkyl;
$R^2$ is selected from hydrogen, halogen, —CN, alkyl, —$CF_3$, aryl, —O-alkyl, —O-aryl, —O-heteroaryl, —$CH_2$-aryl, —$CH_2$-heteroaryl, —NH-aryl, —$SO_2$-aryl, $SO_2$-alkyl-NH-heteroaryl, —NH-alkyl, —$CH_2$—NH-alkyl, —$CH_2$—N(alkyl)$_2$, —$CH_2$—(N-linked heterocycle), —$CH_2$—(C-linked heterocycle), N-linked heterocycle, and C-linked heterocycle;
$R^4$ is selected from hydrogen, halogen, alkyl, alkoxy, —CN, —$CF_3$, —$SO_2$-alkyl, —$SO_2NH_2$, —$NHSO_2$-alkyl, —$NHSO_2$-aryl, —NHCO-alkyl, —NHCO-aryl, —NHCONH-alkyl, —NHCONH-aryl, —$CONH_2$, —CONH-alkyl, —CONH-aryl, —CON(alkyl)$_2$, —CON(aryl)$_2$, —$CO_2$H, and —$CO_2$alkyl;
$R^3$, $R^5$ and $R^6$ are each independently selected from hydrogen, halogen, —CN, alkyl, aryl, heteroaryl, C-linked heterocycle, —O-alkyl, —O-aryl, —O-heteroaryl, linked heterocycle, —NH-alkyl, —N(alkyl)$_2$, —NH-aryl, —NHheteroaryl, —$CO_2$H, —$CO_2$alkyl, —$SO_2$alkyl, —$SO_2NH_2$, —$SO_2$NHalkyl, —$SO_2$N(alkyl)$_2$, —$NHSO_2$alkyl, —$NHSO_2$aryl, —NHCONH-alkyl, —NHCON(alkyl)$_2$, —N(alkyl)CONH$_2$, —N(alkyl)CONH(alkyl), and —N(alkyl)CON(alkyl)$_2$; and
$R^7$ is H or $C_1$-$C_3$ alkyl.

Another embodiment provides a compound having the structure of Formula (I) wherein X is —S—, —O—.

Another embodiment provides a compound having the structure of Formula (I) wherein $G^1$ and $G^2$ can not both be hydrogen.

Another embodiment provides a compound having the structure of Formula (I) wherein:
- X is —S—, —O—, —N(H)— or —N($R^1$)—;
- Y is halogen, $C_1$-$C_3$ alkyl, —CN, or —$CF_3$;
- n is 0, 1, 2 or 3;
- $G^1$ is hydrogen, halogen, $C_1$-$C_3$ alkyl, —CN, or —$CF_3$;
- $G^2$ is hydrogen, halogen, $C_1$-$C_3$ alkyl, —CN, or —$CF_3$, and wherein $G^1$ and $G^2$ can not both be hydrogen;
- $R^1$ is H or $C_1$-$C_3$ alkyl;
- $R^2$ is selected from halogen, —CN, alkyl, aryl, —O-aryl, —O-heteroaryl, —$CH_2$-aryl, —$CH_2$-heteroaryl, —NH-aryl, —$SO_2$-aryl, —NH-heteroaryl, —NH-alkyl, —$CH_2$—NH-alkyl, —$CH_2$—N(alkyl)$_2$, —$CH_2$—(N-linked heterocycle), —$CH_2$—(C-linked heterocycle), N-linked heterocycle, and C-linked heterocycle;
- $R^4$ is selected from alkoxy, —CN, —$SO_2$-alkyl, —$SO_2NH_2$, —$NHSO_2$-alkyl, —$NHSO_2$-aryl, —NHCO-alkyl, —NHCO-aryl, —NHCONH-alkyl, —NHCONH-aryl, —$CONH_2$, —CONH-alkyl, —CONH-aryl, —CON(alkyl)$_2$, —CON(aryl)$_2$, —$CO_2$H, and —$CO_2$alkyl; and
- $R^3$, $R^5$ and $R^6$ are each independently selected from hydrogen, halogen, —CN, alkyl, aryl, heteroaryl, C-linked heterocycle, —O-alkyl, —O-aryl, —O-heteroaryl, N-linked heterocycle, —NH-alkyl, —N(alkyl)$_2$, —NH-aryl, —NHheteroaryl, —$CO_2$H, —$CO_2$alkyl, —$SO_2$alkyl, —$SO_2NH_2$, —$SO_2$NHalkyl, —$SO_2$N(alkyl)$_2$, —$NHSO_2$alkyl, —$NHSO_2$aryl, —NHCONH-alkyl, —NHCON(alkyl)$_2$, —N(alkyl)CONH$_2$, —N(alkyl)CONH(alkyl), and —N(alkyl)CON(alkyl)$_2$.

Another embodiment provides a compound having the structure of Formula (I) wherein n is 0.

Another embodiment provides a compound having the structure of Formula (I) wherein n is 1.

Another embodiment provides a compound having the structure of Formula (I) wherein $G^2$ is H.

Another embodiment provides a compound having the structure of Formula (I) wherein $G^2$ is H and $G^1$ is alkyl.

Another embodiment provides a compound having the structure of Formula (I) wherein X is —S—.

Another embodiment provides a compound having the structure of Formula (I) wherein $R^2$ is —$CH_2$—NH-alkyl, —$CH_2$—N(alkyl)$_2$, —$CH_2$—(N-linked heterocycle), or —$CH_2$—(C-linked heterocycle).

Another embodiment provides a compound having the structure of Formula (I) wherein $R^2$ is halogen, —CN, -alkyl, or —$CF_3$.

Another embodiment provides a compound having the structure of Formula (I) wherein $R^4$ is —$SO_2$Me or —OMe.

Another embodiment provides a compound having the structure of Formula (I) wherein $R^2$ is halogen and $R^4$ is —$SO_2$Me.

Another embodiment provides a compound having the structure of Formula (I) wherein $R^2$ is halogen and $R^4$ is —OMe.

Another embodiment provides a compound having the structure of Formula (I) wherein n is 0; $G^2$ is H; $G^1$ is alkyl; X is —S—; $R^2$ is halogen and $R^4$ is —OMe.

Another embodiment provides a compound having the structure of Formula (I) wherein n is 0; $G^2$ is H; $G^1$ is alkyl; X is —S—; $R^2$ is halogen and $R^4$ is —$SO_2$Me.

In certain specific embodiments, the compounds of Formula (I) have the structures shown in Table 1.

TABLE 1

| Example | Structure |
|---|---|
| 1 | 2,4-dichloro-N-(4-(2-methylthiazol-4-yl)phenyl)benzamide |
| 2 | 3,4,5-trimethoxy-N-(4-(2-methylthiazol-4-yl)phenyl)benzamide |
| 3 | 4-methoxy-N-(4-(2-methylthiazol-4-yl)phenyl)benzamide |
| 4 | 2-chloro-4-(methylsulfonyl)-N-(4-(2-methylthiazol-4-yl)phenyl)benzamide |
| 5 | 4-methoxy-N-(4-(2-methylthiazol-4-yl)phenyl)-2-(morpholinomethyl)benzamide |

TABLE 1-continued

| Example | Structure |
|---|---|
| 6 | 2-chloro-N-(4-(2-methyloxazol-4-yl)phenyl)-4-(methylsulfonyl)benzamide |
| 7 | 2-chloro-N-(3-chloro-4-(2-methylthiazol-4-yl)phenyl)-4-(methylsulfonyl)benzamide |
| 8 | 2-chloro-4-methoxy-N-(4-(2-methylthiazol-4-yl)phenyl)benzamide |
| 9 | 2-chloro-N-methyl-4-(methylsulfonyl)-N-(4-(2-methylthiazol-4-yl)phenyl)benzamide |
| 10 | 2-chloro-N-(4-(thiazol-4-yl)phenyl)benzamide |
| 11 | 2-chloro-4-(methylsulfonyl)-N-(4-(thiazol-4-yl)phenyl)benzamide |
| 12 | 2-chloro-N-(4-(2-(2-hydroxypropan-2-yl)thiazol-4-yl)phenyl)-4-(methylsulfonyl)benzamide |
| 13 | 2-chloro-N-(4-(2-(hydroxymethyl)thiazol-4-yl)phenyl)-4-(methylsulfonyl)benzamide |
| 14 | 2-chloro-N-(4-(2-methylthiazol-4-yl)phenyl)benzamide |
| 15 | 2-(methylsulfonyl)-N-(4-(2-methylthiazol-4-yl)phenyl)benzamide |

TABLE 1-continued
| Example | Structure |
|---|---|
| 16 | 4-methoxy-2-methyl-N-(4-(2-methylthiazol-4-yl)phenyl)benzamide |
| 17 | 2-fluoro-4-methoxy-N-(4-(2-methylthiazol-4-yl)phenyl)benzamide |
| 18 | 4-cyano-N-(4-(2-methylthiazol-4-yl)phenyl)benzamide |
In further embodiments, a compound of Formula (I) is selected from the structures shown below as examples 19-193.
Example 19
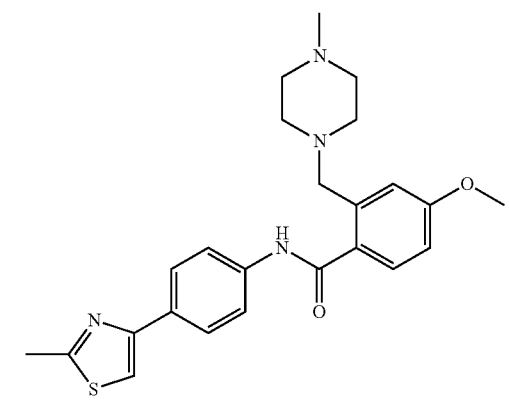
Example 20
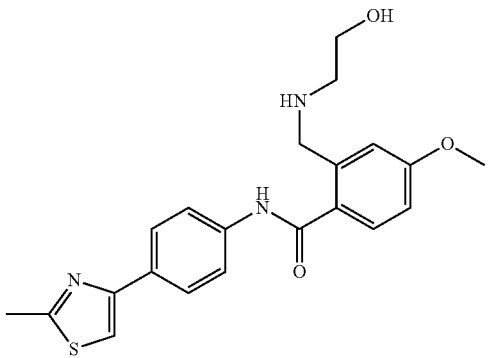
example 21
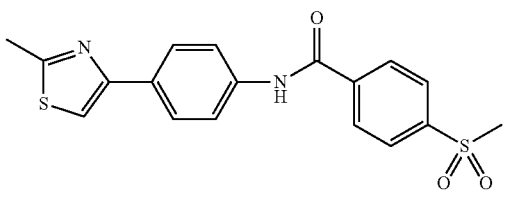
example 22
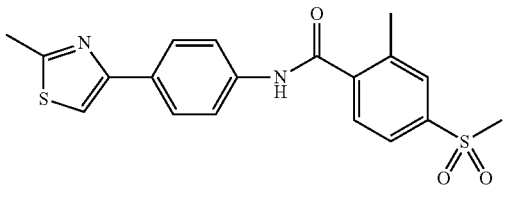
example 23
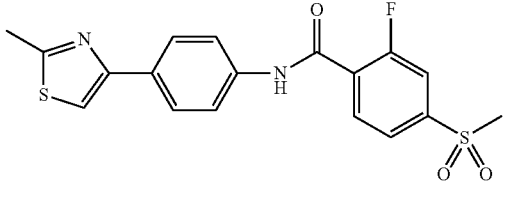
example 24
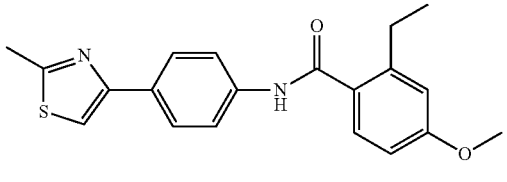
example 25
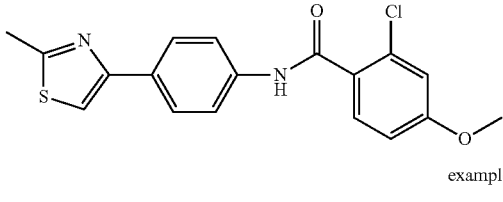
example 26
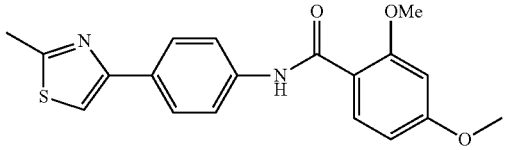

example 27
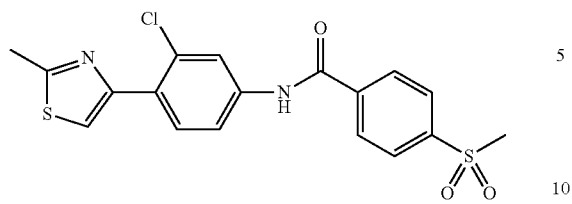
example 28
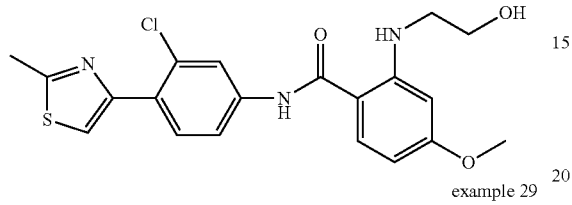
example 29
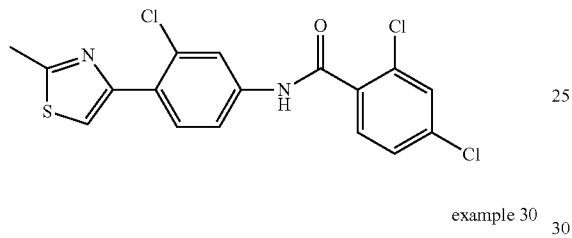
example 30
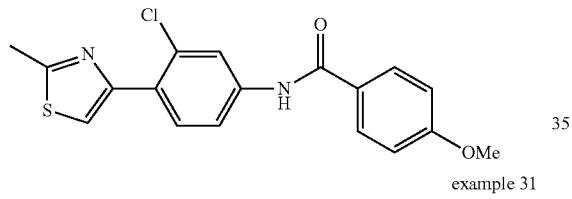
example 31
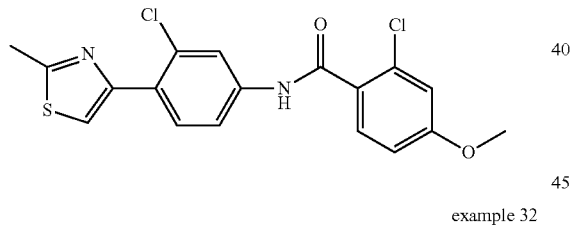
example 32
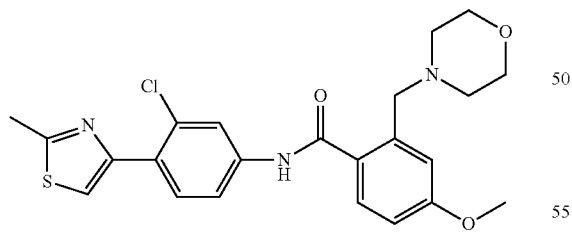
example 33
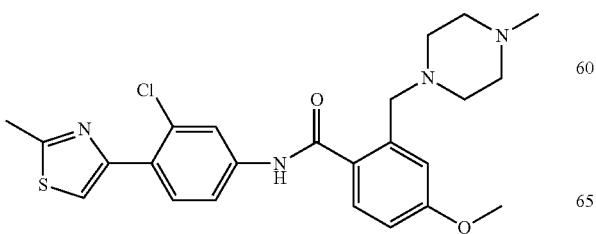
example 34
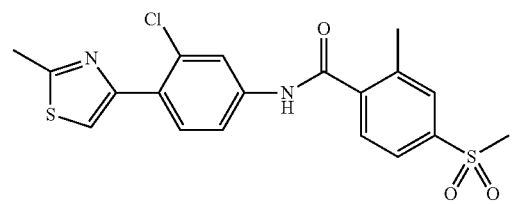
example 35
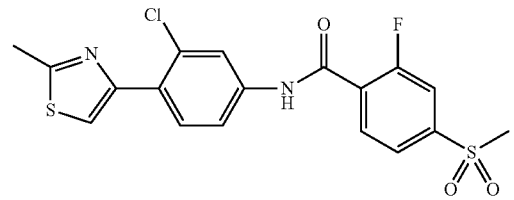
example 36
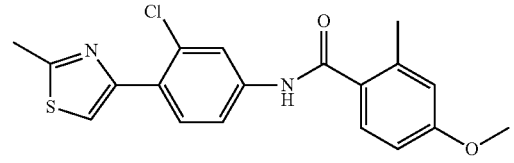
example 37
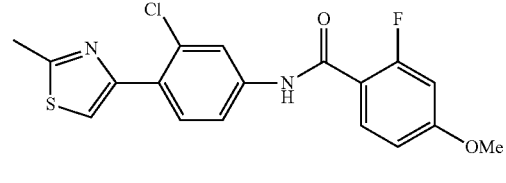
example 38
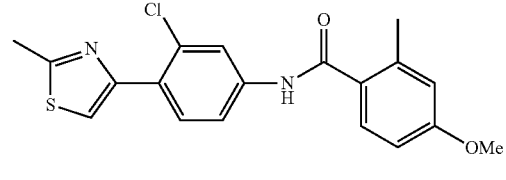
example 39
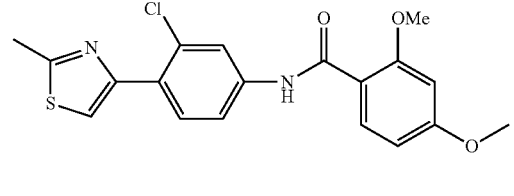
example 40
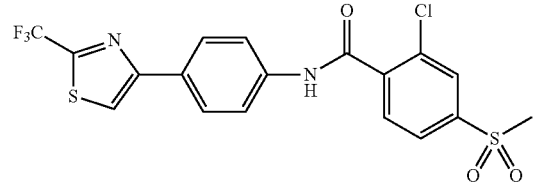

-continued
example 41
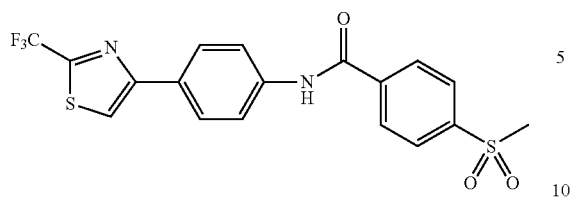
example 42
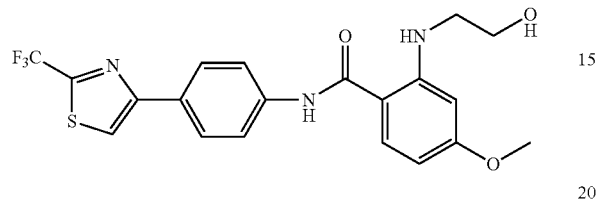
example 43
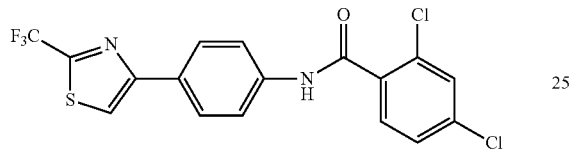
example 44
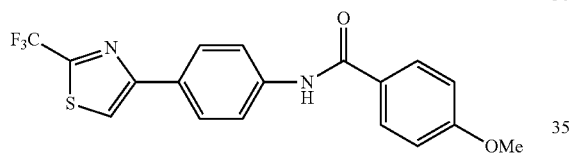
example 45
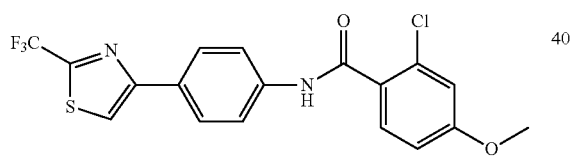
example 46
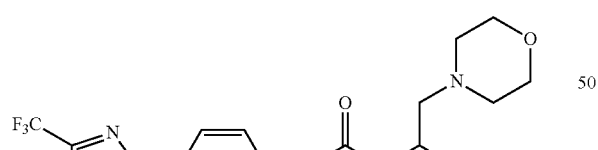
example 47
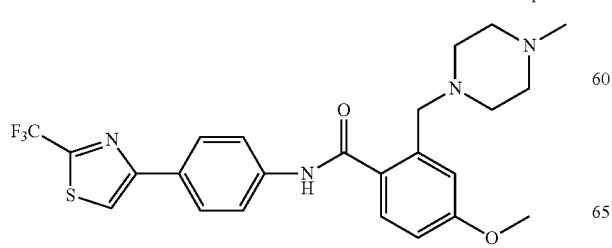
-continued
example 48
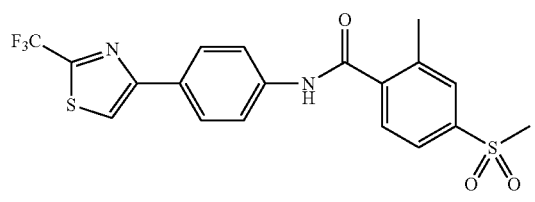
example 49
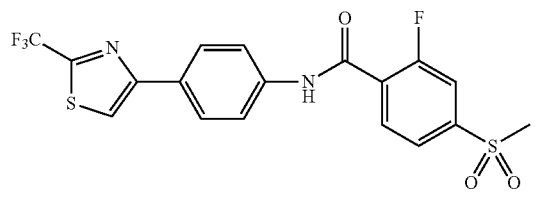
example 50
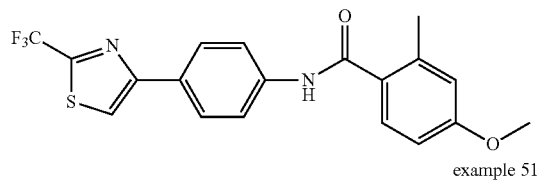
example 51
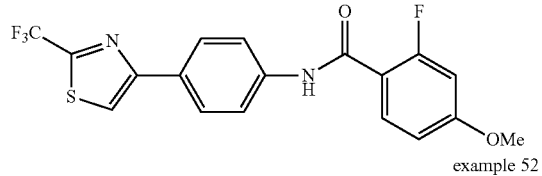
example 52
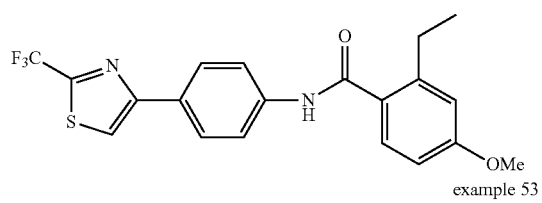
example 53
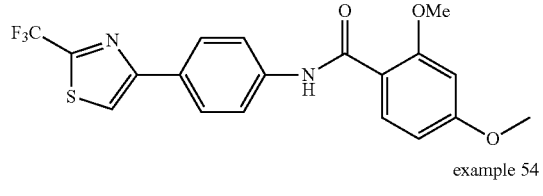
example 54
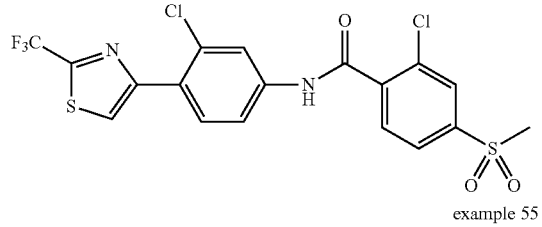
example 55

-continued
example 56
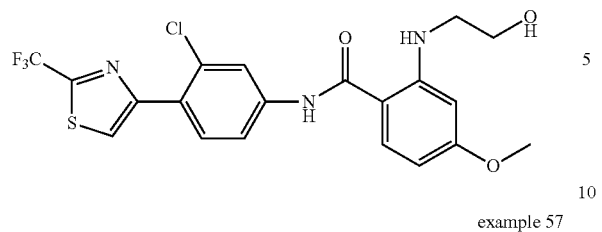
example 57
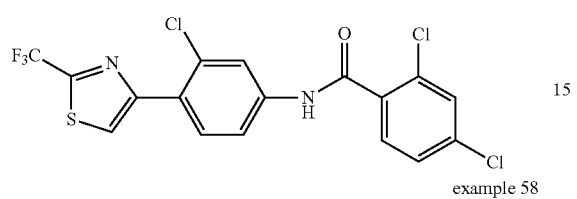
example 58
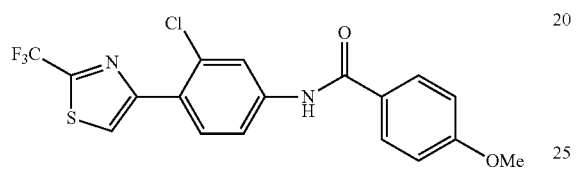
example 59
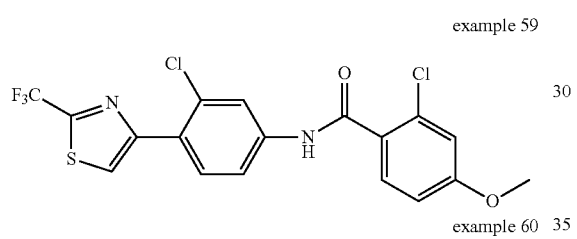
example 60
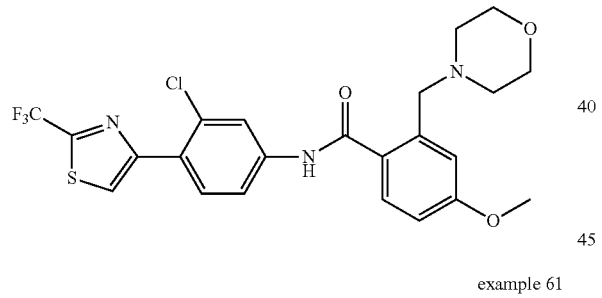
example 61
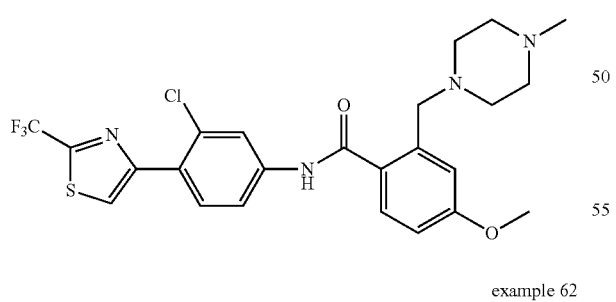
example 62
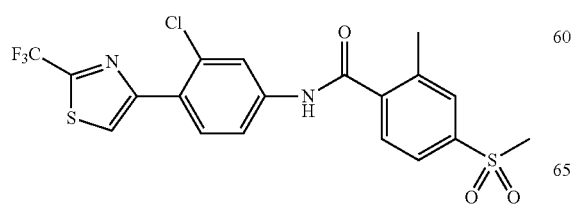
-continued
example 63
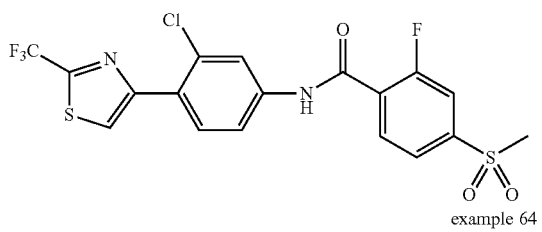
example 64
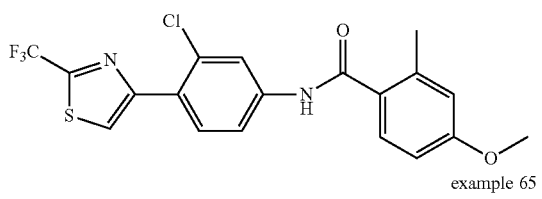
example 65
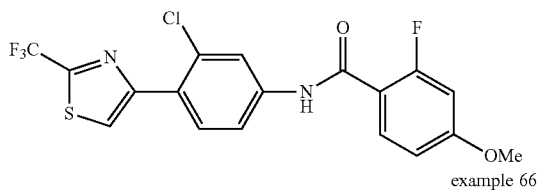
example 66
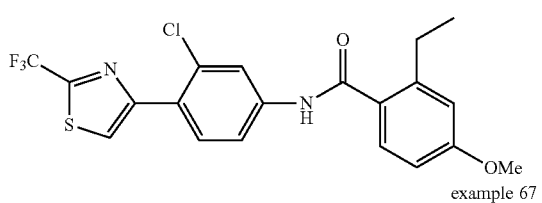
example 67
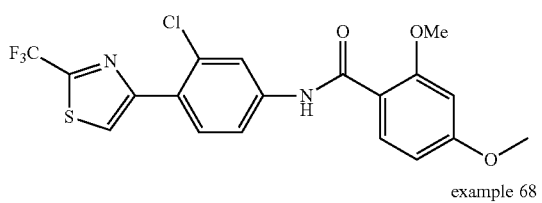
example 68
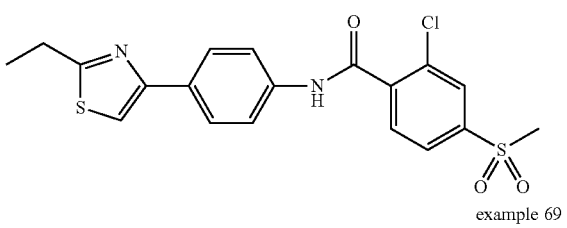
example 69
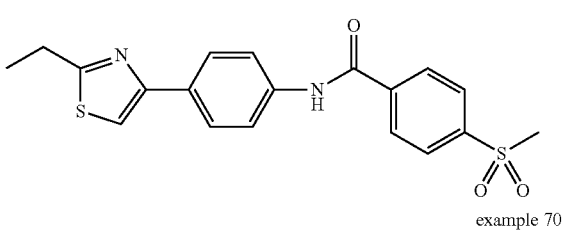
example 70
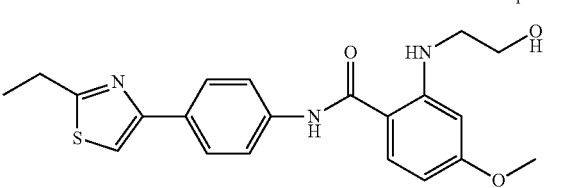

example 71
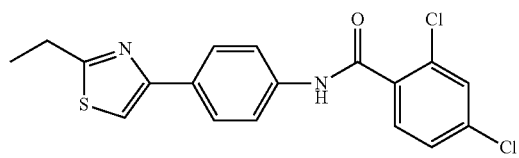
example 72
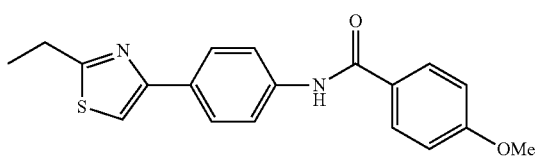
example 73
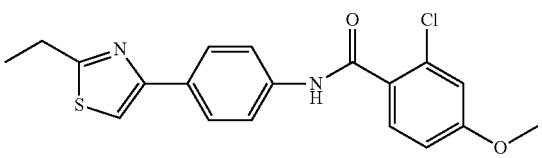
example 74
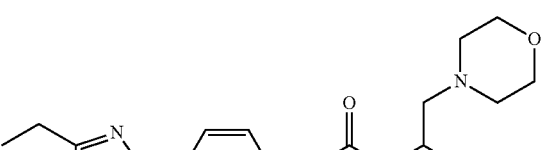
example 75
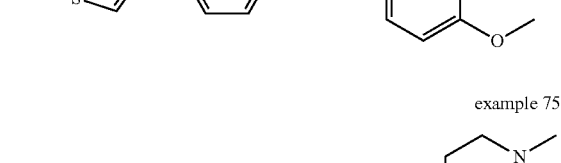
example 76
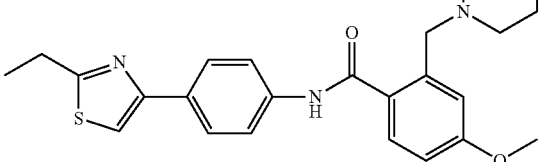
example 77
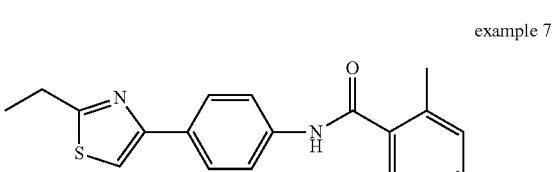
example 78
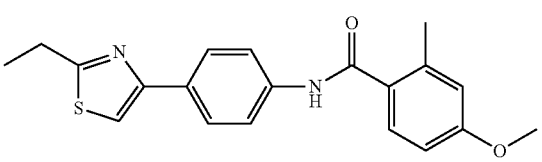
example 79
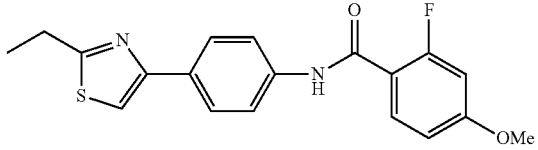
example 80
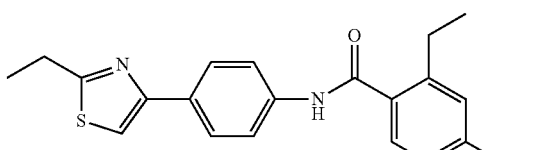
example 81
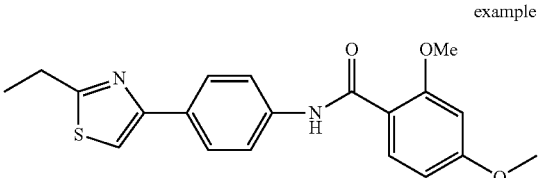
example 82
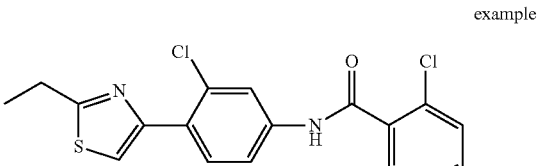
example 83
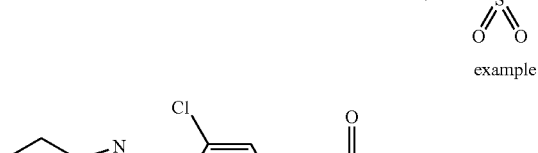
example 84
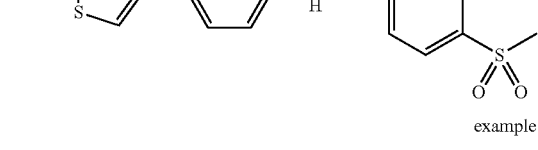
example 85
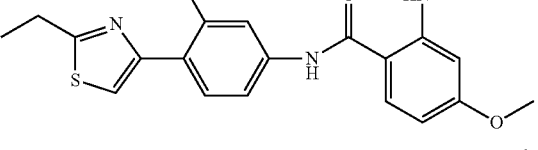

example 86
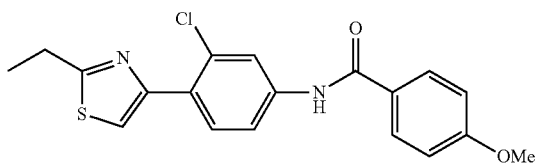
example 87
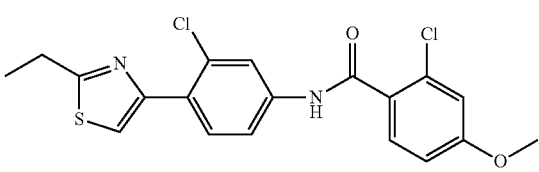
example 88
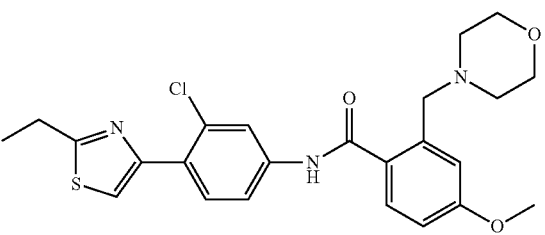
example 89
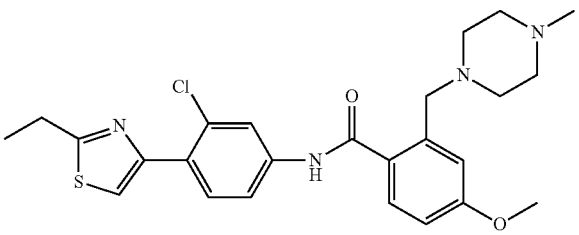
example 90
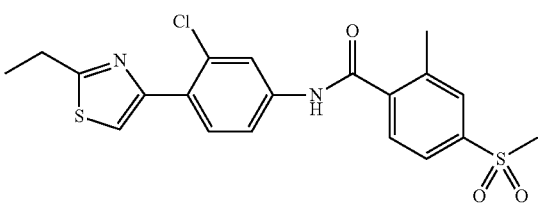
example 91
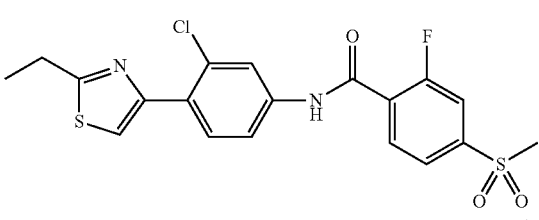
example 92
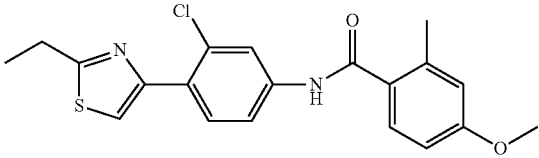
example 93
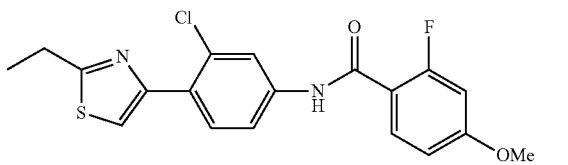
example 94
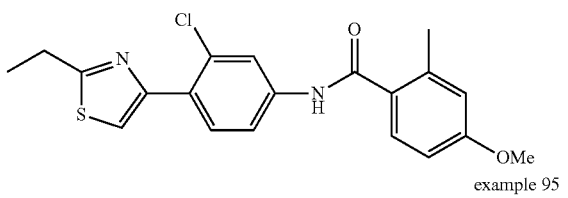
example 95
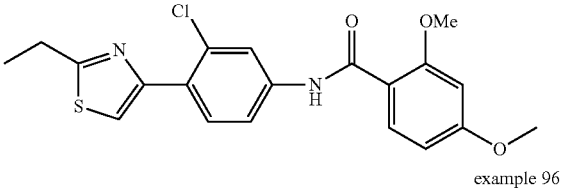
example 96
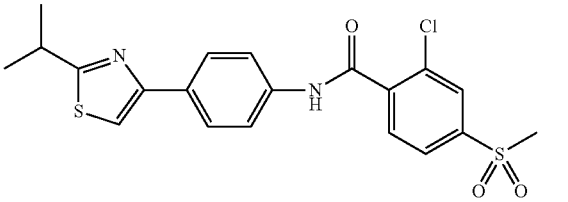
example 97
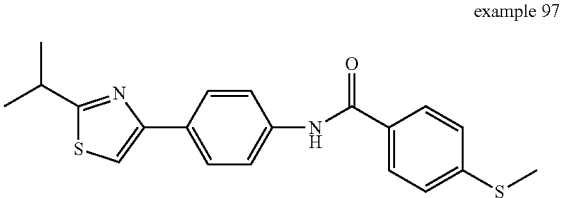
example 98
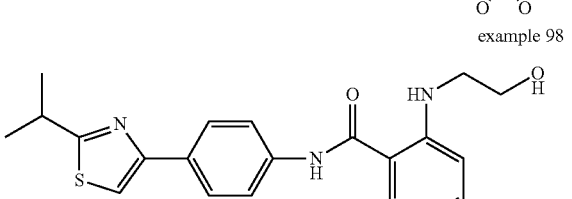
example 99
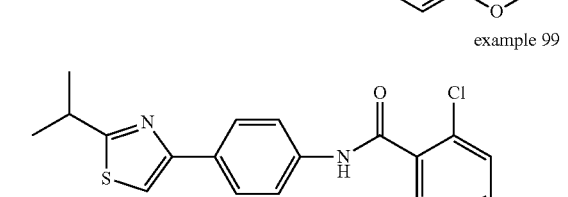
example 100
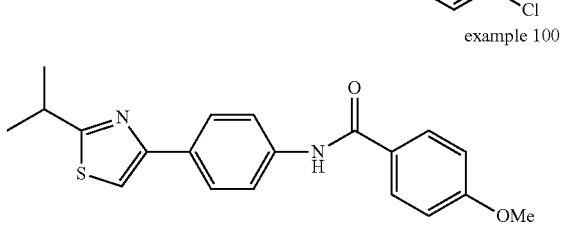

example 101
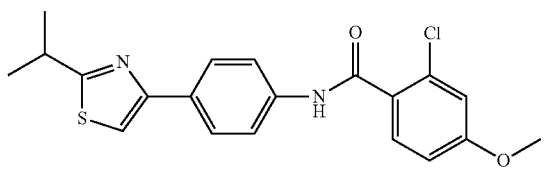
example 102
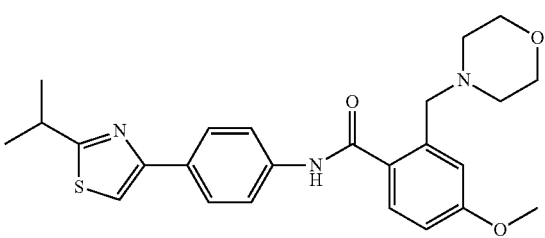
example 103
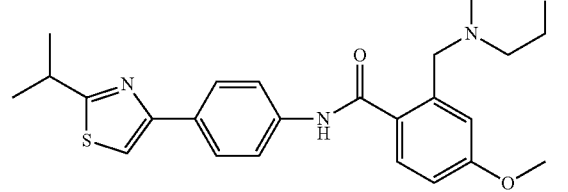
example 104
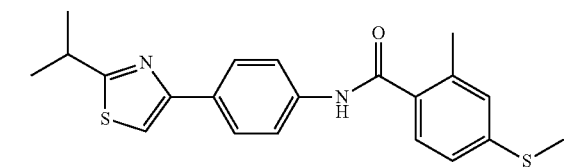
example 105
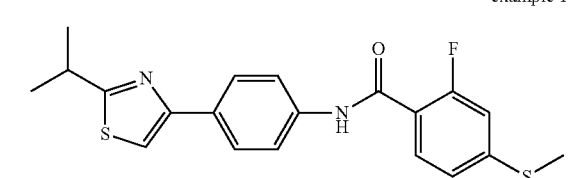
example 106
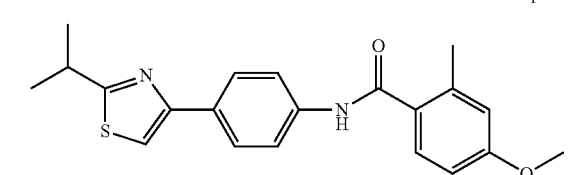
example 107
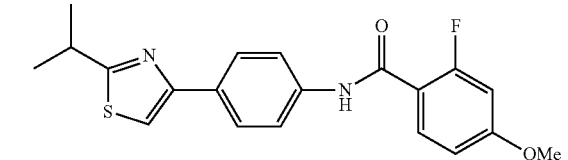
example 108
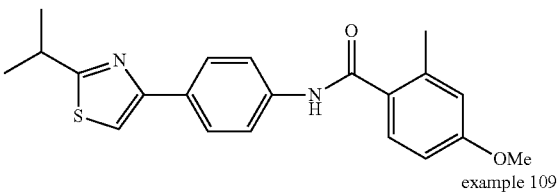
example 109
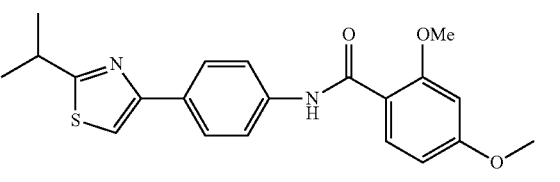
example 110
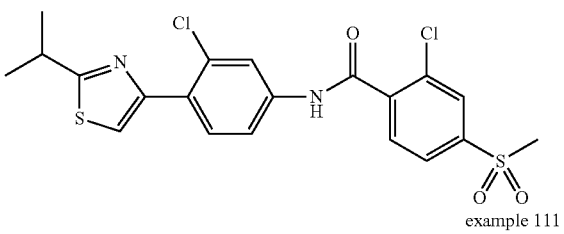
example 111
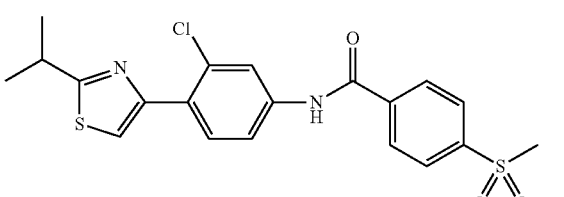
example 112
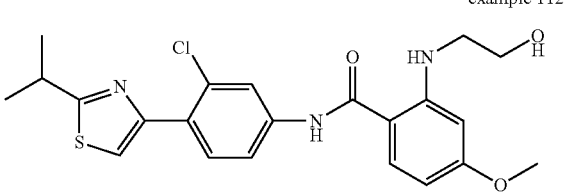
example 113
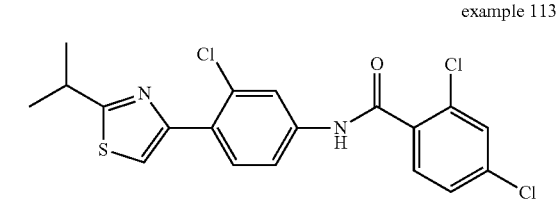
example 114
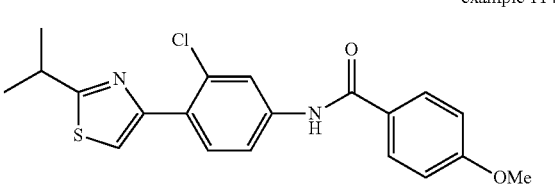
example 115
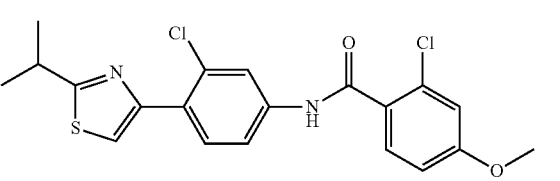

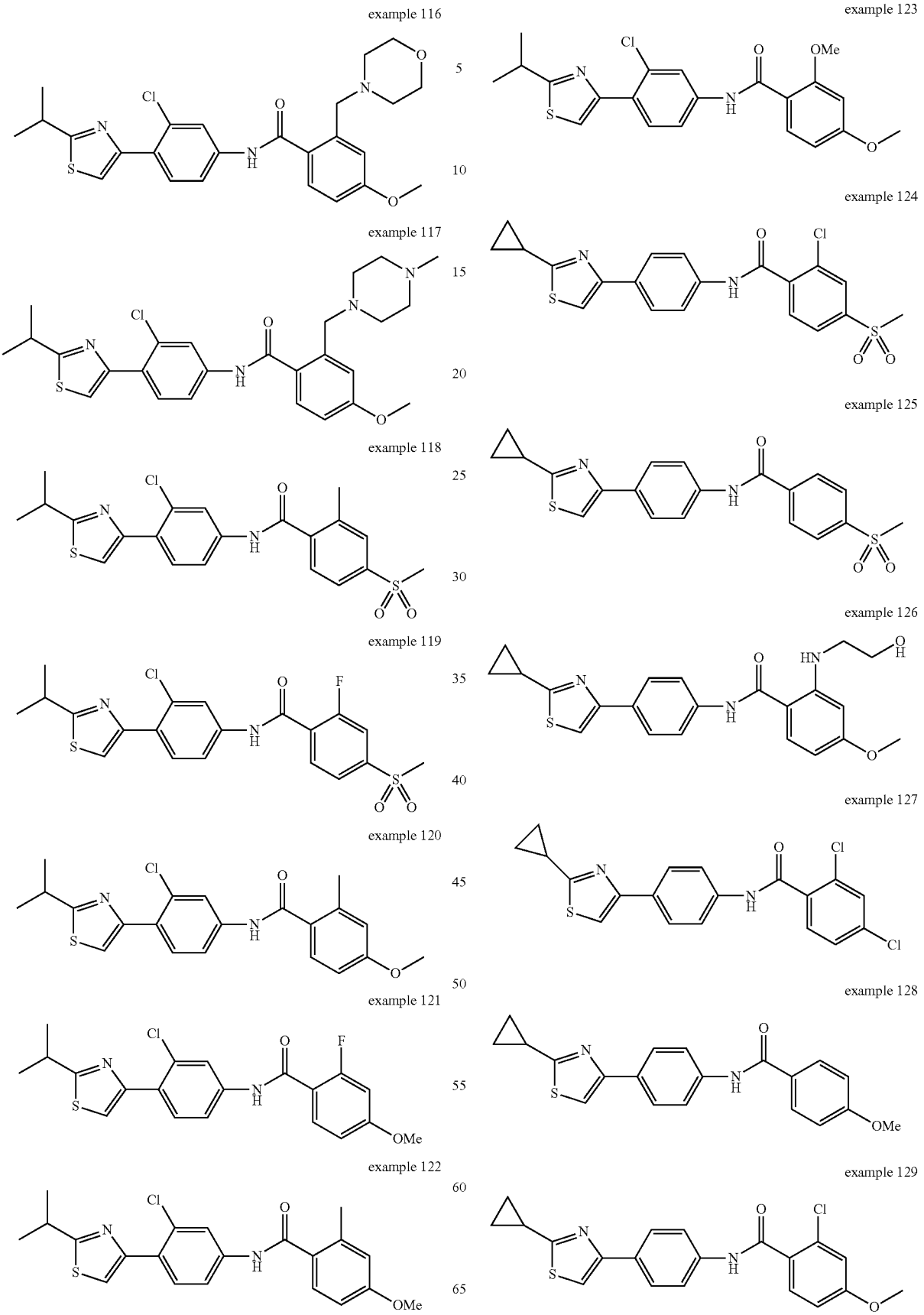

example 130
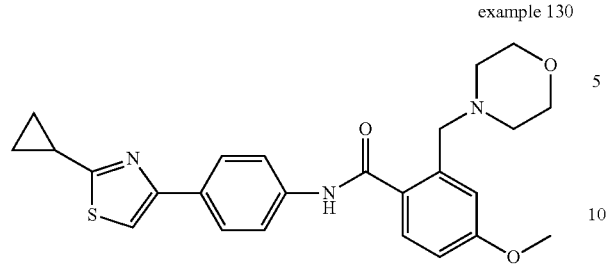
example 131
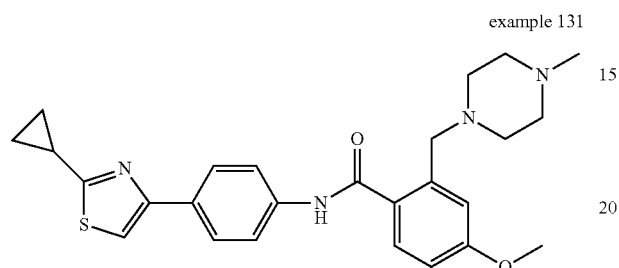
example 132
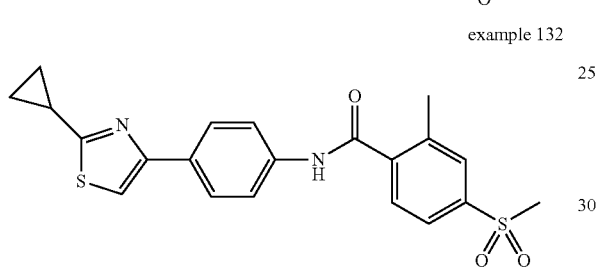
example 133
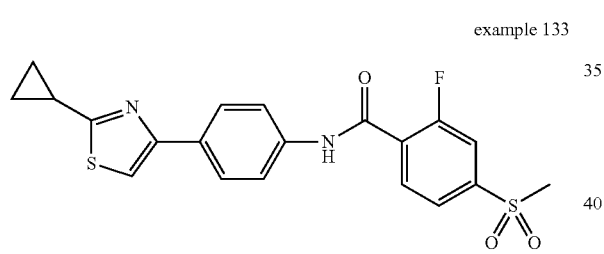
example 134
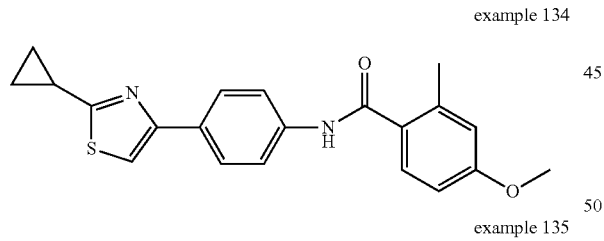
example 135
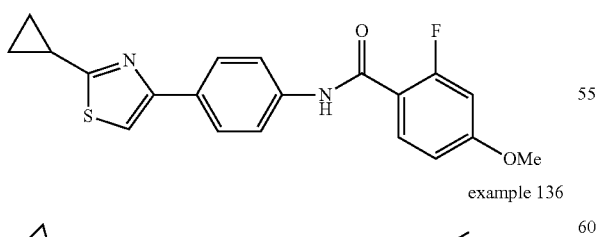
example 136
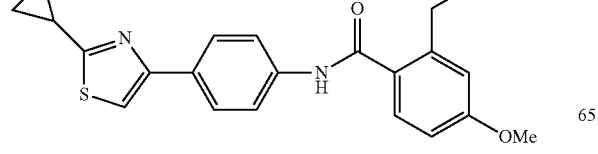
example 137
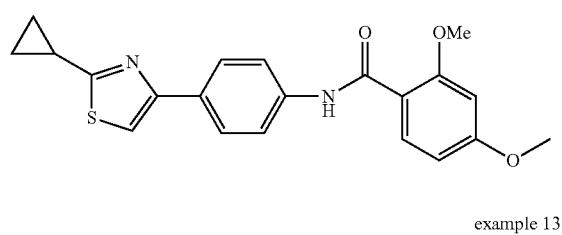
example 138
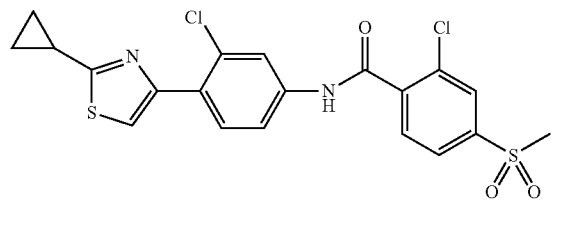
example 139
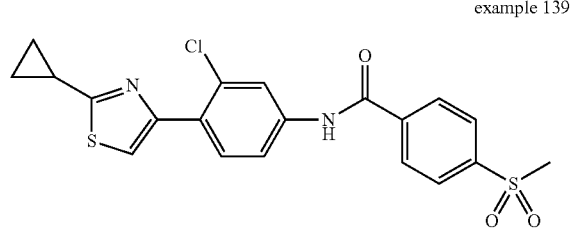
example 140
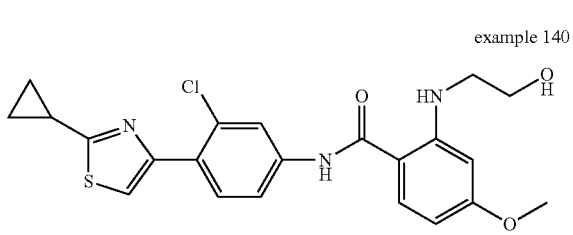
example 141
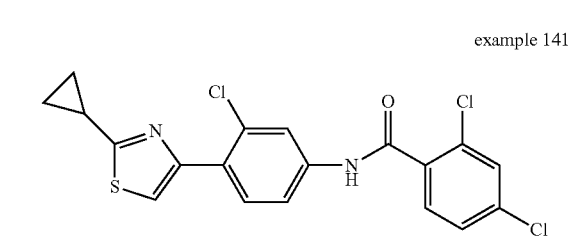
example 142
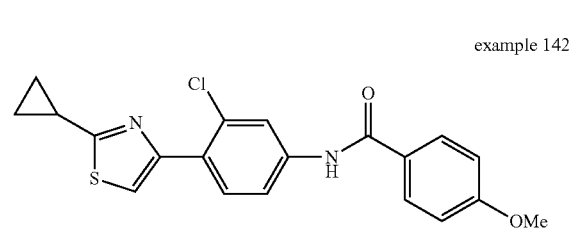
example 143
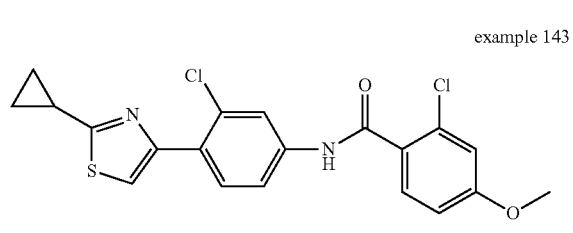

example 144
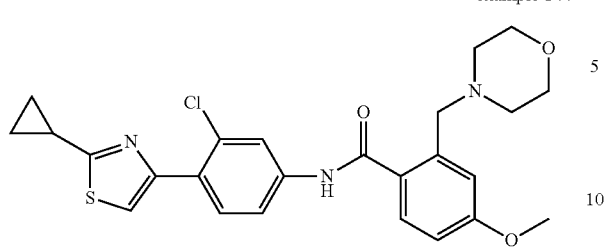
example 145
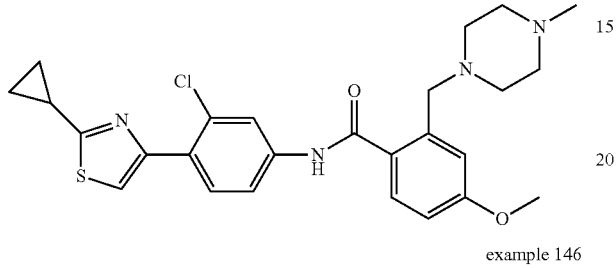
example 146
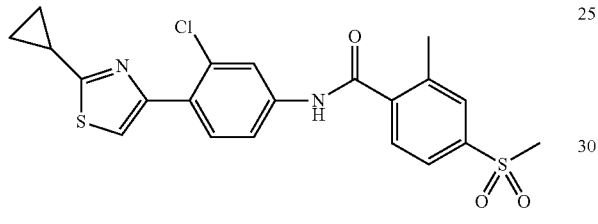
example 147
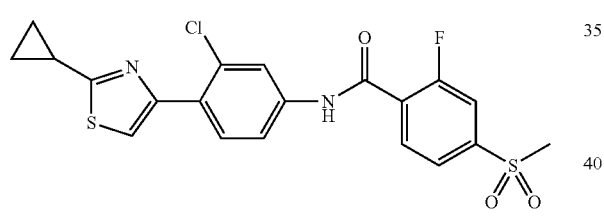
example 148
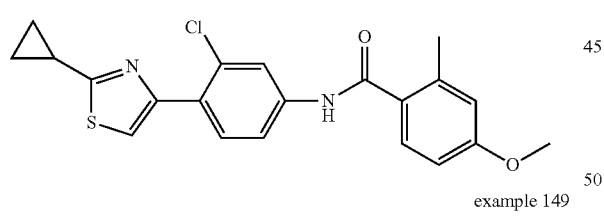
example 149
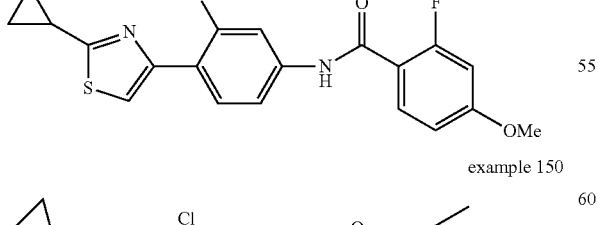
example 150
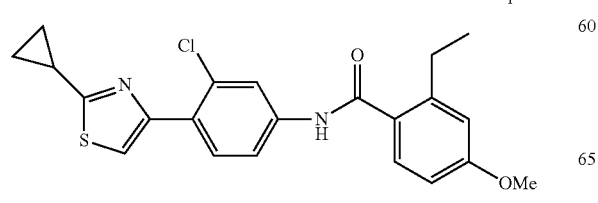
example 151
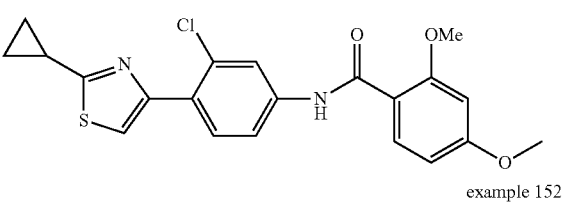
example 152
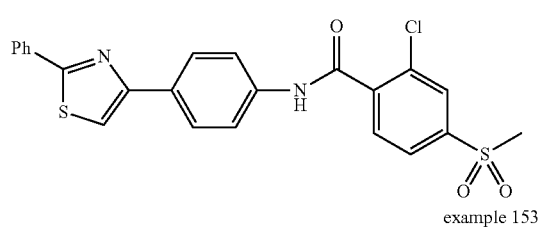
example 153
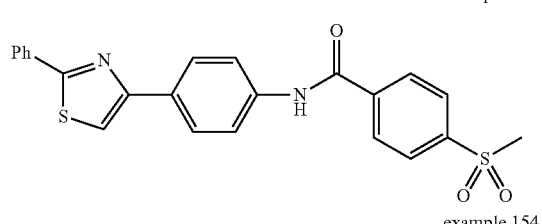
example 154
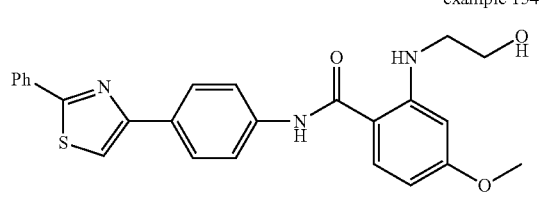
example 155
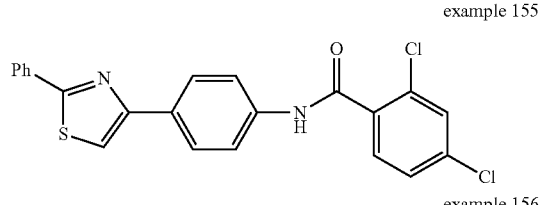
example 156
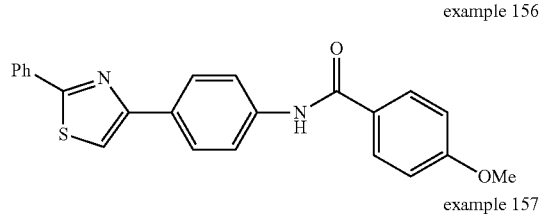
example 157
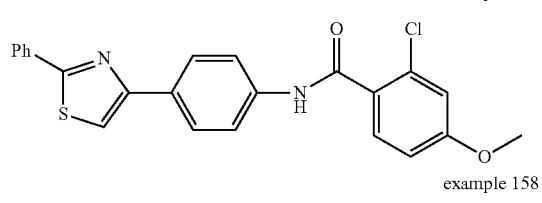
example 158
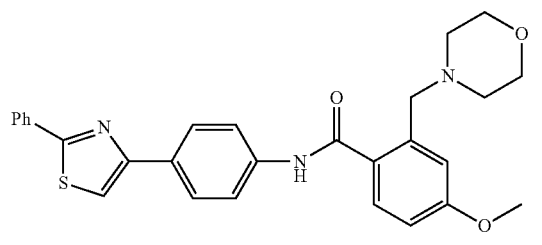

example 159
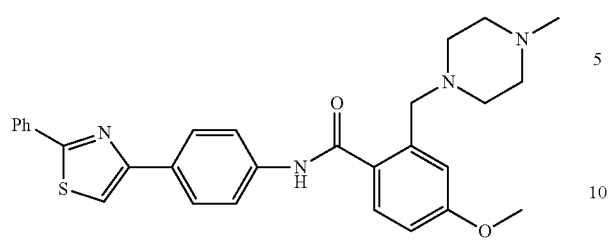
example 160
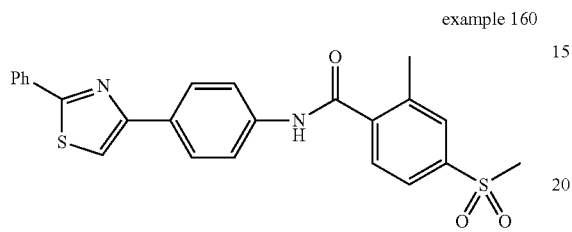
example 161
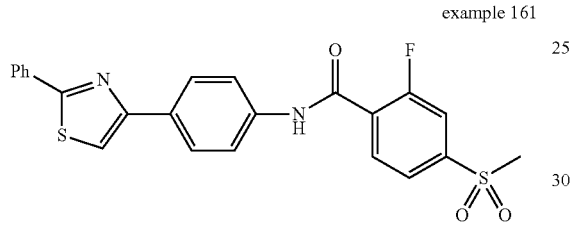
example 162
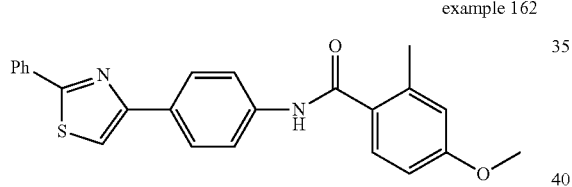
example 163
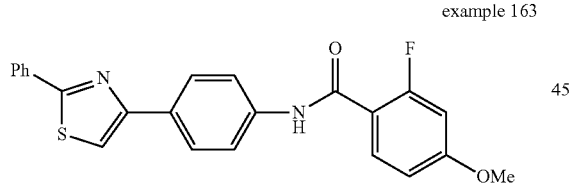
example 164
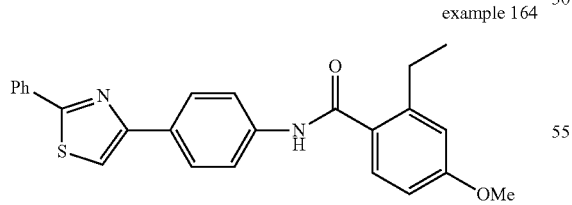
example 165
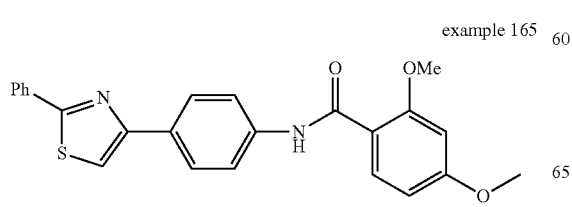
example 166
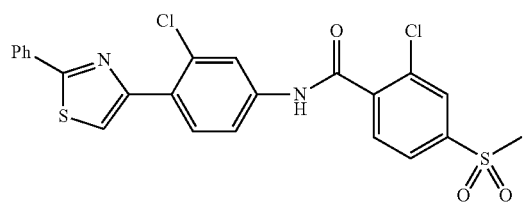
example 167
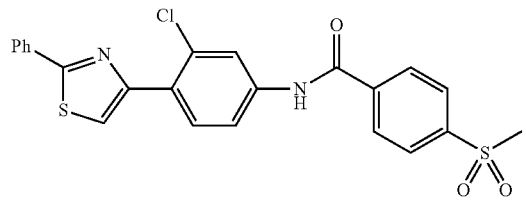
example 168
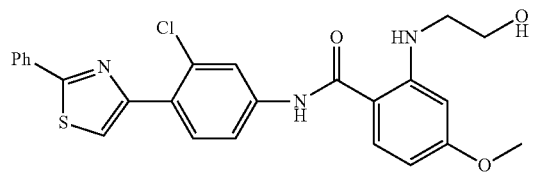
example 169
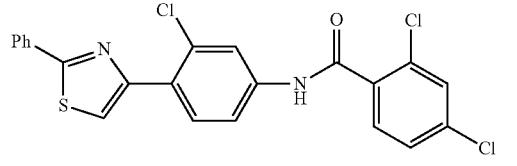
example 170
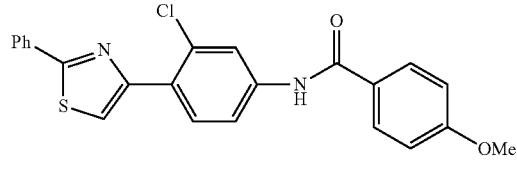
example 171
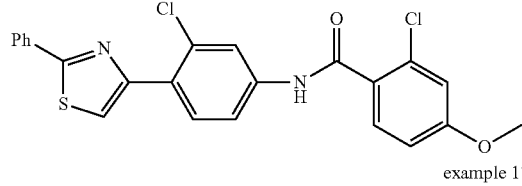
example 172
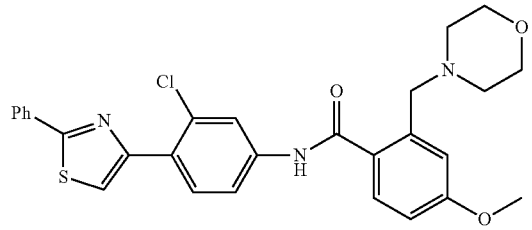

example 173
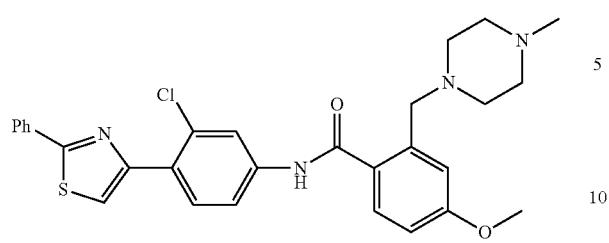
example 174
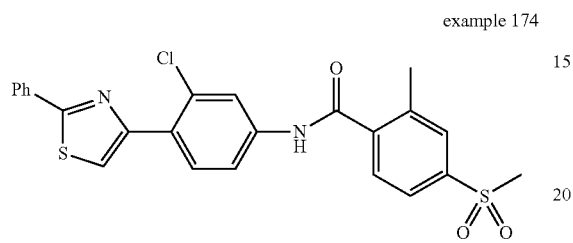
example 175
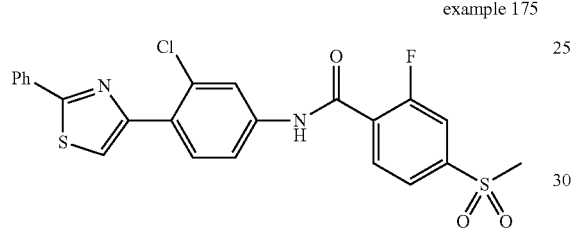
example 176
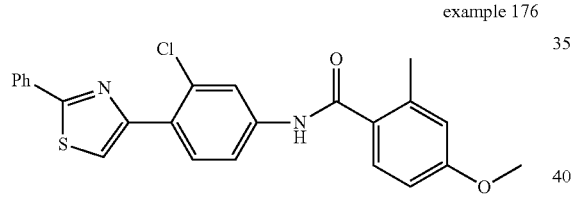
example 177
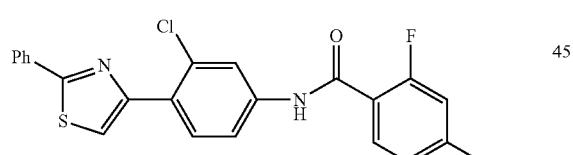
example 178
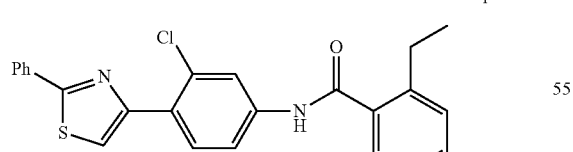
example 179
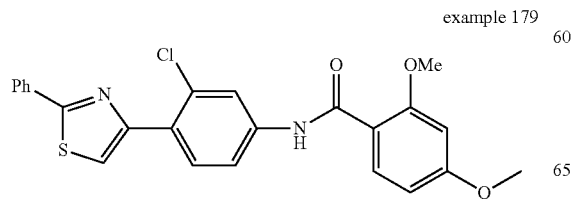
Example 180
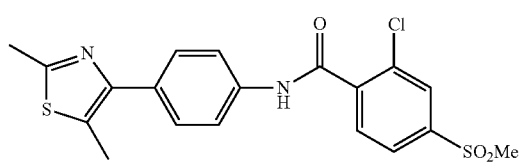
Example 181
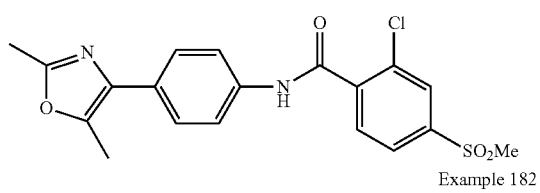
Example 182
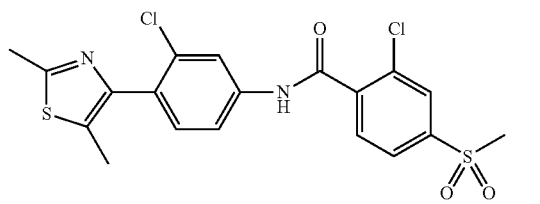
Example 183
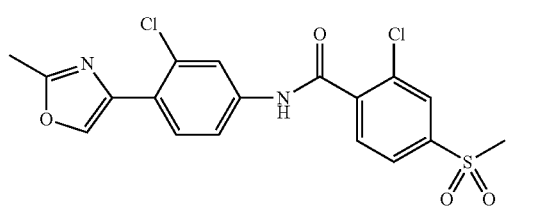
Example 184
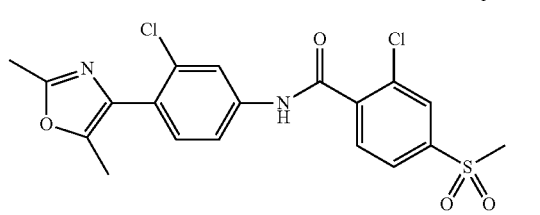
Example 185
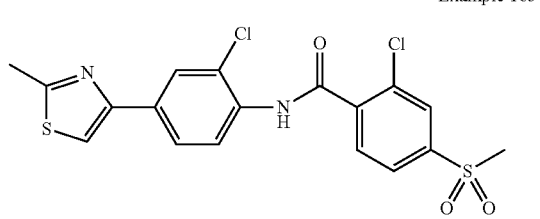
Example 186
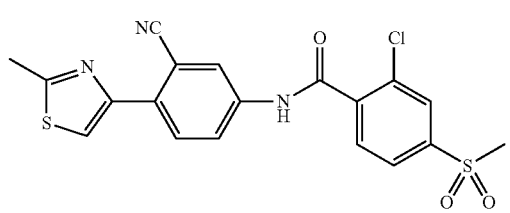

Example 187
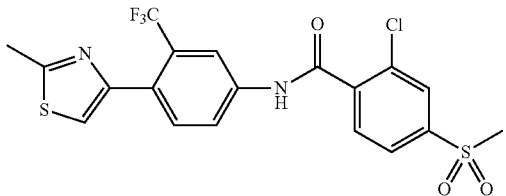

Example 188
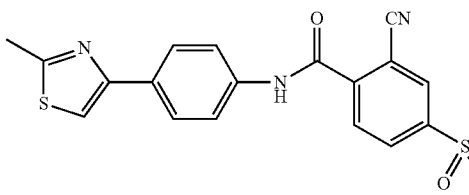

Example 189
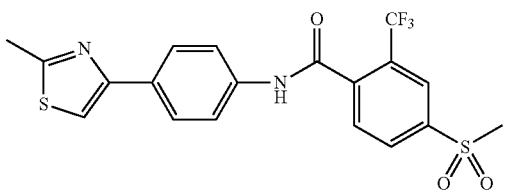

Example 190
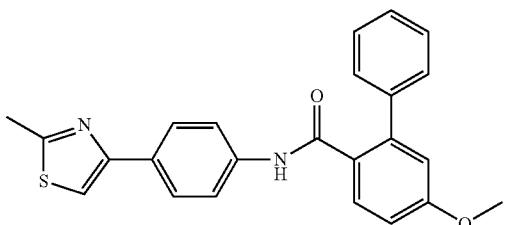

Example 191
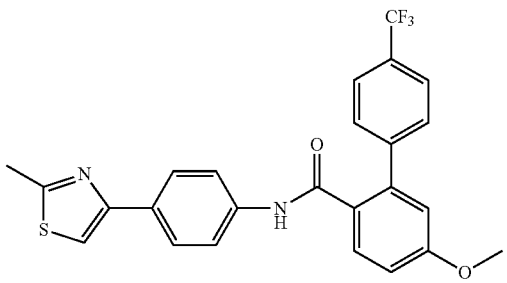

Example 192
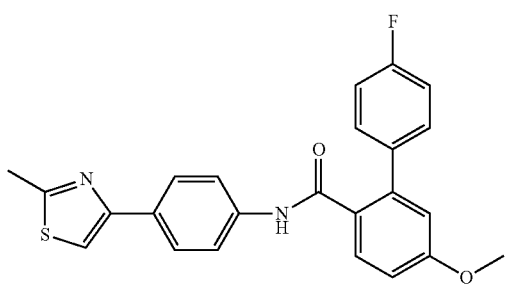

Example 193
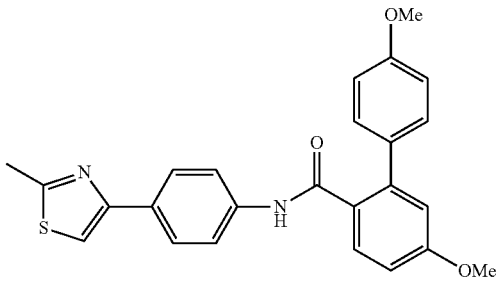

DEFINITIONS

As used herein and in the appended claims, the singular forms "a", "and", and "the" include plural referents unless the context clearly dictates otherwise. Thus, for example, reference to "a compound" includes a plurality of such compounds, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Imino" refers to the =NH radical.
"Thioxo" refers to the =S radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl. Unless stated otherwise in the specification, an alkyl group is optionally a fluorinated or perfluorinated alkyl group, such as CF$_3$, CF$_2$CF$_3$, CH$_2$F, CHF$_2$, CH$_2$CF$_3$ and the like.

"Alkenyl" refers to a straight or branched hydrocarbon chain radical group consisting solely of carbon and hydrogen atoms, containing at least one double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain is optionally substituted by one or more of the following substituents: halo, cyano, nitro, aryl, cycloalkyl, heterocyclyl, heteroaryl, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain is optionally substituted by one or more of the following substituents: halo, cyano, nitro, aryl, cycloalkyl, heterocyclyl, heteroaryl, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. Aryl groups include, but are not limited to, groups such as phenyl, fluorenyl, and naphthyl. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, benzyl, diphenylmethyl and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is optionally saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—SR$^a$, —R$^b$—OC(O)—R$^a$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Carbocyclylalkyl" refers to a radical of the formula —R$^c$-carbocyclyl where R$^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, and includes fused or bridged ring systems. The heteroatoms in the heterocyclyl radical is optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—SR$^a$, —R$^b$—OC(O)—R$^a$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —R$^c$-heterocyclyl where R$^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

The compounds, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. When the compounds described herein contain olefinic double bonds or other centers of geometric asymmetry, and unless specified otherwise, it is intended that the compounds include both E and Z geometric isomers (e.g., cis or trans). Likewise, all possible isomers, as well as their racemic and optically pure forms, and all tautomeric forms are also intended to be included.

A "stereoisomer" refers to the relationship between two or more compounds made up of the same atoms bonded by the same bonds but having different three-dimensional structures, which are not superimposable. The term "enantiomer" refers to two stereoisomers that are nonsuperimposeable mirror images of one another. It is contemplated that the various stereoisomers of the compounds disclosed herein, and mixtures thereof, are within the scope of the present disclosure and specifically includes enantiomers.

A "tautomer" refers to a compound wherein a proton shift from one atom of a molecule to another atom of the same molecule is possible. The compounds presented herein may exist as tautomers. In solutions where tautomerization is possible, a chemical equilibrium of the tautomers will exist. The exact ratio of the tautomers depends on several factors, including temperature, solvent, and pH. Some examples of tautomeric equilibrium are shown below.

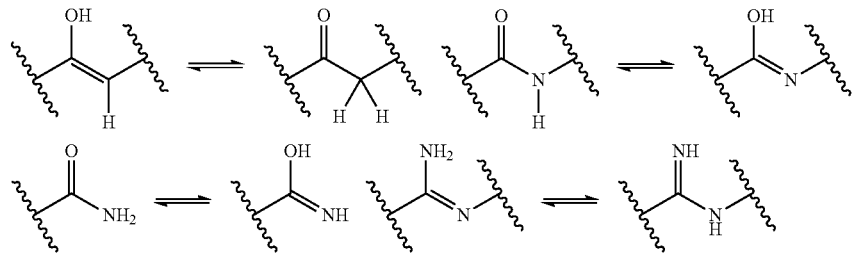

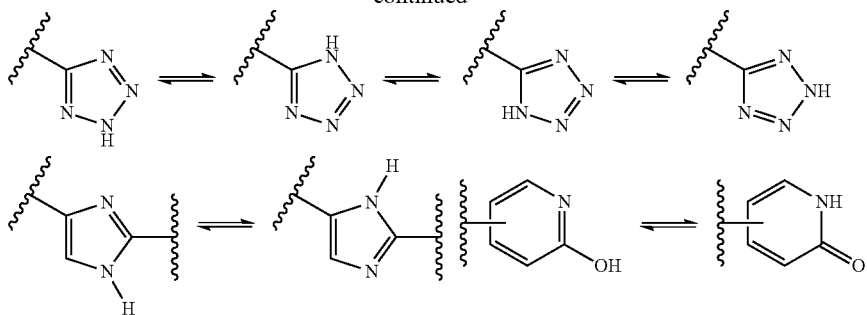

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

General Methods for the Synthesis of Heterocyclic Benzamide Hedgehog Inhibitors

Synthetic Schemes 1-5 illustrate general methods for the synthesis of benzamide hedgehog inhibitors. The generic substituents illustrated in Schemes 1-5 are defined by Formula (I) as previously presented herein.

Scheme 1 illustrates the synthesis of benzamide hedgehog inhibitors. Methyl 2-iodo-4-methylsulfonylbenzoate is subjected to hydrolysis of the ester followed by coupling with a heterocycle substituted aniline gives the advanced benzamide intermediate. A variety of cross coupling reactions (such as those described by D. A. Evans, et al, Tetrahedron Letters, 1998, 39, 2937-2940; D. M. T. Chan, et al, Tetrahedron Lett., 1998, 39, 2933-2936; P. Y. S. Lam, et al, Tetrahedron Lett., 1998, 39, 2941-2944; Y.-C. Wong, et al, Org. Lett., 2006, 8, 5613-5616; S. A. Weissman, D. Zewge, C. Chen, J. Org. Chem., 2005, 70, 1508-1510; M. McLaughlin, Org. Lett., 2005, 7, 4875-4878; A. Cwik, Z. Hell, F. Figueras, Org. Biomol. Chem., 2005, 3, 4307-4309; R. Kuwano, M. Yokogi, Org. Lett., 2005, 7, 945-947 among others) can be performed on the halobenzamide or on the borylated benzamide (available by the procedure of T. Ishiyama et al, J. Org. Chem., 1995, 60, 7508-7510) to give the desired benzamide hedgehog inhibitor.

Scheme 1

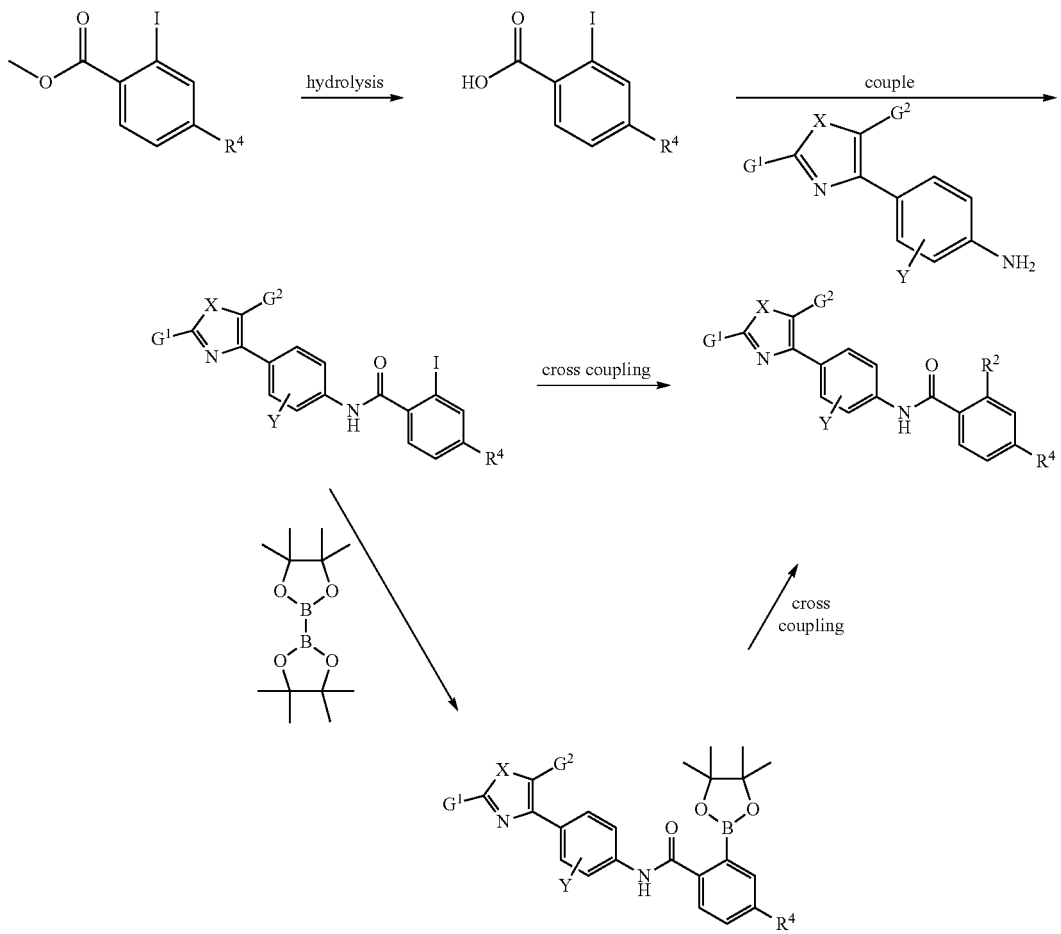

Scheme 2

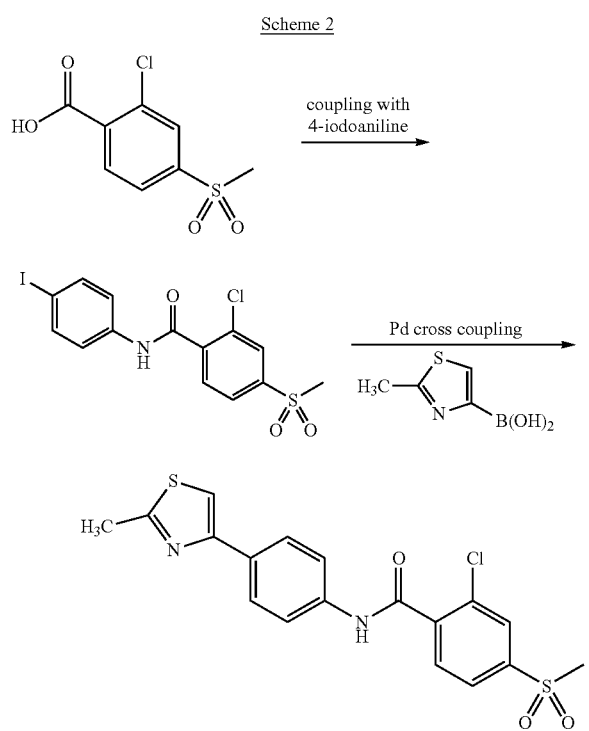

Scheme 2 illustrates the synthesis of benzamide hedgehog inhibitors. Coupling of the acid with a 4-iodoaniline gives the 4-iodobenzamide. A palladium catalyzed cross coupling reaction between thiazole boronic acid or a thiazole stannane and the 4-iodobenzamide gives the benzamide hedgehog inhibitor.

Scheme 3 illustrates the synthesis of benzamide hedgehog inhibitors. Methyl 3-iodo-4-substituted benzoate derivatives, or 3-boryl derivatives prepared by the method of T. Ishiyama et al, J. Org. Chem., 1995, 60, 7508-7510, are subjected to cross coupling reactions (such as those described by D. A. Evans, et al, Tetrahedron Letters, 1998, 39, 2937-2940; D. M. T. Chan, et al, Tetrahedron Lett., 1998, 39, 2933-2936; P. Y. S. Lam, et al, Tetrahedron Lett., 1998, 39, 2941-2944; Y.-C. Wong, et al, Org. Lett., 2006, 8, 5613-5616; S. A. Weissman, D. Zewge, C. Chen, J. Org. Chem., 2005, 70, 1508-1510; M. McLaughlin, Org. Lett., 2005, 7, 4875-4878; A. Cwik, Z. Hell, F. Figueras, Org. Biomol. Chem., 2005, 3, 4307-4309; R. Kuwano, M. Yokogi, Org. Lett., 2005, 7, 945-947 among others) to give functionalized benzoates. Hydrolysis of the ester and coupling with a functionalized aniline affords the benzamide hedgehog inhibitor.

Scheme 4

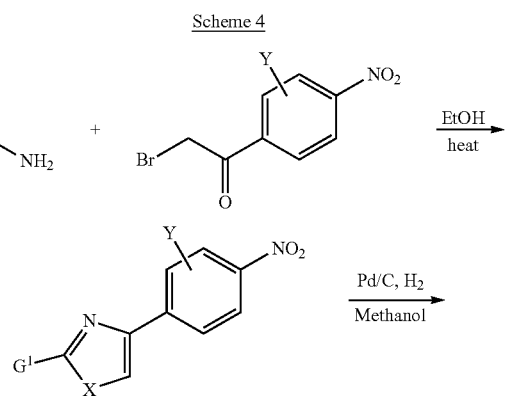

Scheme 3

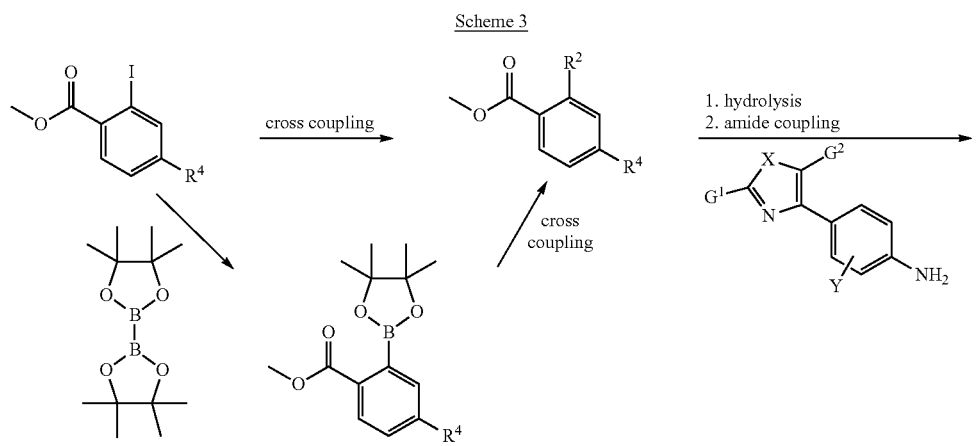

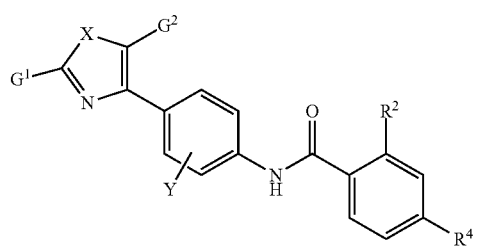

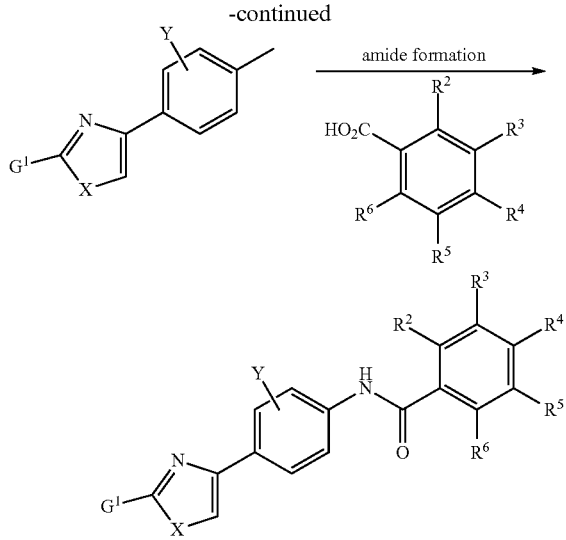

Scheme 4 illustrates the general synthesis of the aniline intermediate that can be coupled to the appropriate carboxylic acid to form the desired product.

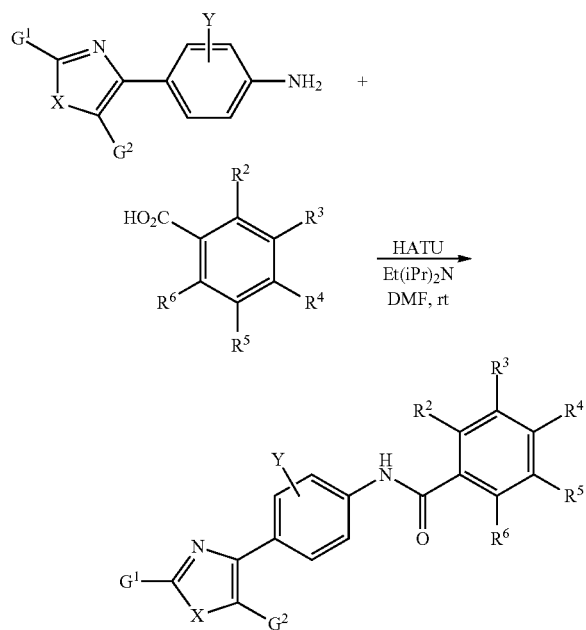

Scheme 5 further illustrates the synthesis of thiazole based Hedgehog inhibitors based on amide bond formation with hexafluorophosphate (o-(7-azabenzo-triazol-1-yl)-1,1,3,3-tetramethyluronium (HATU).

The Hedgehog Pathway

Since the late 1990's, scientists have unraveled several of the complex processes by which normal cells become cancer cells and developed a deeper knowledge of the heterogeneous nature of tumors. The mutational events which result in aberrant growth factor signaling in bulk tumor cells has led to the theory of "oncogene addiction", that ascribes cancer cell proliferation and survival to a dependence upon the activation of certain pathways or on the activity of oncogenic proteins within these pathways. More recently, researchers have found small populations of tumor cells with "stem cell" like characteristics, commonly referred to as cancer stem cells, within human primary tumor samples. These newly described cancer stem cells replicate more slowly, are more resistant to conventional chemotherapy, and their survival appears to be a major contributor to tumor re-growth following surgery and/or chemotherapy. In contrast to bulk tumor cells, cancer stem cells appear to be more reliant on embryonic pathways for their proliferation and survival traits.

The Hedgehog Pathway: Several key signaling pathways (e.g. Hedgehog, Notch, Wnt) are involved in most processes essential to the normal development of an embryo. The Hedgehog pathway was initially discovered in *Drosophila* by Dr. Eric Wieschaus and Dr. Christiane Nusslein-Volhard, and is a major regulator for cell differentiation, tissue polarity and cell proliferation. It is also becoming clear that the Hedgehog pathway may play a crucial role in tumorigenesis when reactivated in adult tissues through either mutation or other mechanisms. It is thought that the Hedgehog pathway is an important driver of tumorigenesis in at least ⅓rd of all types of cancer.

Oncogenic mutations in the Hedgehog pathway have been found in basal cell carcinoma and medulloblastoma, and Hh over expression is associated with at least pancreatic, colon, gastric, liver and prostate cancer. The estimated incidence of cancers with ligand dependent activation of Hh in the US is >200,000 cases annually and approximately 10-fold higher worldwide, see Table 2.

TABLE 2

Hh Pathway Over Expression in Solid Tumors

| Tumor | 2008 New US Cases (Deaths) | Hh Pathway Expression (% Total) | References |
|---|---|---|---|
| Colon | 108,070 (49,960) | 92,940 (86%) | Douard et al, Surgery 136, 665-670 (2006) |
| Lung | 215,020 (161,840) | 53,755* (25%-50%) | Watkins et al, Nature 422, 313-317 (2003) |
| Pancreas | 37,680 (34,290) | 18,840 (50%) | Thayer et al, Nature 425, 851-855. (2003) |
| Gastric | 21,500 (10,880) | 13,760 (64%) | Ma et al, Carcinogenesis 26, 1698-1705 (2005) |
| Hepatocellular | 21,370 (18,410) | 10,685 (50%) | Huang et al Carcinogenesis 27, 1334-1340 (2006) |
| Prostate | 186,320 (28,660) | 55,896 (30%) | Sanchez et al, PNAS 101, 12561-12566 (2004) |
| Total | 589,960 | 245,876 (41%) | |

More is becoming known about the role of cancer stem cells in the recurrence and spread of cancer. Control of the self-renewal and differentiation processes in cancer stems cells is thought to be regulated by embryonic pathways including Hedgehog. Growing evidence suggests that these pathways are deregulated in several cases, leading to abnormal cellular expansion and the formation of cancer.

Hedgehog Pathway Signaling

Human Sonic Hedgehog protein (SHh) is synthesized as a 45 kDa precursor protein that undergoes autocleavage to yield a 20 kDa fragment that is responsible for normal Hedgehog pathway signaling. At the cell surface that Hedgehog signal is thought to be relayed through the 12 transmembrane domain protein, Patched (Ptc) and the 7 transmembrane domain protein, Smoothened (Smo). In normal adult cells, Ptc serves as a negative regulatory of Smo activity. The binding of SHh to Ptc inhibits the normal inhibitory effect of Ptc on Smo allowing Smo to transduce the SHh signal across the plasma membrane. The signal cascade initiated by Smo results in the activation of Gli transcription factors that migrate to the nucleus where they control target transcription factors effecting cell growth and differentiation in embryonic cells and where uncontrolled activation in adult cells is associated with malignancies.

Methods of Inhibiting Hedgehog Signaling

One embodiment provides a method of inhibiting the Hedgehog pathway in a cell comprising contacting the cell with an inhibitory concentration of a compound of Formula (I):

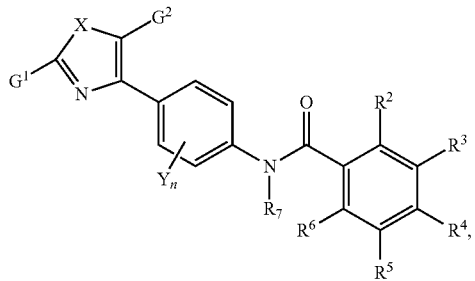

(I)

or a stereoisomer, tautomer, hydrate, solvate or pharmaceutically acceptable salt thereof, wherein:
X is —S—, —O—, —N(H)— or —N($R^1$)—;
Y is halogen, $C_1$-$C_3$ alkyl, —CN, or —$CF_3$;
n is 0, 1, 2 or 3;
$G^1$ is hydrogen, halogen, $C_1$-$C_6$ alkyl, $C_3$-$C_6$ cycloalkyl, —CN, —$CF_3$, or aryl;
$G^2$ is hydrogen, halogen, $C_1$-$C_3$ alkyl, —CN, or —$CF_3$;
$R^1$ is H or $C_1$-$C_3$ alkyl;
$R^2$ is selected from hydrogen, halogen, —CN, alkyl, —$CF_3$, aryl, —O-alkyl, —O-aryl, —O-heteroaryl, —$CH_2$-aryl, —$CH_2$-heteroaryl, —NH-aryl, —$SO_2$-aryl, $SO_2$-alkyl-NH-heteroaryl, —NH-alkyl, —$CH_2$—NH-alkyl, —$CH_2$—N(alkyl)$_2$, —$CH_2$—(N-linked heterocycle), —$CH_2$—(C-linked heterocycle), N-linked heterocycle, and C-linked heterocycle;
$R^4$ is selected from hydrogen, halogen, alkyl, alkoxy, —CN, —$CF_3$, —$SO_2$-alkyl, —$SO_2NH_2$, —$NHSO_2$-alkyl, —$NHSO_2$-aryl, —NHCO-alkyl, —NHCO-aryl, —NHCONH-alkyl, —NHCONH-aryl, —$CONH_2$, —CONH-alkyl, —CONH-aryl, —CON(alkyl)$_2$, —CON(aryl)$_2$, —$CO_2$H, and —$CO_2$alkyl;
$R^3$, $R^5$ and $R^6$ are each independently selected from hydrogen, halogen, —CN, alkyl, aryl, heteroaryl, C-linked heterocycle, —O-alkyl, —O-aryl, —O-heteroaryl, N-linked heterocycle, —NH-alkyl, —N(alkyl)$_2$, —NH-aryl, —NHheteroaryl, —$CO_2$H, —$CO_2$alkyl, —$SO_2$alkyl, —$SO_2NH_2$, —$SO_2$NHalkyl, —$SO_2$N(alkyl)$_2$, —$NHSO_2$alkyl, —$NHSO_2$aryl, —NHCONH-alkyl, —NHCON(alkyl)$_2$, —N(alkyl)CONH$_2$, —N(alkyl)CONH(alkyl), and —N(alkyl)CON(alkyl)$_2$; and
$R^7$ is H or $C_1$-$C_3$ alkyl.

Another embodiment provides the method wherein the cell is characterized by a patched loss-of-function phenotype. Another embodiment provides the method wherein the cell is characterized by a smoothened gain-of-function phenotype. Another embodiment provides the method wherein the cell is characterized by a constitutively active smoothened phenotype. Another embodiment provides the method wherein the cell is characterized by expression of Gli.

One embodiment provides a method of inhibiting the activity of smoothened protein in a cell comprising contacting the smoothened protein with an inhibitory concentration of a compound of Formula (I):

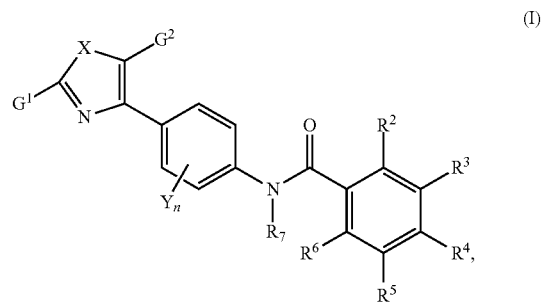

(I)

or a stereoisomer, tautomer, hydrate, solvate or pharmaceutically acceptable salt thereof, wherein:
X is —S—, —O—, —N(H)— or —N($R^1$)—;
Y is halogen, $C_1$-$C_3$ alkyl, —CN, or —$CF_3$;
n is 0, 1, 2 or 3;
$G^1$ is hydrogen, halogen, $C_1$-$C_6$ alkyl, $C_3$-$C_6$ cycloalkyl, —CN, —$CF_3$, or aryl;
$G^2$ is hydrogen, halogen, $C_1$-$C_3$ alkyl, —CN, or —$CF_3$;
$R^1$ is H or $C_1$-$C_3$ alkyl;
$R^2$ is selected from hydrogen, halogen, —CN, alkyl, —$CF_3$, aryl, —O-alkyl, —O-aryl, —O-heteroaryl, —$CH_2$-aryl, —$CH_2$-heteroaryl, —NH-aryl, —$SO_2$-aryl, $SO_2$-alkyl-NH-heteroaryl, —NH-alkyl, —$CH_2$—NH-alkyl, —$CH_2$—N(alkyl)$_2$, —$CH_2$—(N-linked heterocycle), —$CH_2$—(C-linked heterocycle), N-linked heterocycle, and C-linked heterocycle;
$R^4$ is selected from hydrogen, halogen, alkyl, alkoxy, —CN, —$CF_3$, —$SO_2$-alkyl, —$SO_2NH_2$, —$NHSO_2$-alkyl, —$NHSO_2$-aryl, —NHCO-alkyl, —NHCO-aryl, —NHCONH-alkyl, —NHCONH-aryl, —$CONH_2$, —CONH-alkyl, —CONH-aryl, —CON(alkyl)$_2$, —CON(aryl)$_2$, —$CO_2$H, and —$CO_2$alkyl;
$R^3$, $R^5$ and $R^6$ are each independently selected from hydrogen, halogen, —CN, alkyl, aryl, heteroaryl, C-linked heterocycle, —O-alkyl, —O-aryl, —O-heteroaryl, N-linked heterocycle, —NH-alkyl, —N(alkyl)$_2$, —NH-aryl, —NHheteroaryl, —$CO_2$H, —$CO_2$alkyl, —$SO_2$alkyl, —$SO_2NH_2$, —$SO_2$NHalkyl, —$SO_2$N(alkyl)$_2$, —$NHSO_2$alkyl, —$NHSO_2$aryl, —NHCONH-alkyl, —NHCON(alkyl)$_2$, —N(alkyl)CONH$_2$, —N(alkyl)CONH(alkyl), and —N(alkyl)CON(alkyl)$_2$; and
$R^7$ is H or $C_1$-$C_3$ alkyl.

Another embodiment provides the method wherein the cell is characterized by a patched loss-of-function phenotype. Another embodiment provides the method wherein the cell is characterized by a smoothened gain-of-function phenotype. Another embodiment provides the method wherein the cell is characterized by a constitutively active smoothened phenotype. Another embodiment provides the method wherein the cell is characterized by expression of Gli.

One embodiment provides a method of inhibiting the transcriptional activity of Gli transcription factor in a cell comprising contacting the cell with an inhibitory concentration of a compound of Formula (I):

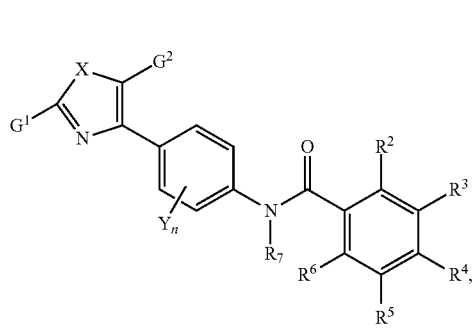

(I)

or a stereoisomer, tautomer, hydrate, solvate or pharmaceutically acceptable salt thereof, wherein:

X is —S—, —O—, —N(H)— or —N($R^1$)—;

Y is halogen, $C_1$-$C_3$ alkyl, —CN, or —$CF_3$;

n is 0, 1, 2 or 3;

$G^1$ is hydrogen, halogen, $C_1$-$C_6$ alkyl, $C_3$-$C_6$ cycloalkyl, —CN, —$CF_3$, or aryl;

$G^2$ is hydrogen, halogen, $C_1$-$C_3$ alkyl, —CN, or —$CF_3$;

$R^1$ is H or $C_1$-$C_3$ alkyl;

$R^2$ is selected from hydrogen, halogen, —CN, alkyl, —$CF_3$, aryl, —O-alkyl, —O-aryl, —O-heteroaryl, —$CH_2$-aryl, —$CH_2$-heteroaryl, —NH-aryl, —$SO_2$-aryl, $SO_2$-alkyl-NH-heteroaryl, —NH-alkyl, —$CH_2$—NH-alkyl, —$CH_2$—N(alkyl)$_2$, —$CH_2$—(N-linked heterocycle), —$CH_2$—(C-linked heterocycle), N-linked heterocycle, and C-linked heterocycle;

$R^4$ is selected from hydrogen, halogen, alkyl, alkoxy, —CN, —$CF_3$, —$SO_2$-alkyl, —$SO_2NH_2$, —$NHSO_2$-alkyl, —$NHSO_2$-aryl, —NHCO-alkyl, —NHCO-aryl, —NHCONH-alkyl, —NHCONH-aryl, —$CONH_2$, —CONH-alkyl, —CONH-aryl, —CON(alkyl)$_2$, —CON(aryl)$_2$, —$CO_2$H, and —$CO_2$alkyl;

$R^3$, $R^5$ and $R^6$ are each independently selected from hydrogen, halogen, —CN, alkyl, aryl, heteroaryl, C-linked heterocycle, —O-alkyl, —O-aryl, —O-heteroaryl, linked heterocycle, —NH-alkyl, —N(alkyl)$_2$, —NH-aryl, —NHheteroaryl, —$CO_2$H, —$CO_2$alkyl, —$SO_2$alkyl, —$SO_2NH_2$, —$SO_2$NHalkyl, —$SO_2$N(alkyl)$_2$, —$NHSO_2$alkyl, —$NHSO_2$aryl, —NHCONH-alkyl, —NHCON(alkyl)$_2$, —N(alkyl)CONH$_2$, —N(alkyl)CONH(alkyl), and —N(alkyl)CON(alkyl)$_2$; and $R^7$ is H or $C_1$-$C_3$ alkyl.

Another embodiment provides the method wherein the cell is characterized by a patched loss-of-function phenotype. Another embodiment provides the method wherein the cell is characterized by a smoothened gain-of-function phenotype. Another embodiment provides the method wherein the cell is characterized by a constitutively active smoothened phenotype. Another embodiment provides the method wherein the cell is characterized by expression of Gli.

One embodiment provides a method of inhibiting Gli-mediated gene transcription in a cell comprising contacting the cell with an inhibitory concentration of a compound of Formula (I):

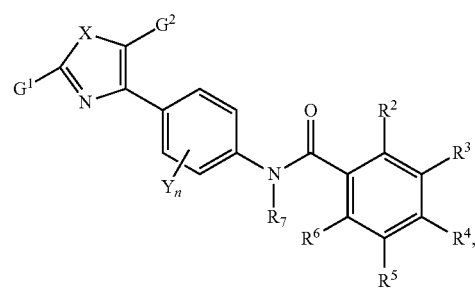

(I)

or a stereoisomer, tautomer, hydrate, solvate or pharmaceutically acceptable salt thereof, wherein:

X is —S—, —O—, —N(H)— or —N($R^1$)—;

Y is halogen, $C_1$-$C_3$ alkyl, —CN, or —$CF_3$;

n is 0, 1, 2 or 3;

$G^1$ is hydrogen, halogen, $C_1$-$C_6$ alkyl, $C_3$-$C_6$ cycloalkyl, —CN, —$CF_3$, or aryl;

$G^2$ is hydrogen, halogen, $C_1$-$C_3$ alkyl, —CN, or —$CF_3$;

$R^1$ is H or $C_1$-$C_3$ alkyl;

$R^2$ is selected from hydrogen, halogen, —CN, alkyl, —$CF_3$, aryl, —O-alkyl, —O-aryl, —O-heteroaryl, —$CH_2$-aryl, —$CH_2$-heteroaryl, —NH-aryl, —$SO_2$-aryl, $SO_2$-alkyl-NH-heteroaryl, —NH-alkyl, —$CH_2$—NH-alkyl, —$CH_2$—N(alkyl)$_2$, —$CH_2$—(N-linked heterocycle), —$CH_2$—(C-linked heterocycle), N-linked heterocycle, and C-linked heterocycle;

$R^4$ is selected from hydrogen, halogen, alkyl, alkoxy, —CN, —$CF_3$, —$SO_2$-alkyl, —$SO_2NH_2$, —$NHSO_2$-alkyl, —$NHSO_2$-aryl, —NHCO-alkyl, —NHCO-aryl, —NHCONH-alkyl, —NHCONH-aryl, —$CONH_2$, —CONH-alkyl, —CONH-aryl, —CON(alkyl)$_2$, —CON(aryl)$_2$, —$CO_2$H, and —$CO_2$alkyl;

$R^3$, $R^5$ and $R^6$ are each independently selected from hydrogen, halogen, —CN, alkyl, aryl, heteroaryl, C-linked heterocycle, —O-alkyl, —O-aryl, —O-heteroaryl, linked heterocycle, —NH-alkyl, —N(alkyl)$_2$, —NH-aryl, —NHheteroaryl, —$CO_2$H, —$CO_2$alkyl, —$SO_2$alkyl, —$SO_2NH_2$, —$SO_2$NHalkyl, —$SO_2$N(alkyl)$_2$, —$NHSO_2$alkyl, —$NHSO_2$aryl, —NHCONH-alkyl, —NHCON(alkyl)$_2$, —N(alkyl)CONH$_2$, —N(alkyl)CONH(alkyl), and —N(alkyl)CON(alkyl)$_2$; and $R^7$ is H or $C_1$-$C_3$ alkyl.

Another embodiment provides the method wherein the cell is characterized by a patched loss-of-function phenotype. Another embodiment provides the method wherein the cell is characterized by a smoothened gain-of-function phenotype. Another embodiment provides the method wherein the cell is characterized by a constitutively active smoothened phenotype. Another embodiment provides the method wherein the cell is characterized by expression of Gli.

Methods of Treatment

One embodiment provides a method of treating a human disease or disorder mediated by Hedgehog pathway comprising administering to a patient a therapeutically effective amount of a composition comprising a compound of Formula (I), or a stereoisomer, tautomer, hydrate, solvate or pharmaceutically acceptable salt thereof, wherein the compound of Formula (I) has the following structure:

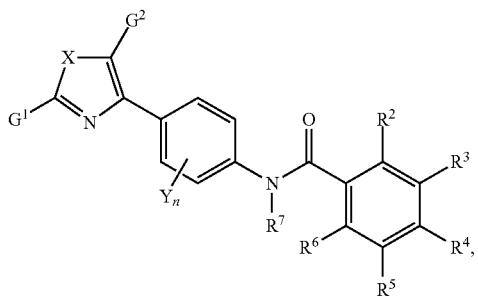

(I)

or a stereoisomer, tautomer, hydrate, solvate or pharmaceutically acceptable salt thereof, wherein:

X is —S—, —O—, —N(H)— or —N($R^1$)—;
Y is halogen, $C_1$-$C_3$ alkyl, —CN, or —$CF_3$;
n is 0, 1, 2 or 3;
$G^1$ is hydrogen, halogen, $C_1$-$C_6$ alkyl, $C_3$-$C_6$ cycloalkyl, —CN, —$CF_3$, or aryl;
$G^2$ is hydrogen, halogen, $C_1$-$C_3$ alkyl, —CN, or —$CF_3$;
$R^1$ is H or $C_1$-$C_3$ alkyl;
$R^2$ is selected from hydrogen, halogen, —CN, alkyl, —$CF_3$, aryl, —O-alkyl, —O-aryl, —O-heteroaryl, —$CH_2$-aryl, —$CH_2$-heteroaryl, —NH-aryl, —$SO_2$-aryl, $SO_2$-alkyl-NH-heteroaryl, —NH-alkyl, —$CH_2$—NH-alkyl, —$CH_2$—N(alkyl)$_2$, —$CH_2$—(N-linked heterocycle), —$CH_2$—(C-linked heterocycle), N-linked heterocycle, and C-linked heterocycle;
$R^4$ is selected from hydrogen, halogen, alkyl, alkoxy, —CN, —$CF_3$, —$SO_2$-alkyl, —$SO_2NH_2$, —$NHSO_2$-alkyl, —$NHSO_2$-aryl, —NHCO-alkyl, —NHCO-aryl, —NHCONH-alkyl, —NHCONH-aryl, —$CONH_2$, —CONH-alkyl, —CONH-aryl, —CON(alkyl)$_2$, —CON(aryl)$_2$, —$CO_2$H, and —$CO_2$alkyl;
$R^3$, $R^5$ and $R^6$ are each independently selected from hydrogen, halogen, —CN, alkyl, aryl, heteroaryl, C-linked heterocycle, —O-alkyl, —O-aryl, —O-heteroaryl, N-linked heterocycle, —NH-alkyl, —N(alkyl)$_2$, —NH-aryl, —NHheteroaryl, —$CO_2$H, —$CO_2$alkyl, —$SO_2$alkyl, —$SO_2NH_2$, —$SO_2$NHalkyl, —$SO_2$N(alkyl)$_2$, —$NHSO_2$alkyl, —$NHSO_2$aryl, —NHCONH-alkyl, —NHCON(alkyl)$_2$, —N(alkyl)$CONH_2$, —N(alkyl)CONH(alkyl), and —N(alkyl)CON(alkyl)$_2$; and
$R^7$ is H or $C_1$-$C_3$ alkyl.

Another embodiment provides the method wherein the disease or disorder is a proliferative disease. Another embodiment provides the method wherein the proliferative disease is selected from colon cancer, lung cancer, pancreatic cancer, gastric cancer, prostate cancer, and hepatocellular carcinoma. Another embodiment provides the method wherein the proliferative disease is selected from basal cell carcinoma, breast cancer, bone sarcoma, soft tissue sarcoma, chronic myeloid leukemia, acute myeloid leukemia, hematological cancer, medulloblastoma, rhabdomyosaracoma, neuroblastoma, pancreatic cancer, breast carcinoma, meningioma, glioblastoma, astrocytoma, melanoma, stomach cancer, esophageal cancer, biliary tract cancer, prostate cancer, small cell lung cancer, non-small cell lung cancer, glial cell cancer, multiple myeloma, colon cancer, neuroectodermal tumor, neuroendocrine tumor, mastocytoma and Gorlin syndrome. Another embodiment provides the method wherein the proliferative disease is basal cell carcinoma.

One embodiment provides a method of treating a veterinary disease or disorder mediated by Hedgehog pathway comprising administering to a subject a therapeutically effective amount of a composition comprising a compound of Formula (I), or a stereoisomer, tautomer, hydrate, solvate or pharmaceutically acceptable salt thereof, wherein the compound of Formula (I) has the following structure:

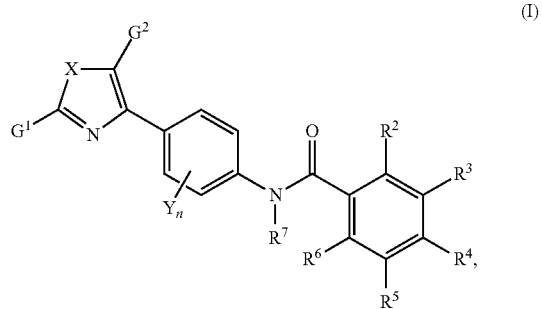

(I)

or a stereoisomer, tautomer, hydrate, solvate or pharmaceutically acceptable salt thereof, wherein:

X is —S—, —O—, —N(H)— or —N($R^1$)—;
Y is halogen, $C_1$-$C_3$ alkyl, —CN, or —$CF_3$;
n is 0, 1, 2 or 3;
$G^1$ is hydrogen, halogen, $C_1$-$C_6$ alkyl, $C_3$-$C_6$ cycloalkyl, —CN, —$CF_3$, or aryl;
$G^2$ is hydrogen, halogen, $C_1$-$C_3$ alkyl, —CN, or —$CF_3$;
$R^1$ is H or $C_1$-$C_3$ alkyl;
$R^2$ is selected from hydrogen, halogen, —CN, alkyl, —$CF_3$, aryl, —O-alkyl, —O-aryl, —O-heteroaryl, —$CH_2$-aryl, —$CH_2$-heteroaryl, —NH-aryl, —$SO_2$-aryl, $SO_2$-alkyl-NH-heteroaryl, —NH-alkyl, —$CH_2$—NH-alkyl, —$CH_2$—N(alkyl)$_2$, —$CH_2$—(N-linked heterocycle), —$CH_2$—(C-linked heterocycle), N-linked heterocycle, and C-linked heterocycle;
$R^4$ is selected from hydrogen, halogen, alkyl, alkoxy, —CN, —$CF_3$, —$SO_2$-alkyl, —$SO_2NH_2$, —$NHSO_2$-alkyl, —$NHSO_2$-aryl, —NHCO-alkyl, —NHCO-aryl, —NHCONH-alkyl, —NHCONH-aryl, —$CONH_2$, —CONH-alkyl, —CONH-aryl, —CON(alkyl)$_2$, —CON(aryl)$_2$, —$CO_2$H, and —$CO_2$alkyl;
$R^3$, $R^5$ and $R^6$ are each independently selected from hydrogen, halogen, —CN, alkyl, aryl, heteroaryl, C-linked heterocycle, —O-alkyl, —O-aryl, —O-heteroaryl, N-linked heterocycle, —NH-alkyl, —N(alkyl)$_2$, —NH-aryl, —NHheteroaryl, —$CO_2$H, —$CO_2$alkyl, —$SO_2$alkyl, —$SO_2NH_2$, —$SO_2$NHalkyl, —$SO_2$N(alkyl)$_2$, —$NHSO_2$alkyl, —$NHSO_2$aryl, —NHCONH-alkyl, —NHCON(alkyl)$_2$, —N(alkyl)$CONH_2$, —N(alkyl)CONH(alkyl), and —N(alkyl)CON(alkyl)$_2$; and
$R^7$ is H or $C_1$-$C_3$ alkyl.

Another embodiment provides a method of treating a veterinary disease or disorder wherein the disease or disorder is a proliferative disease selected from mast cell tumors or osteosarcoma.

EXAMPLES

I. Chemical Synthesis

Synthesis of Intermediates

Intermediate 1: 3-chloro-(2-methylthiazol-4-yl)aniline

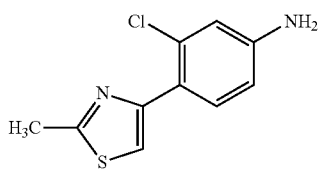

Step 1: 3-chloro-4-(bromoacetyl)nitrobenzene

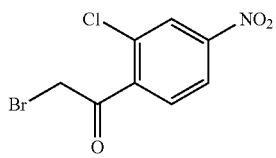 [SMILES: O=C(CBr)c1ccc([N+](=O)[O-])cc1Cl]

A stirring solution of 3-chloro-4-acetyl-nitrobenzene (1.685 g, 8.44 mmol) (prepared as described in *J. Med. Chem.* 2005, 48, 6066) and paratoluenesulfonic acid (2.41 g, 12.66 mmol) in acetonitrile (100 mL) was treated with NBS (1.503 g, 8.44 mmol) and heated to 80° C. for 23 h. Another gram of NBS was added after 21 h. The reaction was cooled to room temperature and concentrated in vacuo. The residue was taken up in EtOAc and the organic layer was washed with water (2×), brine, and dried over MgSO$_4$, filtered, and adsorbed on silica. Purification on silica by flash chromatography using a gradient of 0-40% EtOAc/hexane yielded 554 mg of the titled compound as a waxy solid (23% yield): $^1$H NMR (400 MHz, DMSO-d6) δ 4.95 (s, 2H), 8.09 (d, 1H), 8.35 (dd, 1H), 8.44 (d, 1H).

Step 2: 3-chloro-(2-methylthiazol-4-yl)aniline

A solution of 3-chloro-4-(bromoacetyl)nitrobenzene (546 mg, 1.96 mmol) and thioacetamide (162 mg, 2.15 mmol) in absolute EtOH (8 mL) was stirred at 85° C. for 1 h and cooled to room temperature. Solvent was evaporated in vacuo. A suspension of SnCl$_2$.2H$_2$O (1.46 g, 6.47 mmol) and conc. HCl (2 mL) in absolute EtOH (12 mL) was heated to reflux and the resulting clear solution was added to the residue. The reaction mixture was stirred at reflux for 1 h, cooled to room temperature and poured into a solution of KOH (4.4 g) in water (50 mL) at 0° C. The aqueous layer was extracted with EtOAc (3×) and the combined organics were dried over MgSO$_4$, filtered, and concentrated in vacuo to give 438 mg of the titled product as a dark yellow oil (quant. yield): $^1$H NMR (400 MHz, DMSO-d6) δ 2.70 (s, 3H), 5.61 (broad s, 2H), 6.59 (dd, 1H), 6.69 (d, 1H), 7.58 (d, 1H), 7.62 (s, 1H); [M+H$^+$]$^+$ m/z 225.

Intermediate 2: 2-chloro-(4-methylsulfonyl)-N-(4-(2-ethoxycarbonylthiazol-4-yl)phenyl)benzamide and 2-chloro-(4-methylsulfonyl)-N-(4-(thiazol-4-yl)phenyl)benzamide

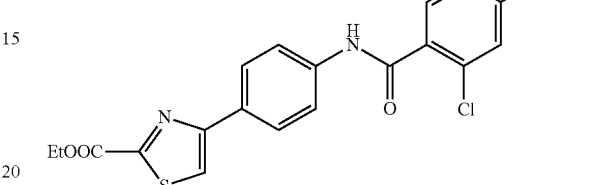

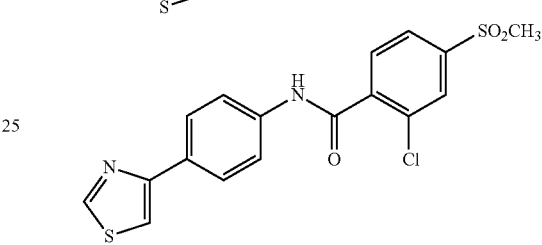

Step 1: (2-ethoxycarbonylthiazol-4-yl)nitrobenzene

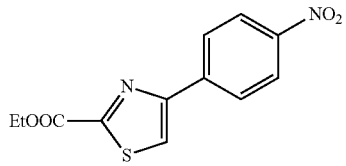 [SMILES: CCOC(=O)c1nc(-c2ccc([N+](=O)[O-])cc2)cs1]

A solution of 4-bromoacetyl-nitrobenzene (1.8 g, 7.37 mmol) and ethyl thiooxamate (982 mg, 7.37 mmol) in absolute EtOH (20 mL) was stirred at 80° C. for 19 h, cooled to room temperature, and poured into saturated aqueous sodium carbonate. The resulting precipitate was filtered, washed with water and dried in vacuo to give 1.826 g of the titled product as a yellow solid (89% yield): $^1$H NMR (400 MHz, DMSO-d6) δ 1.40 (t, 3H), 4.46 (q, 2H), 8.32 (d, 2H), 8.38 (d, 2H), 8.89 (s, 1H).

Step 2: (2-ethoxycarbonylthiazol-4-yl)aniline and 4-(4-aminophenyl)thiazole

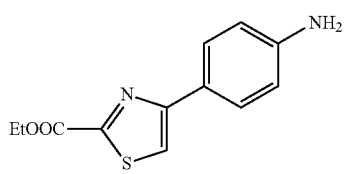

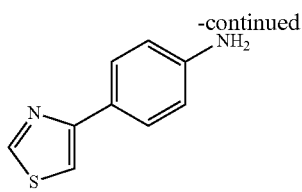

A suspension of SnCl$_2$.2H$_2$O (4.01 g, 17.79 mmol) and conc. HCl (5.4 mL) in absolute EtOH (25 mL) was heated to reflux and the resulting clear solution was added to (2-ethoxy-carbonylthiazol-4-yl)nitrobenzene (1.5 g, 5.39 mmol). The reaction mixture was stirred at reflux for 2 h, cooled to room temperature and poured into a solution of KOH (12.1 g) in water (140 mL) at 0° C. The aqueous layer was extracted with EtOAc (3×) and the combined organics were dried over MgSO$_4$, filtered through a pad of silica, and concentrated in vacuo to give 540 mg of a (2:1) mixture of titled products as a dark yellow oil.

Step 3: 2-chloro-(4-methylsulfonyl)-N-(4-(2-ethoxy-carbonylthiazol-4-yl)phenyl)benzamide and 2-chloro-(4-methylsulfonyl)-N-(4-(thiazol-4-yl)phenyl)benzamide (1:1 mixture)

To a stirring solution of (2-ethoxycarbonylthiazol-4-yl) aniline/4-(4-aminophenyl)thiazole mixture (540 mg, 2.17 mmol) in DCM (10 mL) was added 2-chloro-4-methylsulfonylbenzoic acid (510 mg, 2.17 mmol) and DMAP (27 mg, 0.217 mmol). The reaction mixture was stirred for 5 min. then EDCI.HCl (500 mg, 2.60 mmol) was added. After stirring for 17 h, the reaction mixture was partitioned between water and EtOAc. The organic layer was separated, washed with water (2×) and brine, dried over MgSO$_4$, filtered, and adsorbed on silica. Purification on silica by flash chromatography using a gradient of 10-70% EtOAc/hexane yielded 520 mg of a (1:1) mixture of titled compounds as a yellow solid.
2-chloro-(4-methylsulfonyl)-N-(4-(2-ethoxycarbonylthiazol-4-yl)phenyl)benzamide: [M+H$^+$]$^+$ m/z 465.
2-chloro-(4-methylsulfonyl)-N-(4-(thiazol-4-yl)phenyl)benzamide: [M+H$^+$]$^+$ m/z 393.

Intermediate 3:
4-methoxy-2-(morpholinomethyl)benzoic acid

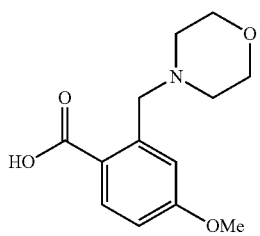 [SMILES: COc1ccc(C(=O)O)c(CN2CCOCC2)c1]

Step 1: Methyl 2-(bromomethyl)-4-methoxybenzoate

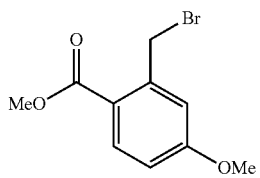 [SMILES: COC(=O)c1ccc(OC)cc1CBr]

To a solution of methyl 4-methoxy-2-methylbenzoate (1 g, 5.6 mmol) in CCl$_4$ (25 mL) was added dropwise N-bromo-succinimide (1.1 g, 6.2 mmol) previously dissolved in CCl$_4$ (5 mL) and a catalytic amount of benzoyl peroxide. The mixture was refluxed for 2 hours, cooled to room temperature and poured onto iced water. The aqueous mixture was extracted with DCM (3×), and the combined organics were dried over MgSO$_4$, filtered, and concentrated in vacuo to provide 2.1 g of the titled product as light yellow solid (~100% yield): [M+H$^+$] m/z 260.

Step 2: methyl 4-methoxy-2-(morpholinomethyl)benzoate

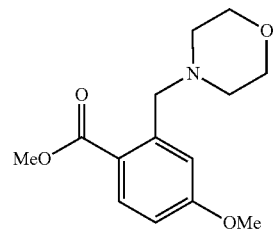 [SMILES: COC(=O)c1ccc(OC)cc1CN1CCOCC1]

To a solution of methyl 2-(bromomethyl)-4-methoxybenzoate (960 mg, 3.7 mmol) in DCM (18.5 mL) was added morpholine (0.68 mL, 7.8 mmol). The reaction mixture was stirred at room temperature overnight and poured onto iced water. The aqueous mixture was extracted with DCM (3×), and the combined organics were dried over MgSO$_4$, filtered, and concentrated in vacuo to provide a yellow oil. The crude material was purified by flash chromatography on silica using a gradient of EtOAc in hexane (0 to 50%) as eluant. The tittle product was obtained as a clear oil (490 mg, 50%)

Step 3: 4-methoxy-2-(morpholinomethyl)benzoic acid

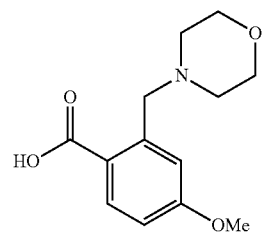

To a solution of methyl 2-(bromomethyl)-4-methoxybenzoate (160 mg, 0.6 mmol) was dissolved in EtOH (5 mL) and a aqueous solution of sodium hydroxide was added (1N, 6.1 mL, 6.1 mmol). The resulting mixture was stirred at room temperature over night and concentrated under reduced pressure to produce a white solid. The compound was used as is for the next step. LC-MS (M+H): 252.09

Intermediate 4: 4-(2-methyloxazol-4-yl)aniline

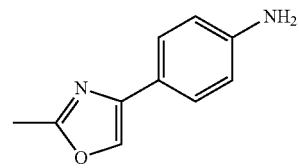

2-methyl-4-(4-nitrophenyl)oxazole (J. Heterocyclic Chemistry, 1981, 885)(1.12 g, 5.48 mmol) was added to a refluxing solution of SnCl$_2$.2H$_2$O (6.33 g, 28.1 mmol), conc HCL (10 mL) and EtOH (20 mL). The reaction is stirred for 30 min then cooled to room temperature and poured into a solution of 24 g of KOH in 100 mL of water. The resulting mixture was cooled in an ice bath and stirred for an additional 30 min. The product was collected by filtration as a yellow solid (1.35 g, 83%). LC-MS (M+H): 191

General Procedures:

Method A

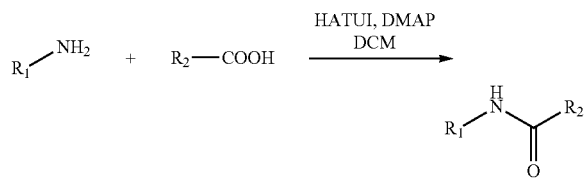

Example 1

2,4-dichloro-N-(4-(2-methylthiazol-4-yl)phenyl)benzamide

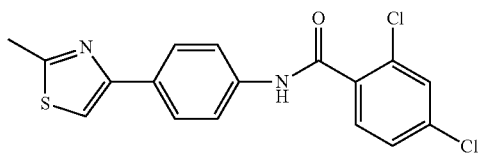

To a solution of 4-(2-methylthiazol-4-yl)aniline (0.05 g, 0.26 mmol) and 2,4-dichlorobenzoic acid (0.05 g, 0.26 mmol) in dimethylformamide (20 mL) and diisopropylethylamine (0.067 g, 0.09 mL, 0.52 mmol) at room temperature was added HATU (0.148 g, 0.39 mmol) in one portion. The reaction was stirred at room temperature for 4 hours, then poured in to water (200 mL) and stirred for 20 minutes. The product (0.094 g, 100%) as a light yellow solid was collected via filtration. LC-MS (M+H): 364. $^1$H NMR (400 MHz, dmso-$d_6$): 10.67 (s, 1H), 7.95 (d, 2H), 7.87 (s, 1H), 7.80-7.77 (m, 3H), 7.69-7.58 (m, 2H), 2.74 (s, 3H).

Examples 2, 3, 4, 5 and 6 were prepared according to the Method A (see table 3)

Method B

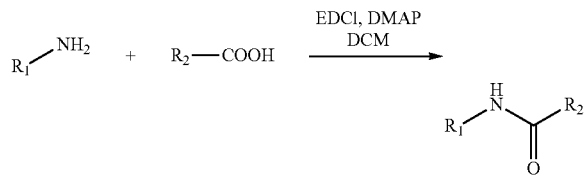

Example 7

2-chloro-N-(3-chloro-4-(2-methylthiazol-4-yl)phenyl)-4-(methylsulfonyl)benzamide

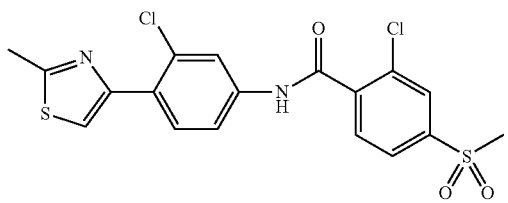

To a stirring mixture of 3-chloro-(2-methylthiazol-4-yl)aniline (435 mg, 1.936 mmol), 2-chloro-4-methylsulfonylbenzoic acid (545 mg, 2.32 mmol) and DMAP (237 mg, 1.936 mmol) in DCM (8 mL) was added EDCI.HCl (445 mg, 2.32 mmol). After stirring overnight, the reaction mixture was partitioned between water and EtOAc. The organic layer was separated, washed with saturated aqueous sodium bicarbonate, saturated aqueous ammonium chloride and brine, dried over MgSO$_4$, filtered, and adsorbed on silica. Purification on silica by flash chromatography using a gradient of 20-80% EtOAc/hexane yielded 543 mg of the titled compound as a light yellow solid (63% yield). Alternatively, some compounds were purified by precipitation: The DCM was removed from the reaction mixture and DMF and 0.1M NH$_4$Cl (compound 18) or 1N HCl (compounds 14, 15, 16, 17) were added which caused the products to crash out of solution.

Examples 8, 14, 15, 16, 17, and 18 were prepared according to the Method B (see table 3)

Method C

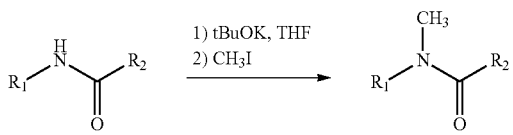

Example 9

2-chloro-N-methyl-4-(methylsulfonyl)-N-(4-(2-methylthiazol-4-yl)phenyl)benzamide

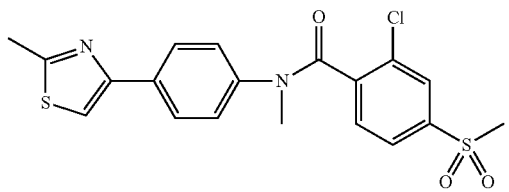

To a stirring solution of 2-chloro-4-(methylsulfonyl)-N-(4-(2-methylthiazol-4-yl)phenyl)benzamide (50 mg, 0.123 mmol) in THF (1 mL) under nitrogen atmosphere was added 1M solution of tBuOK in tBuOH (0.14 mL) dropwise. After stirring for 15 min, CH$_3$I (0.009 mL, 0.14 mmol) was added and the reaction mixture was stirred at 60° C. for 1 h, before partitioning between water and EtOAc. The organic layer was isolated, washed with brine, and adsorbed on silica. Purification on silica by flash chromatography using a gradient of 40-100% EtOAc/hexane yielded 40 mg of the titled compound as an off-white solid (77% yield).

Method D

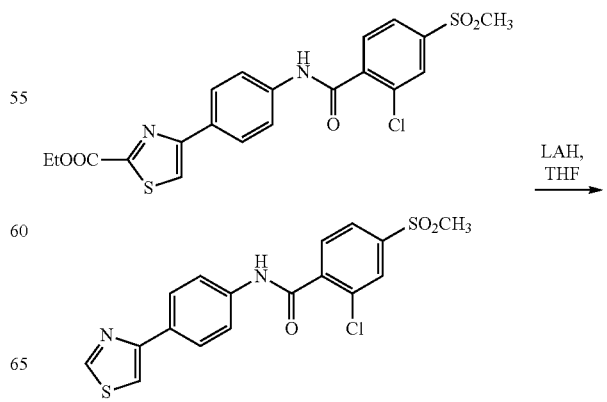

Example 10

2-chloro-N-(4-(thiazol-4-yl)phenyl)benzamide

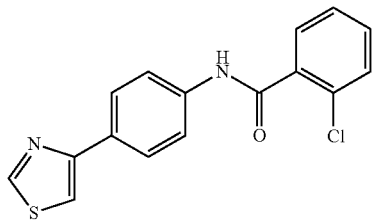 [SMILES: O=C(Nc1ccc(-c2cscn2)cc1)c1ccccc1Cl]

A stirring suspension of 2-chloro-(4-methylsulfonyl)-N-(4-(2-ethoxycarbonylthiazol-4-yl)phenyl)benzamide and 2-chloro-(4-methylsulfonyl)-N-(4-(thiazol-4-yl)phenyl)benzamide (1:1 mixture) (100 mg, 0.215 mmol) in THF (1 mL) under nitrogen atmosphere was cooled to 0° C. and treated with 1M LAH solution in THF (0.32 mL) dropwise. The reaction mixture was stirred at 0° C. for 1 h, quenched with 0.64 mL of 1N aqueous HCl, and partitioned between water and EtOAc. The aqueous layer was isolated, extracted with EtOAc (2×), and the combined organics were dried over MgSO$_4$, filtered and adsorbed on silica. Purification on silica by flash chromatography using a gradient of 0-80% EtOAc/hexane yielded 12 mg of the titled compound as a yellow solid (18% yield).

Example 11 and 12

2-chloro-N-(4-(2-(hydroxymethyl)thiazol-4-yl)phenyl)-4-(methylsulfonyl)benzamide and 2-chloro-N-(4-(2-(2-hydroxypropan-2-yl)thiazol-4-yl)phenyl)-4-(methylsulfonyl)benzamide

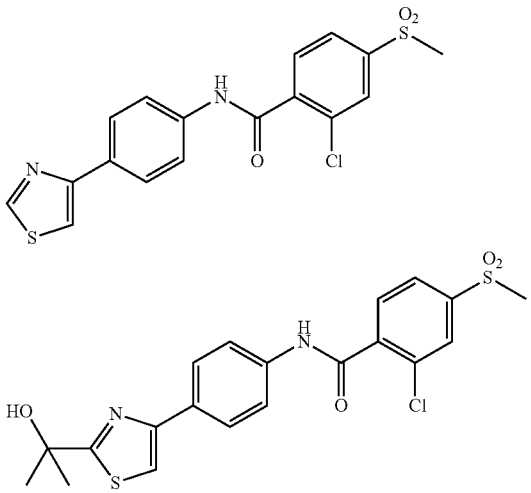

A stirring suspension of 2-chloro-(4-methylsulfonyl)-N-(4-(2-ethoxycarbonylthiazol-4-yl)phenyl)benzamide and 2-chloro-(4-methylsulfonyl)-N-(4-(thiazol-4-yl)phenyl)benzamide (1:1 mixture) (100 mg, 0.215 mmol) in THF (1 mL) under nitrogen atmosphere was cooled to 0° C. and treated with 1.4M CH$_3$MgBr solution in toluene/THF (0.77 mL) dropwise. The reaction mixture was stirred at 0° C. for 1 h, quenched with 1 mL of 1N aqueous HCl, and partitioned between water and EtOAc. The aqueous layer was isolated, extracted with EtOAc (2×), and the combined organics were dried over MgSO$_4$, filtered and adsorbed on silica. Purification on silica by flash chromatography using a gradient of 0-20% CH$_3$CN/DCM yielded 38 mg of 2-chloro-N-(4-(2-(hydroxymethyl)thiazol-4-yl)phenyl)-4-(methylsulfonyl)benzamide as a white solid and 34 mg of -chloro-N-(4-(2-(2-hydroxypropan-2-yl)thiazol-4-yl)phenyl)-4-(methylsulfonyl)benzamide as an off-white solid.

Method E

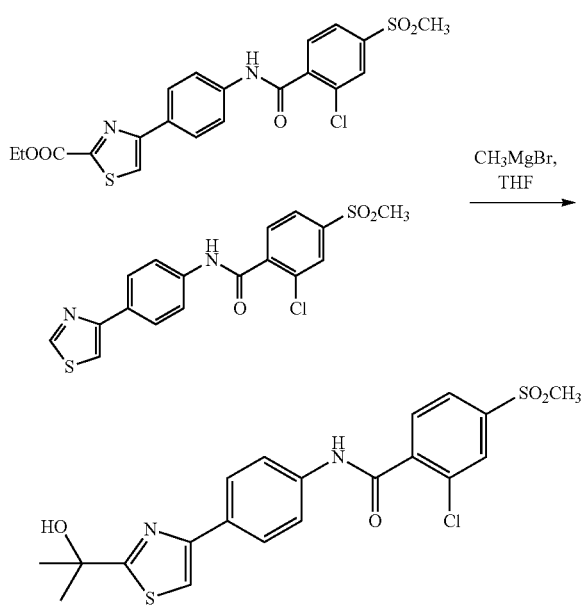

Method F

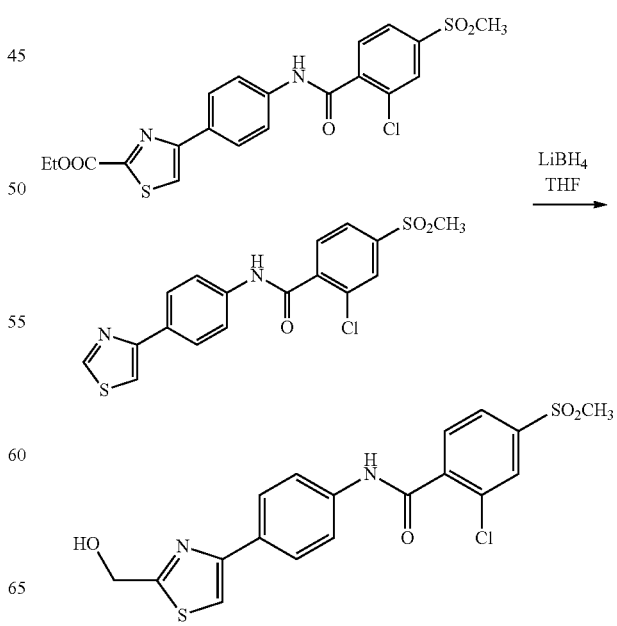

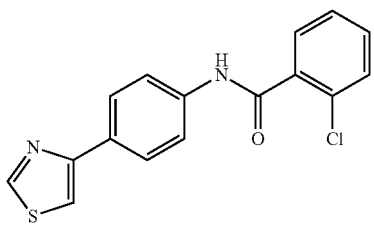

Example 13

2-chloro-N-(4-(2-(hydroxymethyl)thiazol-4-yl)phenyl)-4-(methylsulfonyl)benzamide

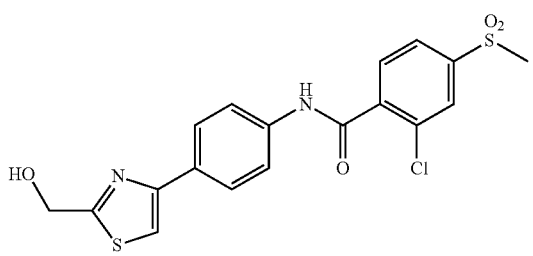 [SMILES: CS(=O)(=O)c1ccc(C(=O)Nc2ccc(-c3csc(CO)n3)cc2)c(Cl)c1]

A stirring suspension of 2-chloro-(4-methylsulfonyl)-N-(4-(2-ethoxycarbonylthiazol-4-yl)phenyl)benzamide and 2-chloro-(4-methylsulfonyl)-N-(4-(thiazol-4-yl)phenyl)benzamide (1:1 mixture) (50 mg, 0.107 mmol) in THF (1 mL) under nitrogen atmosphere was treated with 2M LiBH$_4$ solution in THF (0.11 mL) dropwise. The reaction mixture was stirred at 60° C. for 1 h, quenched with water, and partitioned between water and EtOAc. The aqueous layer was isolated, extracted with EtOAc (3×), and the combined organics were dried over MgSO$_4$, filtered and adsorbed on silica. Purification on silica by flash chromatography using a gradient of 0-20% CH$_3$CN/DCM then 10% MeOH/DCM yielded 5 mg of the titled product as a white solid.

Compounds in Table 3 were prepared using the indicated method.

TABLE 3

| Example | Structure | Synthesis Method | $^1$H NMR (400 MHz), δ (ppm) | Activity Ranking | [M + H]$^+$ |
|---|---|---|---|---|---|
| 1 | 2,4-dichloro-N-(4-(2-methylthiazol-4-yl)phenyl)benzamide | A | (DMSO-d6) 10.67 (s, 1H), 7.95 (d, 2H), 7.87 (s, 1H), 7.80-7.77 (m, 3H), 7.69-7.58 (m, 2H), 2.74 (s, 3H). | A | 365 |
| 2 | 3,4,5-trimethoxy-N-(4-(2-methylthiazol-4-yl)phenyl)benzamide | A | (DMSO-d6) 10.23 (s, 1H), 7.96 (d, 2H), 7.87-7.80 (m, 3H), 7.32 (s, 2H), 3.90 (s, 6H), 3.75 (s, 3H), 2.74 (s, 3H). | C | 385 |
| 3 | 4-methoxy-N-(4-(2-methylthiazol-4-yl)phenyl)benzamide | A | (DMSO-d6) 10.21 (s, 1H), 8.00 (d, 2H), 7.93 (d, 2H), 7.88-7.87 (m, 3H), 7.09 (d, 2H), 3.87 (s, 3H), 2.73 (s, 3H). | A | 326 |
| 4 | 2-chloro-4-(methylsulfonyl)-N-(4-(2-methylthiazol-4-yl)phenyl)benzamide | A | (DMSO-d6) 10.82 (s, 1H), 8.17-8.16 (m, 1H), 8.05-7.90 (m, 5H), 7.79 (d, 2H), 3.38 (s, 3H), 2.75 (s, 3H). | A | 407 |

TABLE 3-continued

| Example | Structure | Synthesis Method | ¹H NMR (400 MHz), δ (ppm) | Activity Ranking | [M + H]⁺ |
|---|---|---|---|---|---|
| 5 | 4-methoxy-N-(4-(2-methylthiazol-4-yl)pheny)-2-(morpholinomethyl)benzamide | A | (DMSO-d6) 11.71 (s, 1H), 8.08 (d, 1H), 7.92 (d, 2H), 7.76 (d, 2H), 7.29 (s, 1H), 7.01 (d, 1H), 6.76 (s, 1H), 3.89 (s, 3H), 3.83 (s, 4H), 2.83 (s, 3H), 2.62 (s, 4H) | A | 424 |
| 6 | 2-chloro-N-(4-(2-methyloxazol-4-yl)phenyl)-4-(methylsulfonyl)benzamide | A | (DMSO-d6) 10.81 (s, 1H), 8.45 (a, 1H), 8.15 (s, 1H), 8.04 (d, 1H), 8.02 (d, 1H), 7.77 (m, 4H), 2.49 (s, 3H) | B | 390 |
| 7 | 2-chloro-N-(3-chloro-4-(2-methylthiazol-4-yl)phenyl)-4-(methylsulfonyl)benzamide | B | (DMSO-d6) 2.75 (s, 3H), 3.38 (s, 3H), 7.69 (dd, 1H), 7.95 (m, 3H), 8.04 (m, 2H), 8.17 (d, 1H), 11.0 (s, 1H) | C | 441 |
| 8 | 2-chloro-4-methoxy-N-(4-(2-methylthiazol-4-yl)phenyl)benzamide | B | (DMSO-d6) 2.74 (s, 3H), 3.86 (s, 3H), 7.06 (dd, 1H), 7.17 (d, 1H), 7.58 (d, 1H), 7.79 (d, 2H), 7.87 (s, 1H), 7.93 (d, 2H), 10.5 (s, 1H) | A | 359 |
| 9 | 2-chloro-N-methyl-4-(methylsulfonyl)-N-(4-(2-methylthiazol-4-yl)phenyl)benzamide | C | (DMSO-d6) 2.69 (s, 3H), 3.25 (s, 3H), 3.46 (s, 3H), 7.34 (d, 2H), 7.72 (d, 1H), 7.76 (dd, 1H), 7.83 (d, 2H), 7.88 (d, 1H), 7.94 (s, 1H) | D | 421 |

TABLE 3-continued

| Example | Structure | Synthesis Method | ¹H NMR (400 MHz), δ (ppm) | Activity Ranking | [M + H]⁺ |
|---|---|---|---|---|---|
| 10 | 2-chloro-N-(4-(thiazol-4-yl)phenyl) benzamide | D | (DMSO-d6) 7.49-7.55 (m, 2H), 7.63 (m, 2H), 7.83 (d, 2H), 8.01 (d, 2H), 8.12 (d, 1H), 9.21 (d, 1H), 10.6 (s, 1H) | B | 315 |
| 11 | 2-chloro-4-(methylsulfonyl)-N-(4-(thiazol-4-yl)phenyl)benzamide | E | (DMSO-d6) 3.38 (s, 3H), 7.81 (d, 2H), 7.94 (d, 1H), 8.03 (m, 3H), 8.16 (dd, 2H), 9.22 (d, 1H), 10.8 (s, 1H) | B | 393 |
| 12 | 2-chloro-N-(4-(2-(2-hydroxypropan-2-yl) thiazol-4-yl)phenyl)-4-(methylsulfonyl)benzamide | E | (DMSO-d6) 1.59 (s, 6H), 3.38 (s, 3H), 6.04 (s, 1H), 7.79 (d, 2H), 7.91-7.97 (m, 4H), 8.02 (dd, 1H), 8.15 (d, 1H), 10.8 (s, 1H) | B | 451 |
| 13 | 2-chloro-N-(4-(2-(hydroxymethyl)thiazol-4-yl) phenyl)-4-(methylsulfonyl)benzamide | F | (DMSO-d6) 3.38 (s, 3H), 4.82 (broad s, 2H), 6.15 (broad s, 1H), 7.79 (d, 2H), 7.92-8.02 (m, 5H), 8.16 (d, 1H), 10.8 (s, 1H) | C | 423 |
| 14 | 2-chloro-N-(4-(2-methylthiazol-4-yl)phenyl)benzamide | B | (DMSO-d6) 10.63 (s, 1), 7.96 (d, 2H), 7.87 (s, 1H), 7.64 (d, 2H), 7.56-7.49 (m, 4H), 2.74 (s, 3H) | A | 329 |

TABLE 3-continued

| Example | Structure | Synthesis Method | ¹H NMR (400 MHz), δ (ppm) | Activity Ranking | [M + H]⁺ |
|---|---|---|---|---|---|
| 15 | 2-(methylsulfonyl)-N-(4-(2-methylthiazol-4-yl)phenyl)benzamide | B | (DMSO-d6) 10.77 (s, 1H), 8.06 (d, 1H), 7.96 (d, 2H), 7.81 (m, 2H), 7.79-7.76 (m, 4H), 3.42 (s, 3H), 2.74 (s, 3H) | D | 373 |
| 16 | 4-methoxy-2-methyl-N-(4-(2-methylthiazol-4-yl)phenyl)benzamide | B | (DMSO-d6) 10.27 (s, 1H), 7.93 (d, 2H), 7.85 (s, 1H), 7.83 (d, 2H), 7.50 (d, 1H), 6.90 (m, 2H), 3.82 (s, 3H), 2.74 (s, 3H), 2.43 (s, 3H) | A | 339 |
| 17 | 2-fluoro-4-methoxy-N-(4-(2-methylthiazol-4-yl)phenyl)benzamide | B | (DMSO-d6) 10.30 (s, 1H), 7.94 (d, 2H), 7.87 (s, 1H), 7.81 (d, 2H), 7.68 (t, 1H), 6.95 (d, 1H), 6.92 (d, 1H), 3.87 (s, 3H), 2.74 (s, 3H) | A | 343 |
| 18 | 4-cyano-N-(4-(2-methylthiazol-4-yl)phenyl)benzamide | B | (DMSO-d6) 10.6 (s, 1H), 8.16 (d, 2H), 8.08 (d, 2H), 7.98 (d, 2H), 7.89-7.86 (m, 3H), 2.74 (s, 3H) | B | 320 |

Note:
Activity Ranking refers to the percent activity compared to control alkaline phosphatase activity at 500 nM as determined by modified method A. Rank: = 0 to 25% control activity; B = 26 to 50% control activity; C = 51 to 75% control activity; and D = 76 to 100% control activity.

Example 19

4-methoxy-2-((4-methylpiperazin-1-yl)methyl)-N-(4-(2-methylthiazol-4-yl)phenyl)benzamide

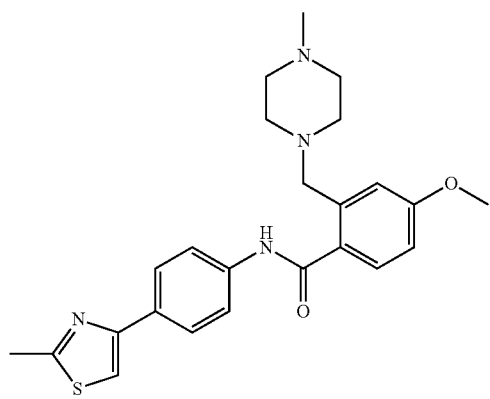

The example 19 is synthesized using the chemistry described for example 5 according to the following synthetic scheme.

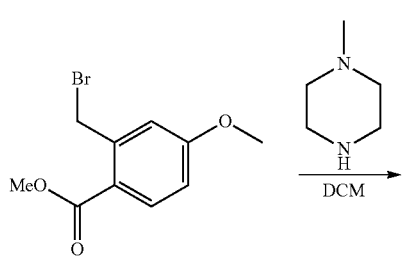

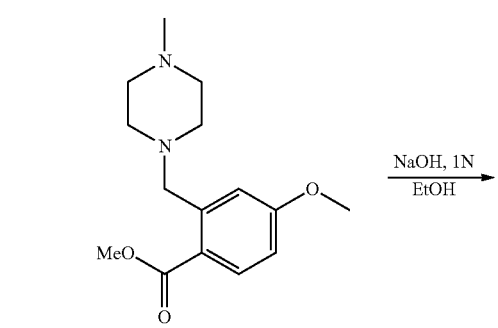

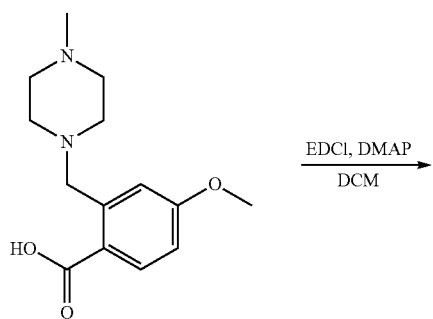

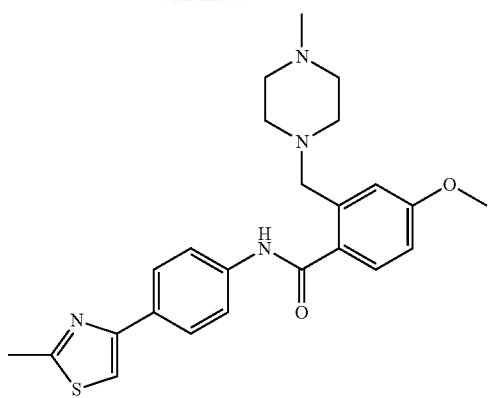

Example 20

2-((2-hydroxyethylamino)methyl)-4-methoxy-N-(4-(2-methylthiazol-4-yl)phenyl)benzamide

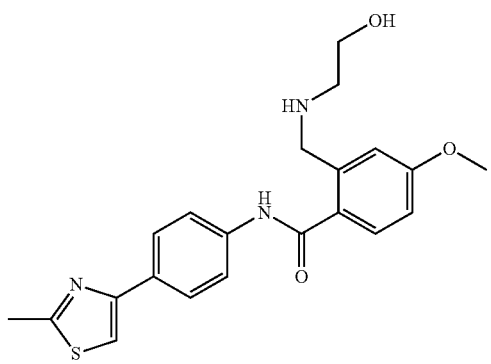

The example 20 is synthesized using the chemistry described for example 5 according to the following synthetic scheme.

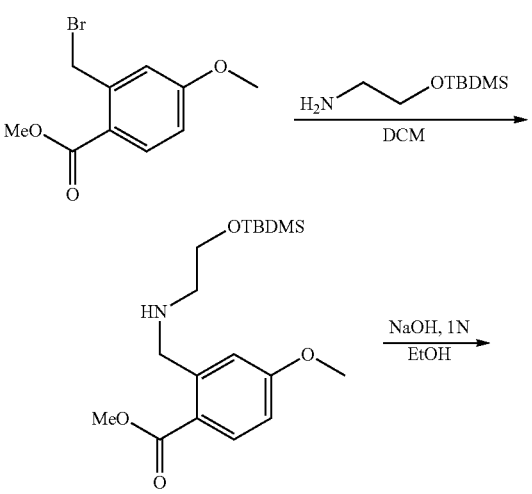

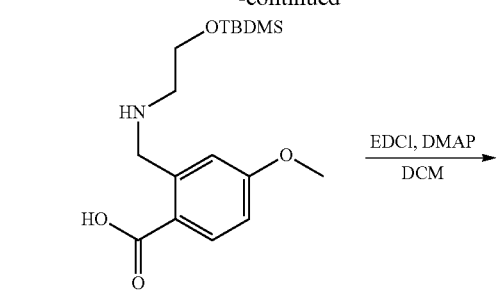

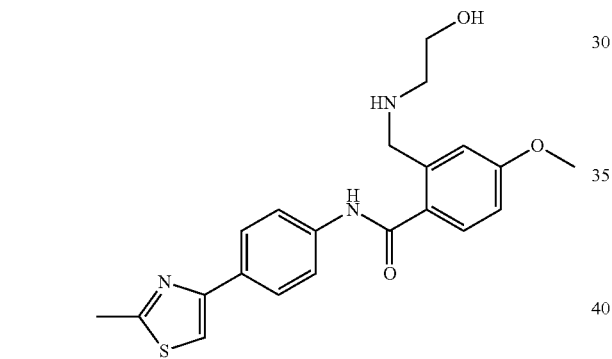

The following compound are synthesized using 4-(2-methylthiazol-4-yl)aniline (commercially available) coupled with the appropriate carboxylic acid using method A or B.

example 21

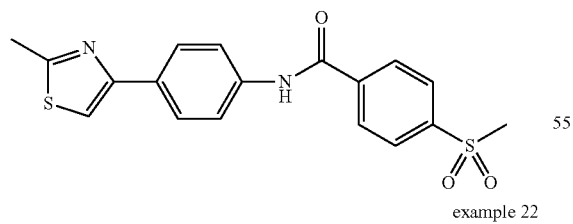

example 22

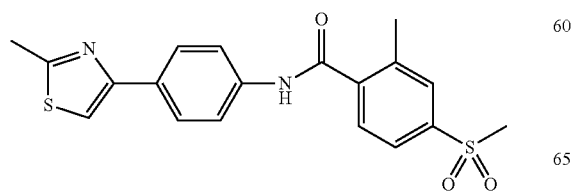

example 23

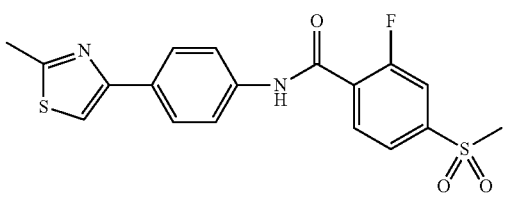

example 24

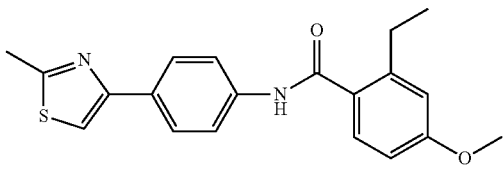

example 25

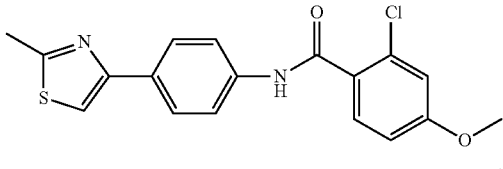

example 26

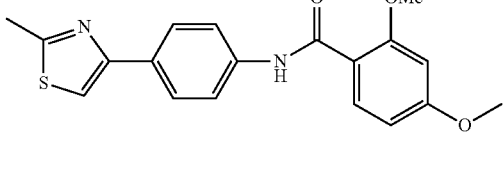

The following compounds are synthesized using intermediate 1 coupled with the appropriate carboxylic acid using method A or B.

example 27

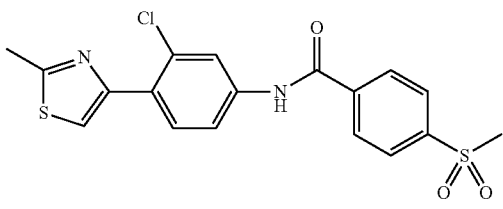

example 28

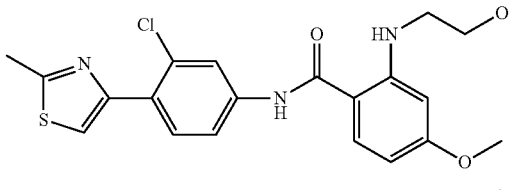

example 29

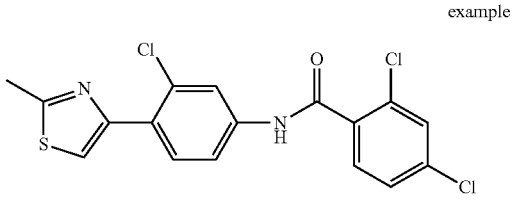

example 30
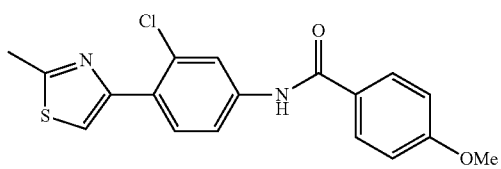
example 31
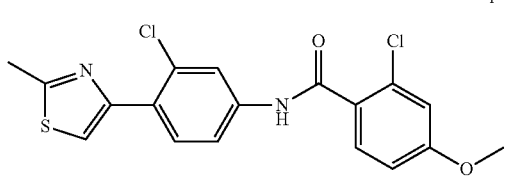
example 32
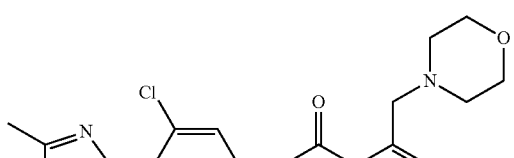
example 33
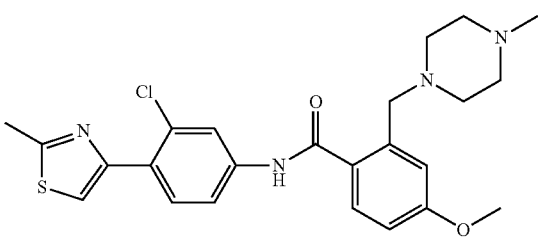
example 34
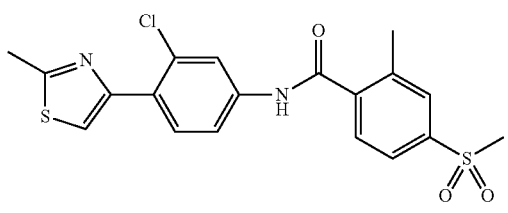
example 35
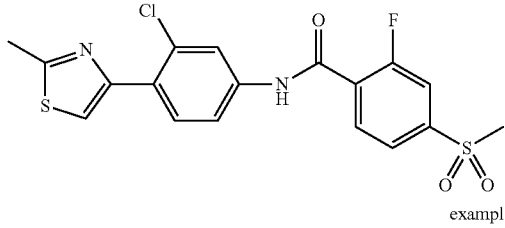
example 36
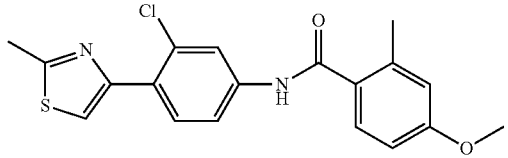
example 37
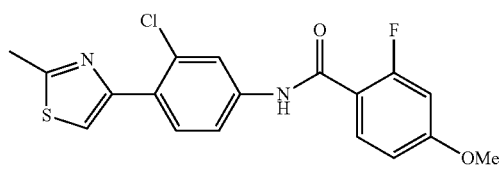
example 38
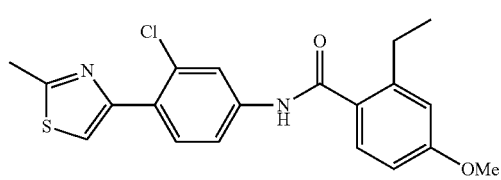
example 39
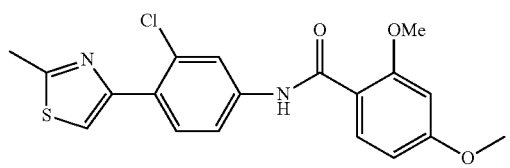
Intermediate 5:
4-(2-(trifluoromethyl)thiazol-4-yl)aniline
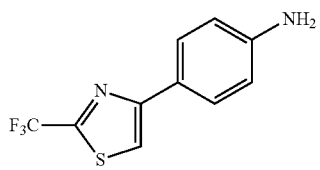 [SMILES: Nc1ccc(-c2csc(C(F)(F)F)n2)cc1]
The compound is made according to the following scheme using 2,2,2-trifluoroethanethioamide.
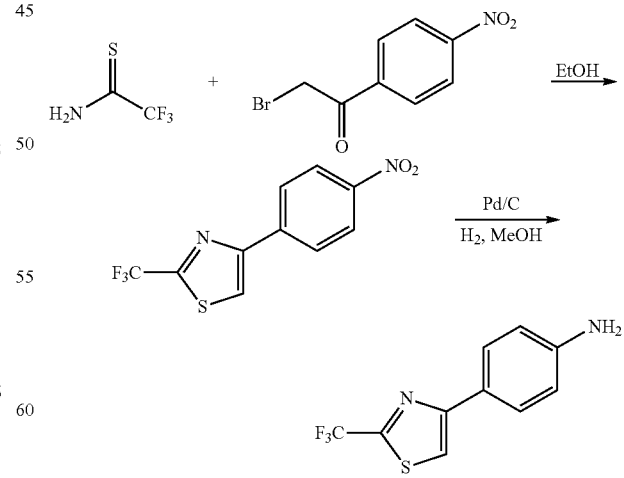
The following examples are synthesized using intermediate 5 coupled with the appropriate carboxylic acid using method A or B.

example 40
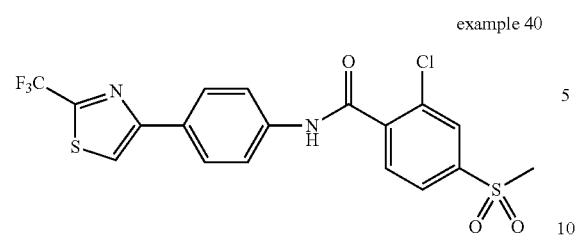
example 41
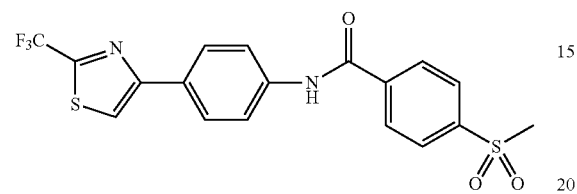
example 42
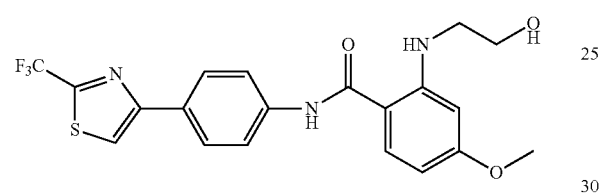
example 43
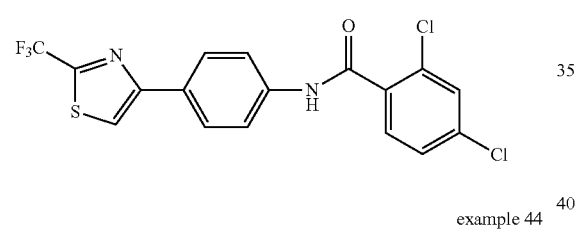
example 44
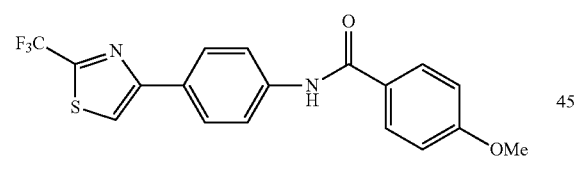
example 45
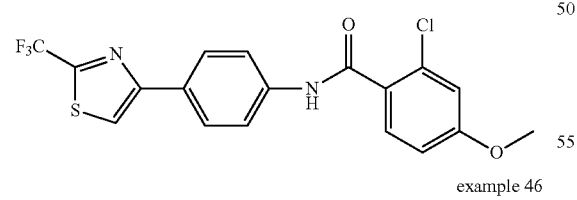
example 46
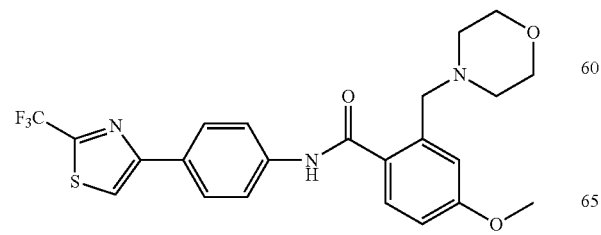
example 47
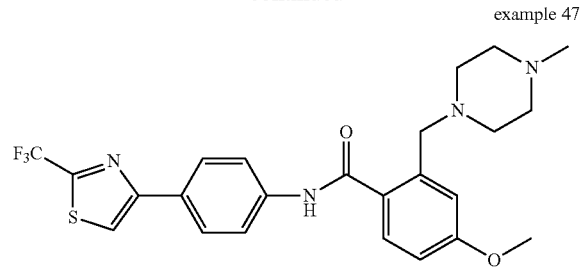
example 48
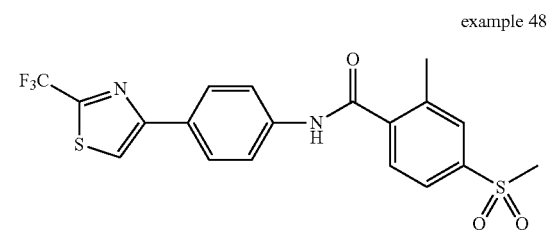
example 49
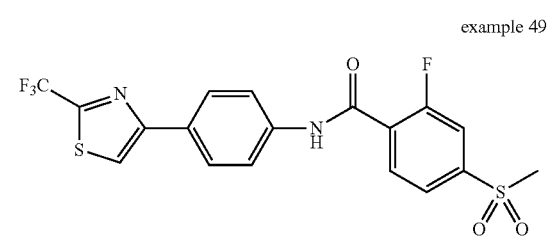
example 50
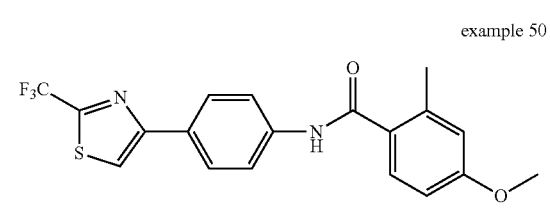
example 51
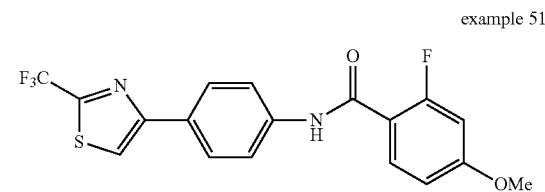
example 52
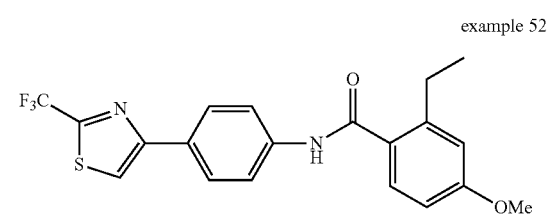
example 53
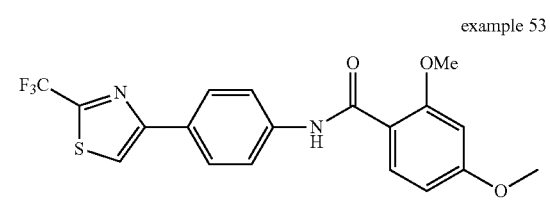

Intermediate 6: 3-chloro-4-(2-(trifluoromethyl)thiazol-4-yl)aniline

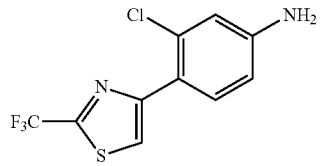 [SMILES: Nc1ccc(-c2csc(C(F)(F)F)n2)c(Cl)c1]

The compound is made according to the following scheme using 2,2,2-trifluoroethanethioamide (see intermediate 1).

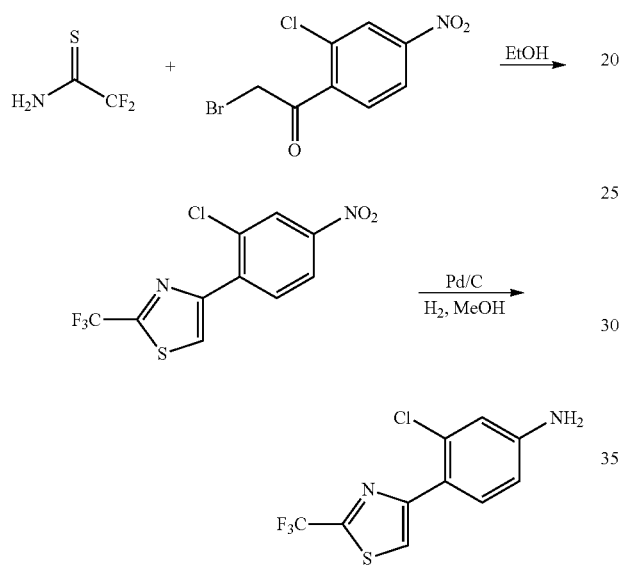

The following examples are synthesized using intermediate 6 coupled with the appropriate carboxylic acid using method A or B.

example 54 example 55

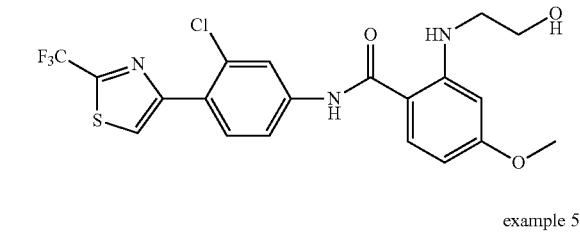

example 56 example 57

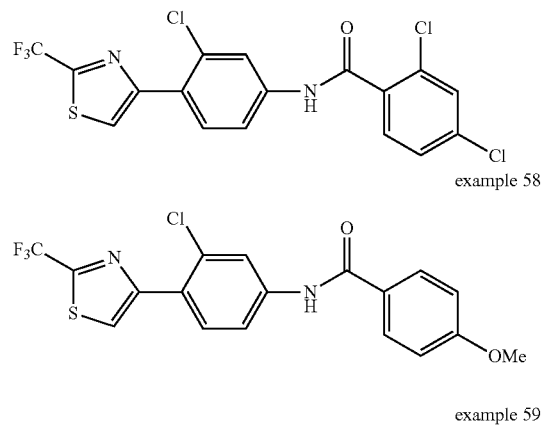

example 58 example 59

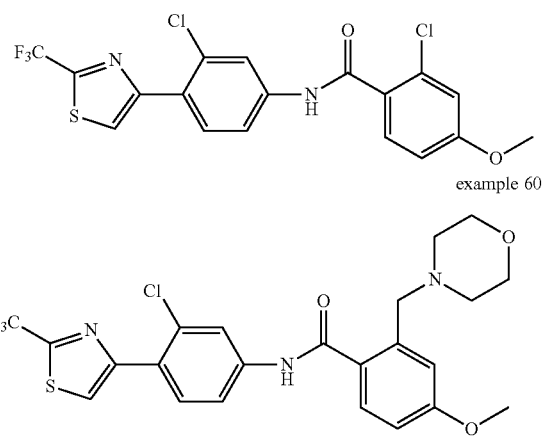

example 60 example 61 example 62

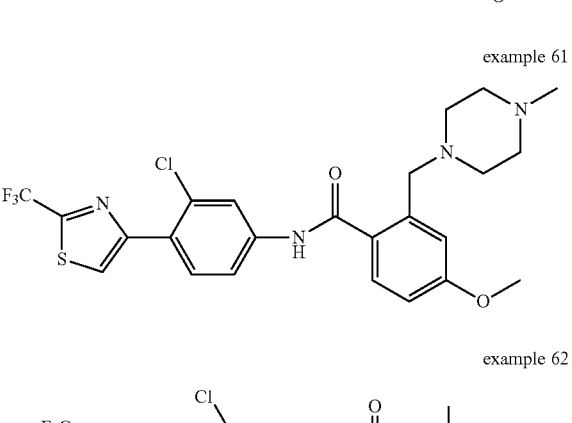

example 63
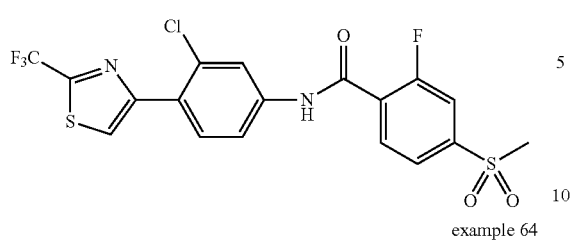
example 64
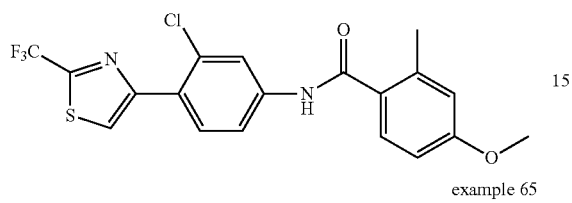
example 65
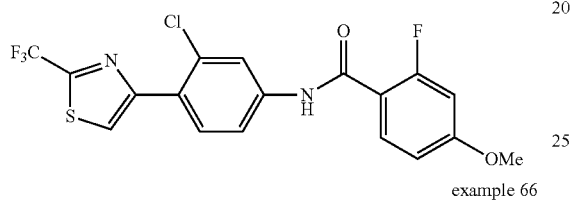
example 66
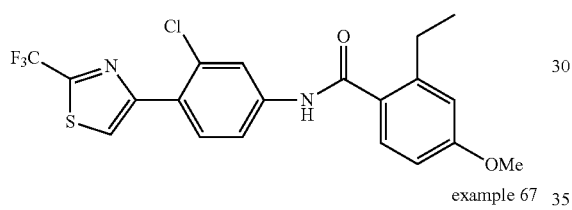
example 67
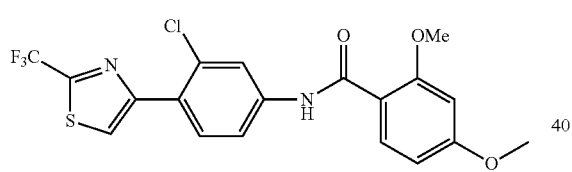
Intermediate 7: 4-(2-ethylthiazol-4-yl)aniline
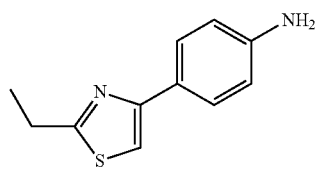
The compound is made according to the following scheme using propanethioamide
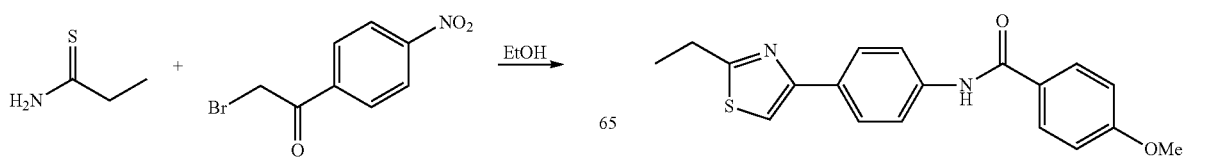
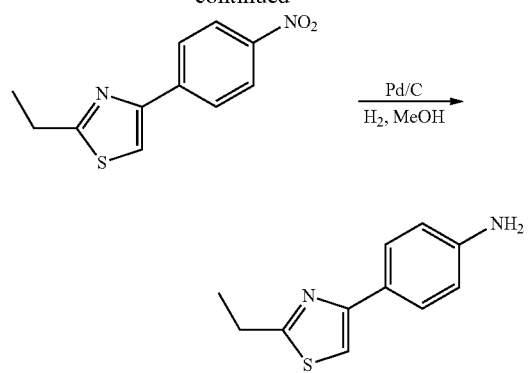
The following examples are synthesized using intermediate 7 coupled with the appropriate carboxylic acid using method A or B:
example 68
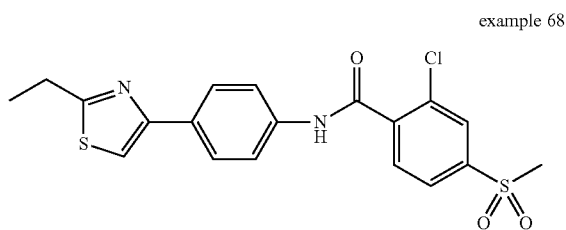
example 69
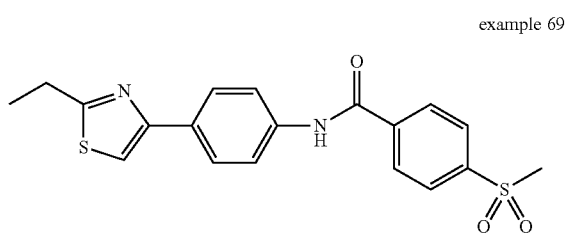
example 70
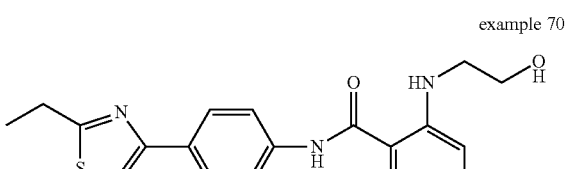
example 71
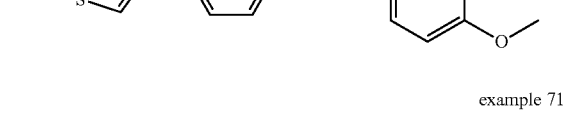
example 72
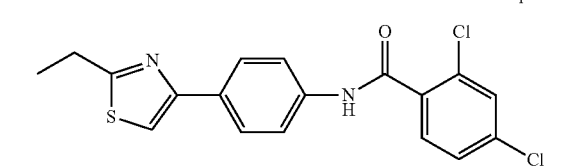

example 73
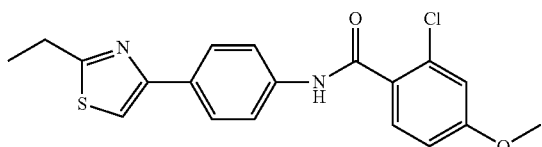
example 74
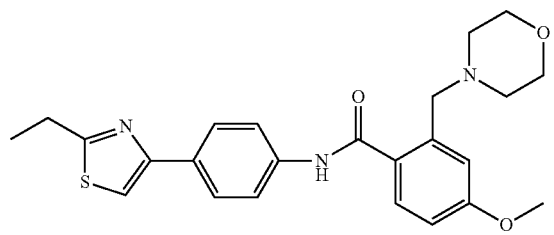
example 75
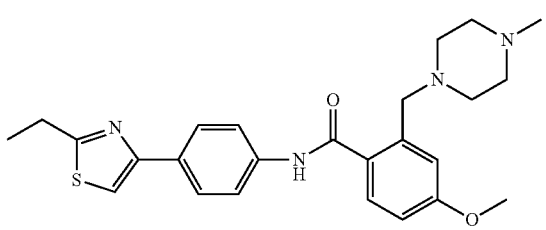
example 76
example 77
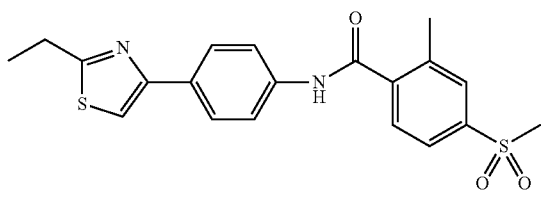
example 78
example 79
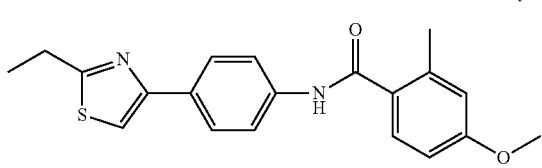
example 80
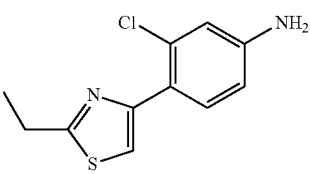
example 81
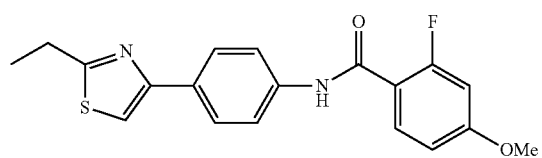
Intermediate 8:
3-chloro-4-(2-ethylthiazol-4-yl)aniline
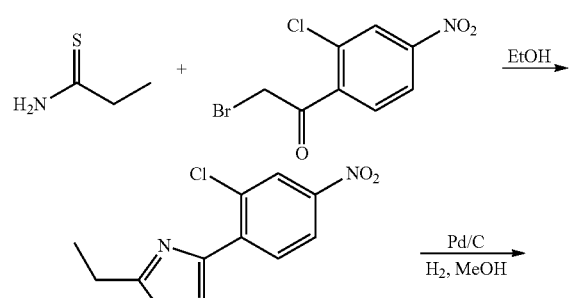
The compound is made according to the following scheme using propanethioamide (see intermediate 1).
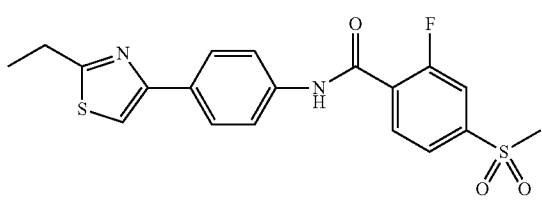
The following examples are synthesized using intermediate 8 coupled with the appropriate carboxylic acid using method A or B.
example 82
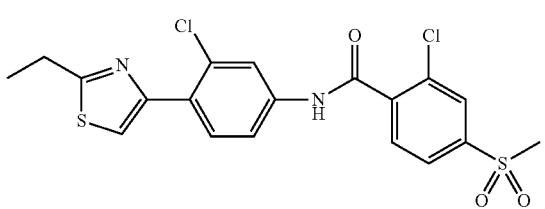

example 83
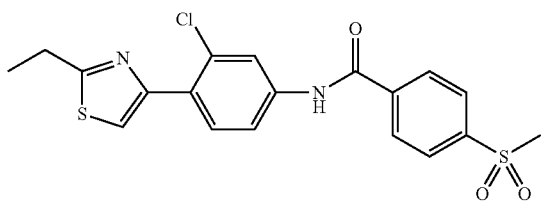
example 84
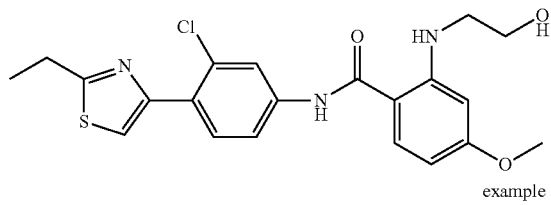
example 85
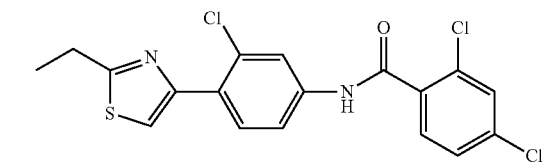
example 86
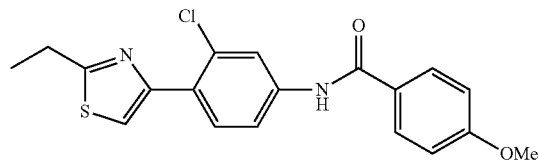
example 87
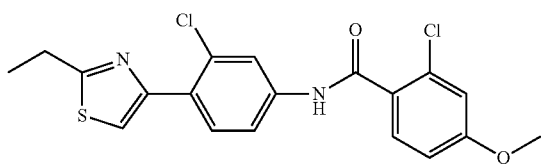
example 88
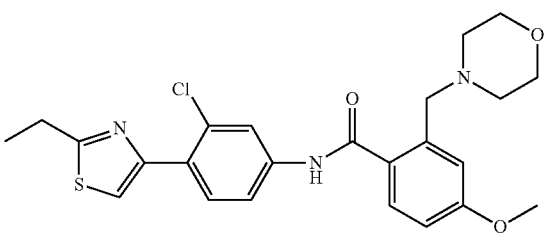
example 89
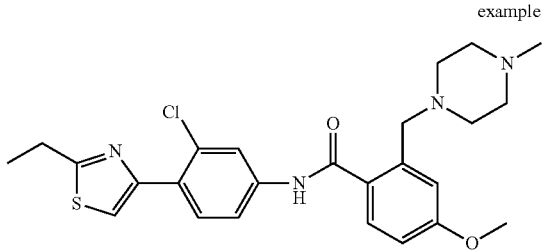
example 90
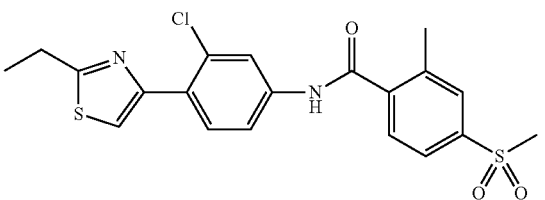
example 91
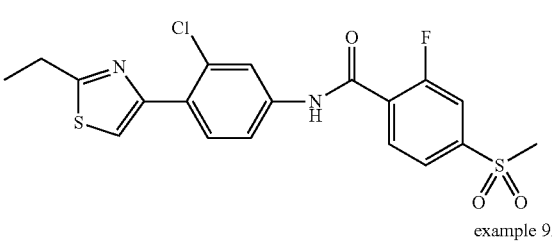
example 92
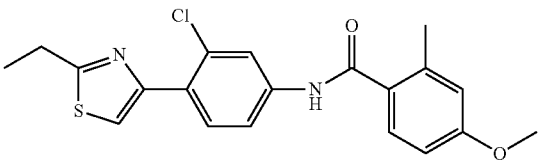
example 93
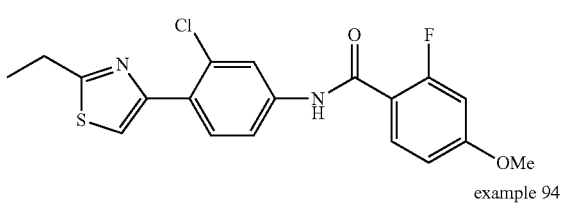
example 94
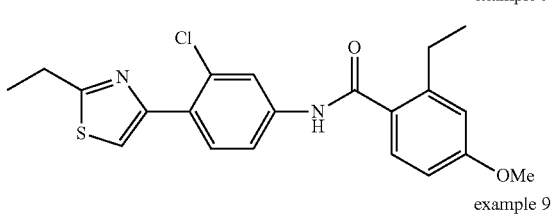
example 95
Intermediate 9: 4-(2-isopropylthiazol-4-yl)aniline
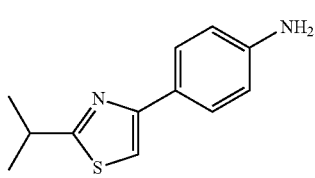
The compound is made according to the following scheme using 2-methylpropanethioamide.

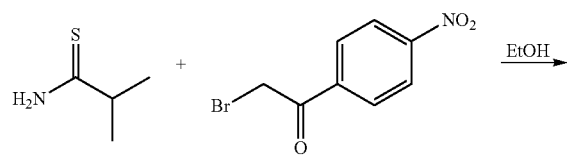
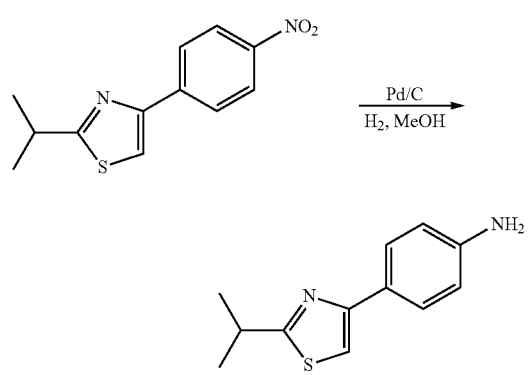
The following examples are synthesized using intermediate 9 coupled with the appropriate carboxylic acid using method A or B.
example 96
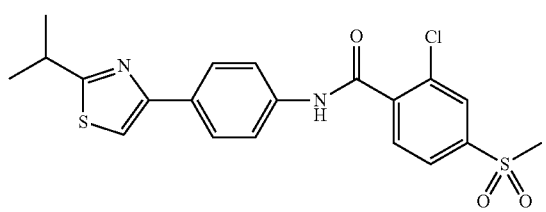
example 97
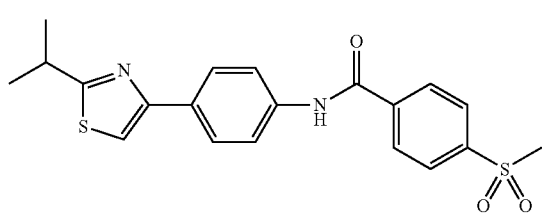
example 98
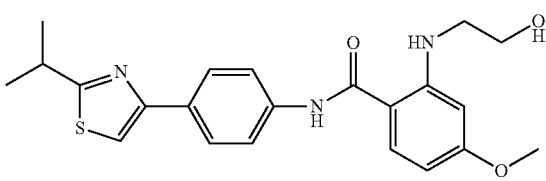
example 99
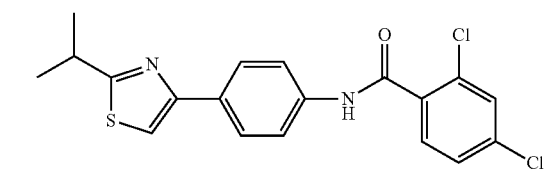
-continued
example 100
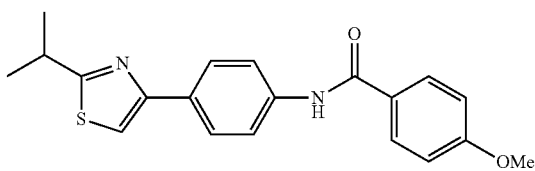
example 101
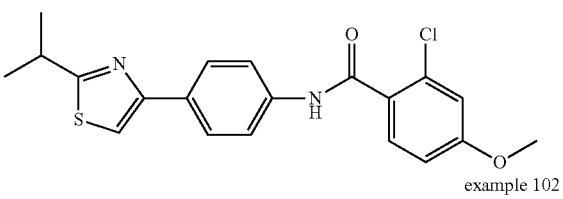
example 102
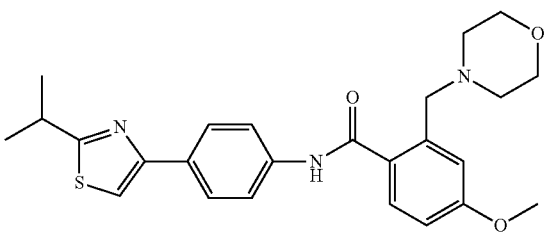
example 103
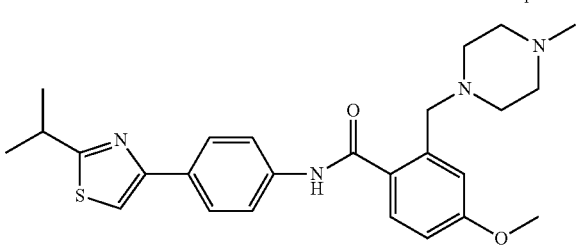
example 104
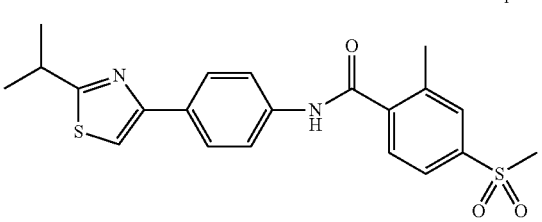
example 105
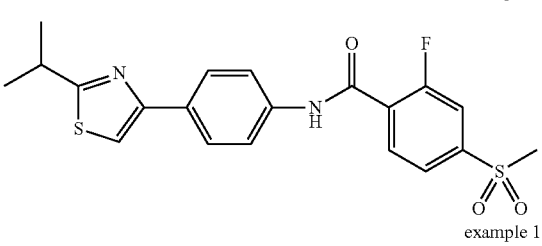
example 106 example 107
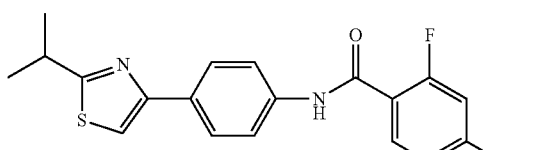

example 108
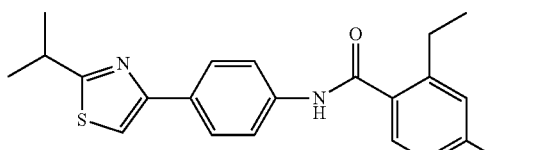

example 109
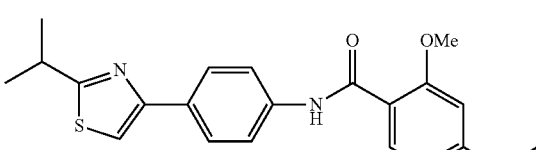

Intermediate 10:
3-chloro-4-(2-isopropylthiazol-4-yl)aniline

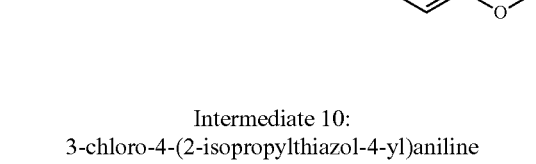

The compound is made according to the following scheme using 2-methylpropanethioamide (see intermediate 1).

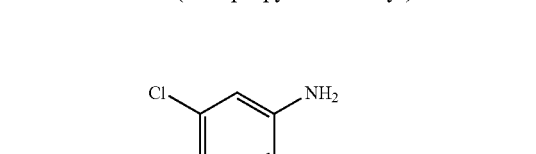

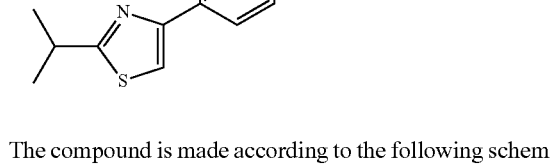

The following examples are synthesized using intermediate 10 coupled with the appropriate carboxylic acid using method A or B.

example 110
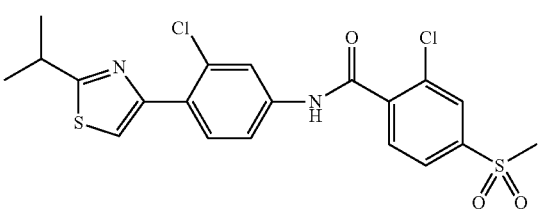

example 111
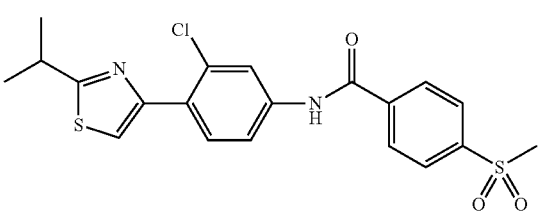

example 112
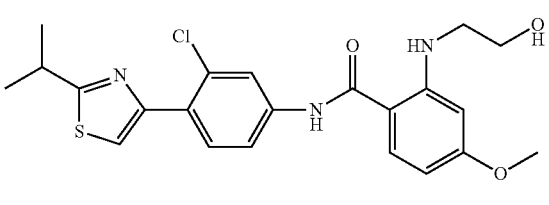

example 113
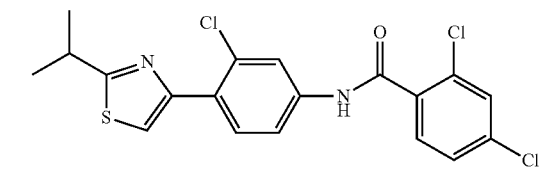

example 114
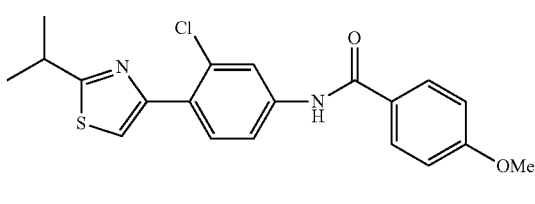

example 115
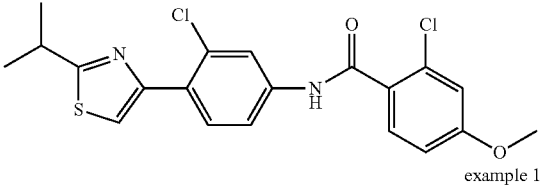

example 116
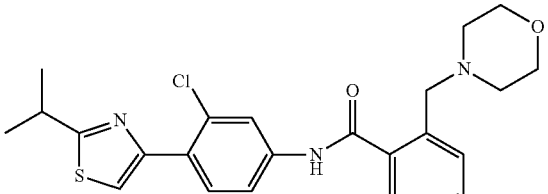

example 117
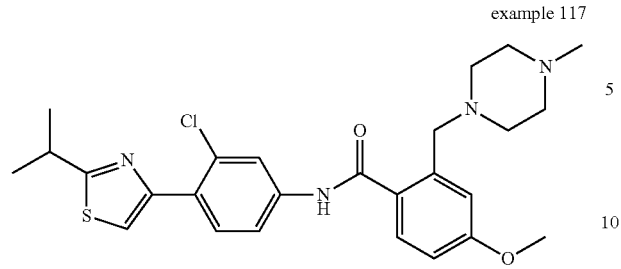
example 118
example 119
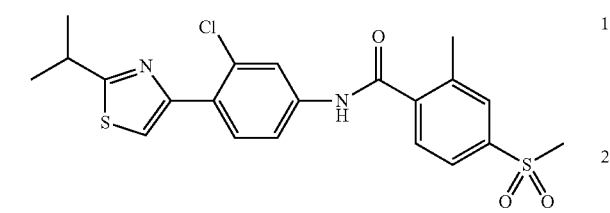
example 120
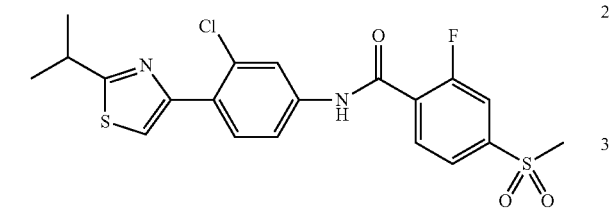
example 121
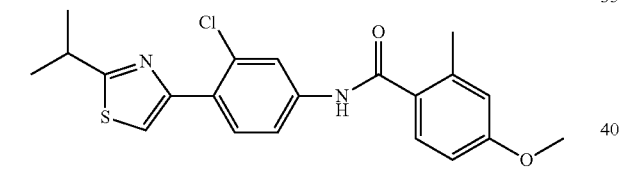
example 122
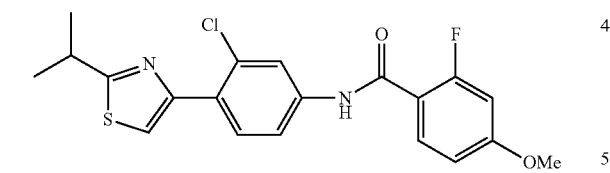
example 1023
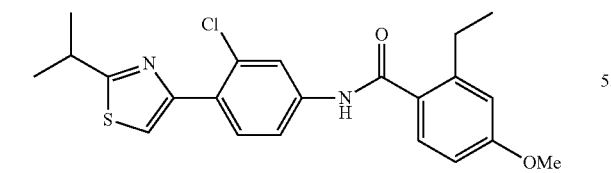
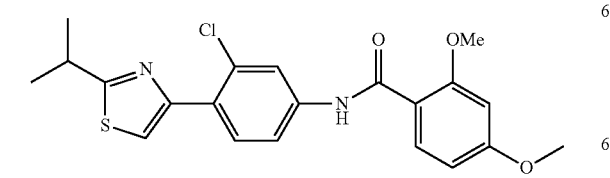
Intermediate 11: 4-(2-cyclopropylthiazol-4-yl)aniline
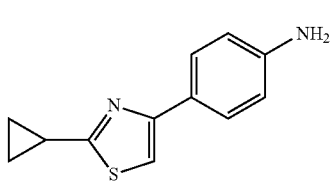 [SMILES: Nc1ccc(-c2csc(C3CC3)n2)cc1]
The compound is made according to the following scheme using cyclopropanecarbothioamide.
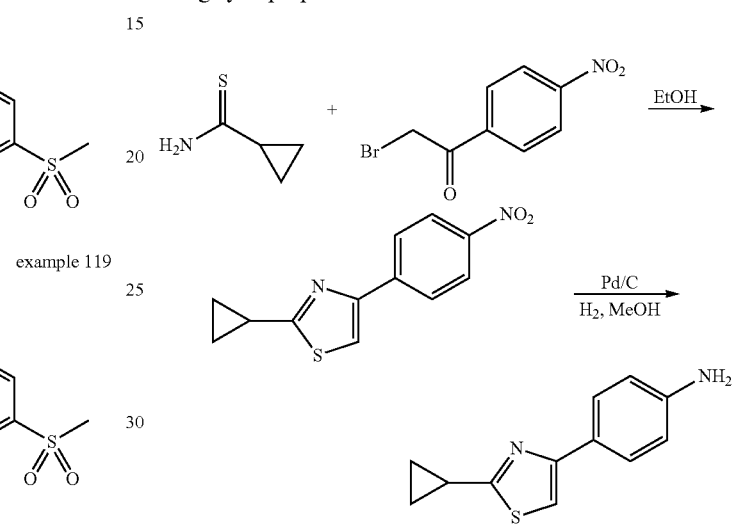
The following examples are synthesized using intermediate 11 coupled with the appropriate carboxylic acid using method A or B.
example 124
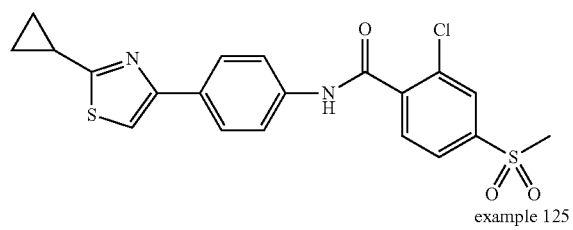
example 125
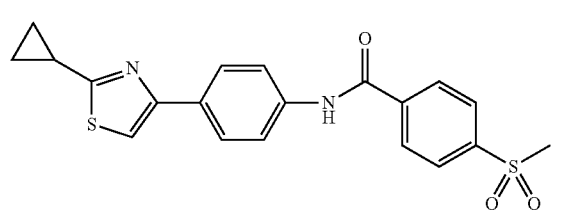
example 126
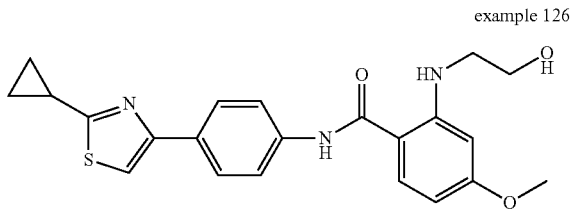

example 127
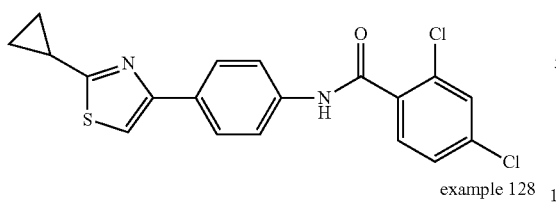
example 128
example 129
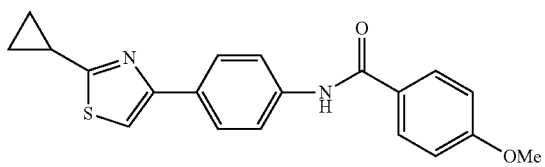
example 130
example 131
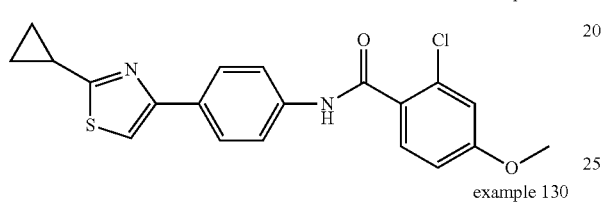
example 132
example 133
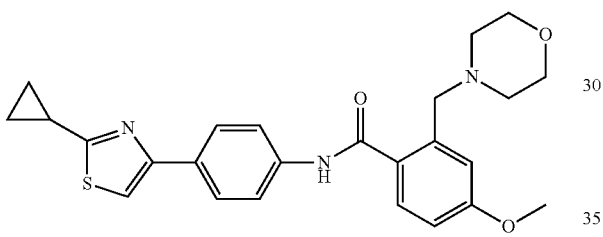
example 134
example 135
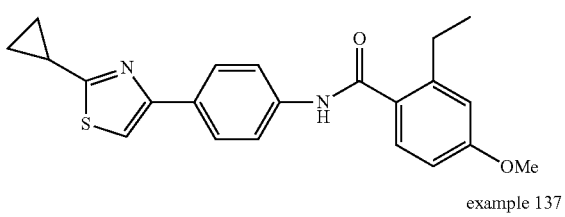
example 136
example 137
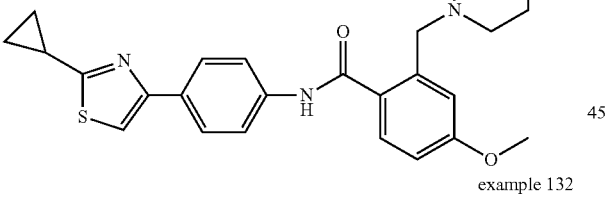
Intermediate 12:
3-chloro-4-(2-cyclopropylthiazol-4-yl)aniline
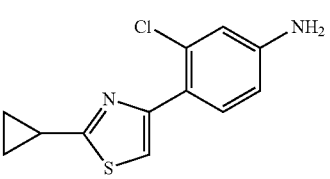 [SMILES: Nc1ccc(-c2csc(C3CC3)n2)c(Cl)c1]
The compound is made according to the following scheme using cyclopropanecarbothioamide (see intermediate 1).
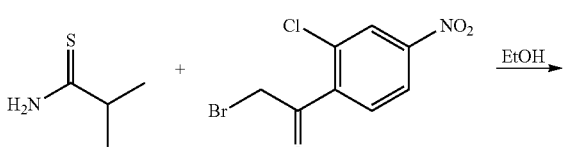
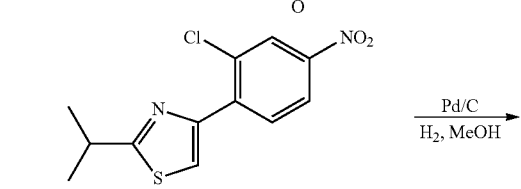
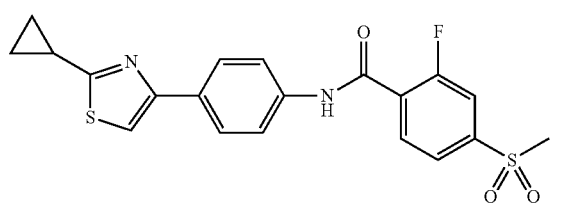

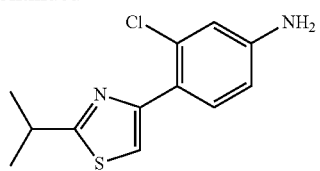
The following examples are synthesized using intermediate 12 coupled with the appropriate carboxylic acid using method A or B.
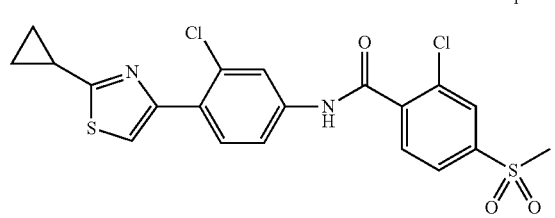
example 138
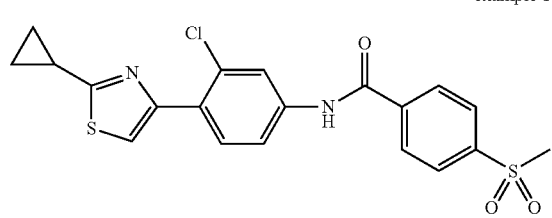
example 139
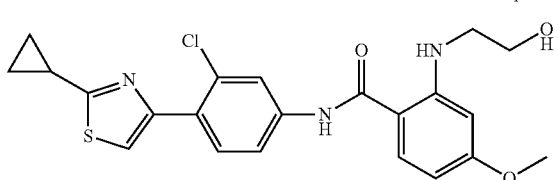
example 140
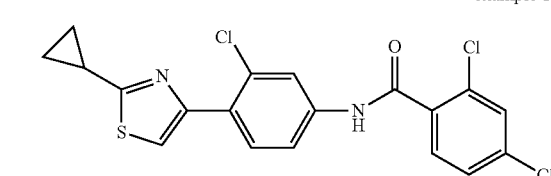
example 141
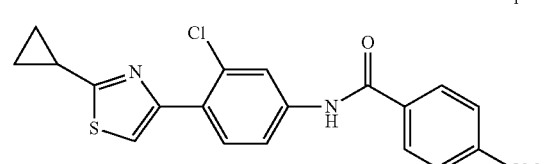
example 142
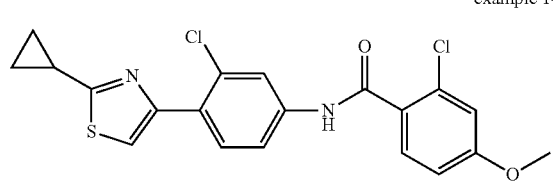
example 143
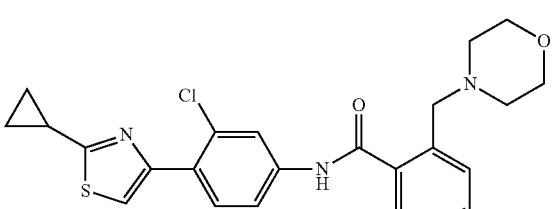
example 144
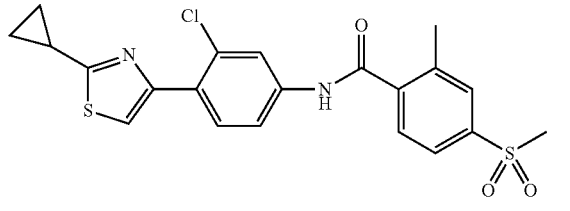
example 145
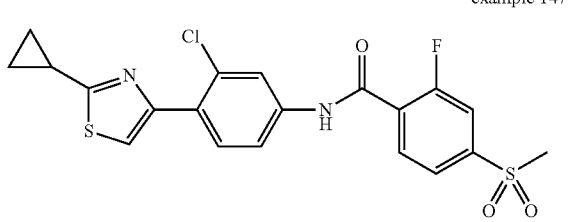
example 146
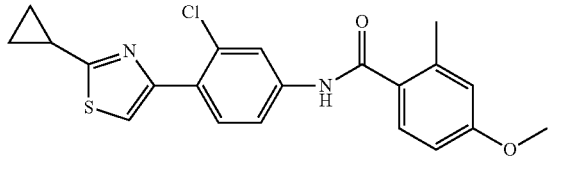
example 147
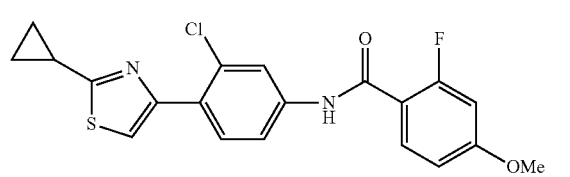
example 148
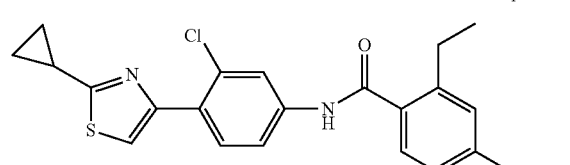
example 149
example 150 example 151
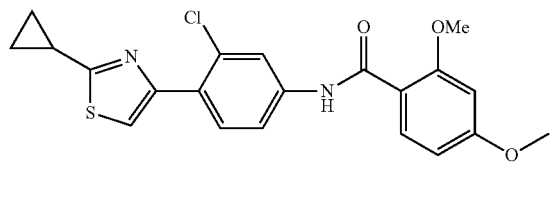
Intermediate 13: 4-(2-phenylthiazol-4-yl)aniline
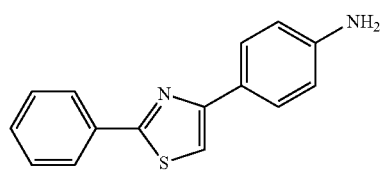 [SMILES: Nc1ccc(-c2csc(-c3ccccc3)n2)cc1]
The compound is made according to the following scheme using phenylcarbothioamide.
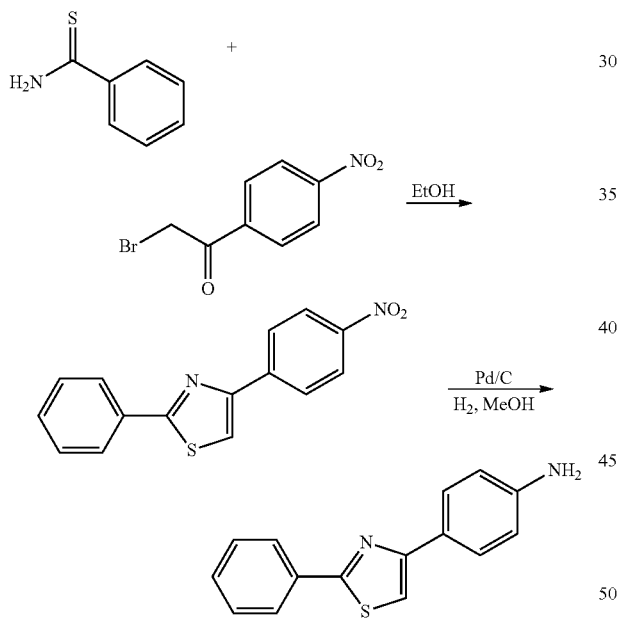
The following examples are synthesized using intermediate 13 coupled with the appropriate carboxylic acid using method A or B.
example 152
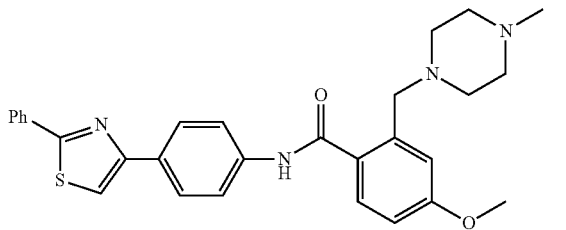
example 153
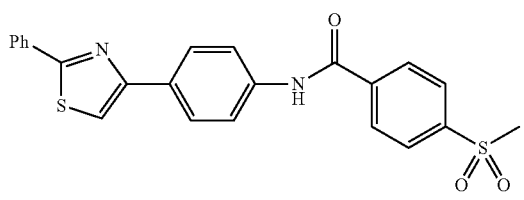
example 154
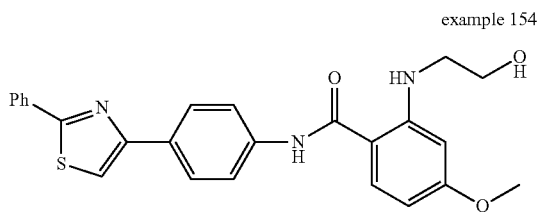
example 155
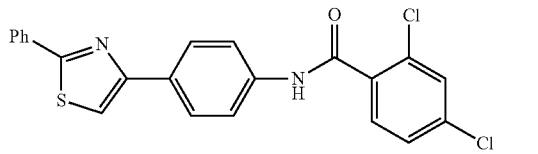
example 156
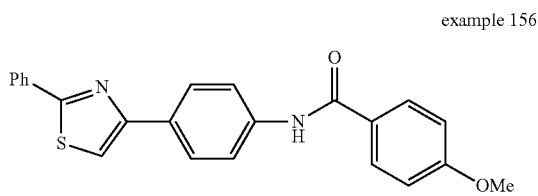
example 157
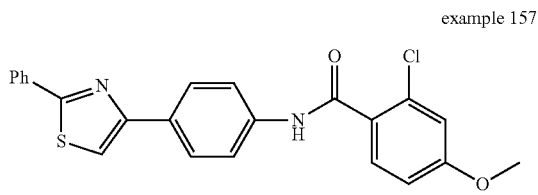
example 158
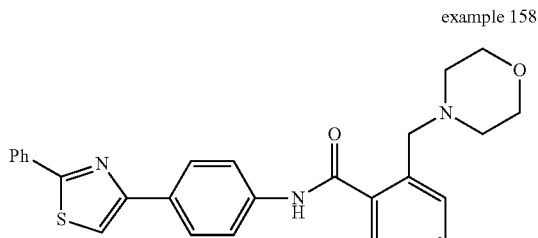
example 159

103
-continued
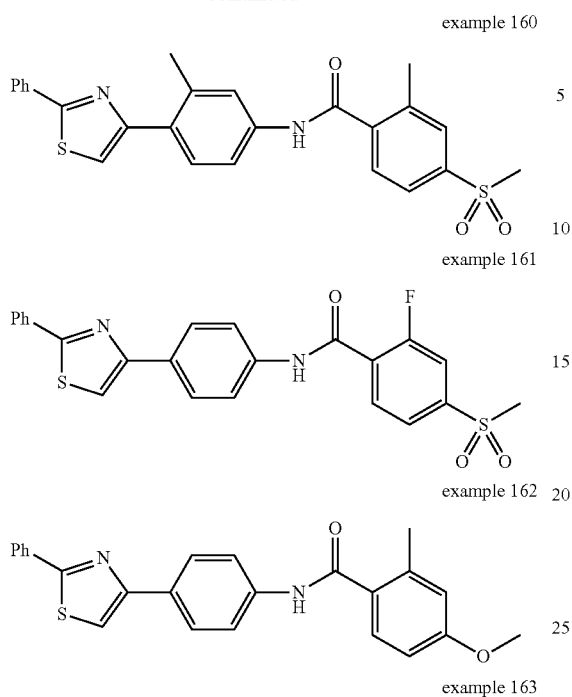
Intermediate 14:
3-chloro-4-(2-phenylthiazol-4-yl)aniline
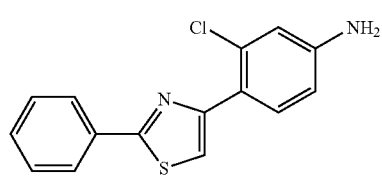 [SMILES: Nc1ccc(-c2csc(-c3ccccc3)n2)c(Cl)c1]
The compound is made according to the following scheme using phenylcarbothioamide (see intermediate 1).
104
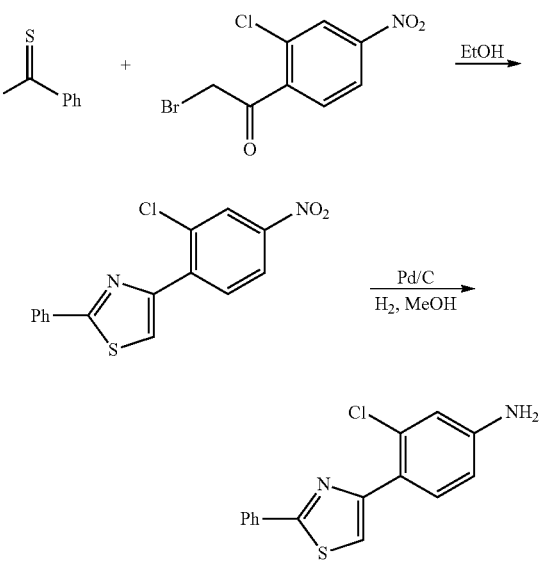
The following examples are synthesized using intermediate 14 coupled with the appropriate carboxylic acid using method A or B.
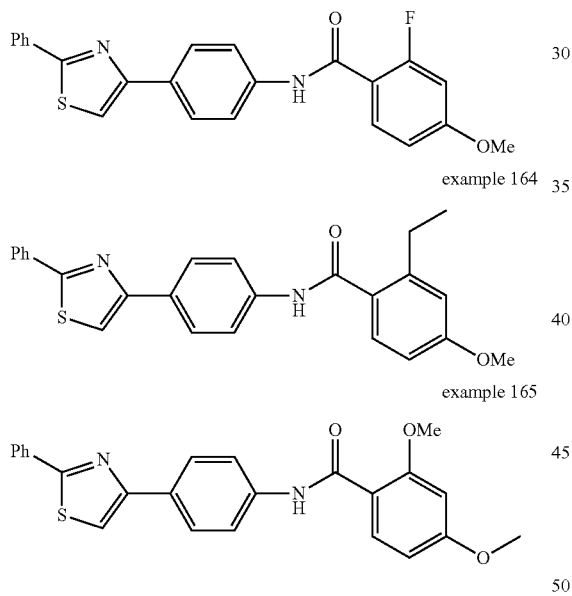

example 170
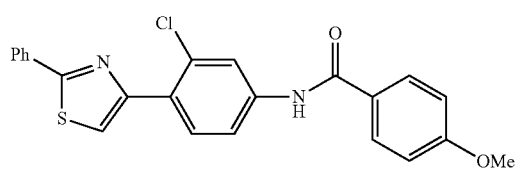
example 171
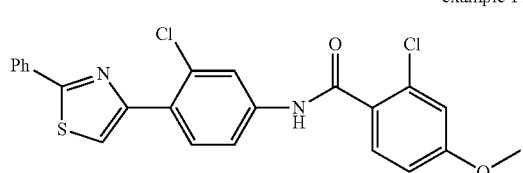
example 172
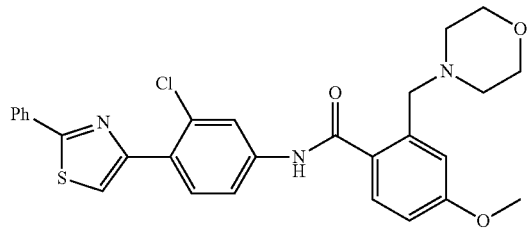
example 173
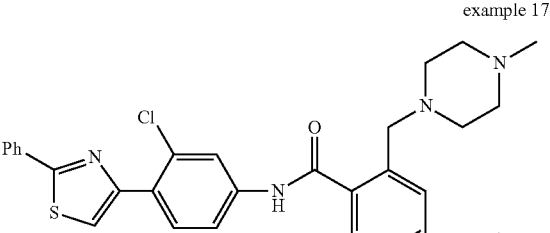
example 174
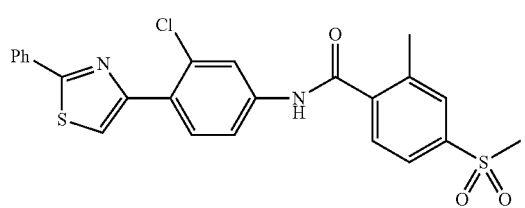
example 175
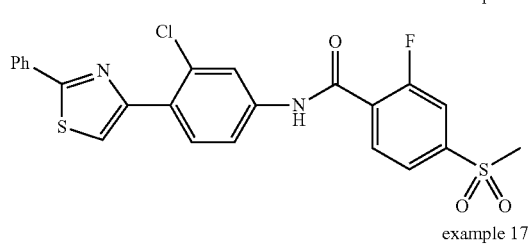
example 176
example 177
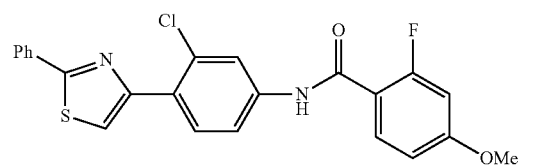
example 178
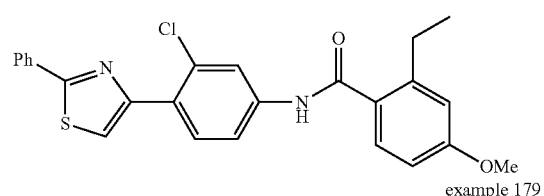
example 179
The examples 180 and 182 are prepared according to the following scheme.
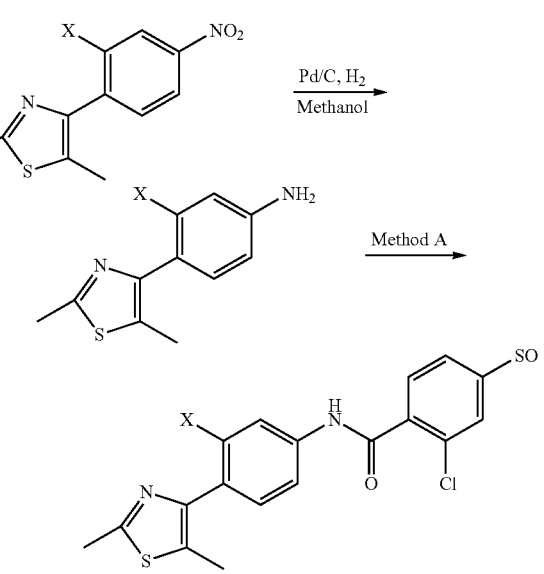
X = H Example
X = Cl Example
*Journal of Pharmaceutical Sciences* (1969), 58(7), 852-7
The examples 181 and 184 are prepared according to the following scheme.

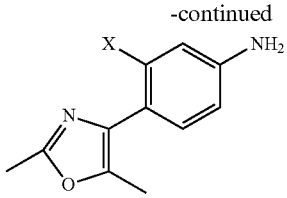

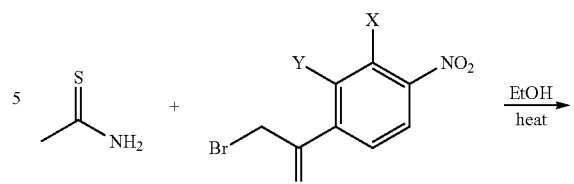

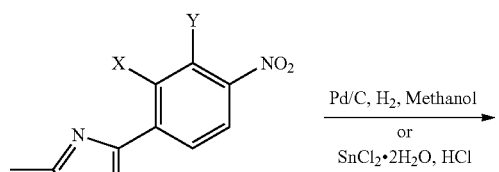

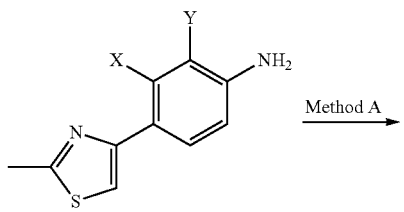

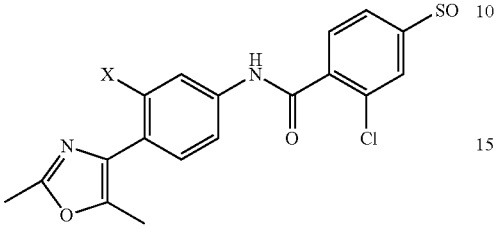

X = H Example 1
X = Cl Example 1

*Journal of Heterocyclic Chemistry* (1989), 26(2), 269-75

The Example 183 is prepared according to the following scheme.

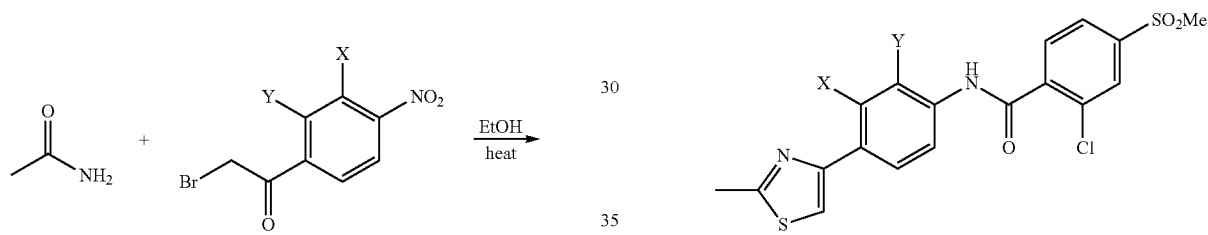

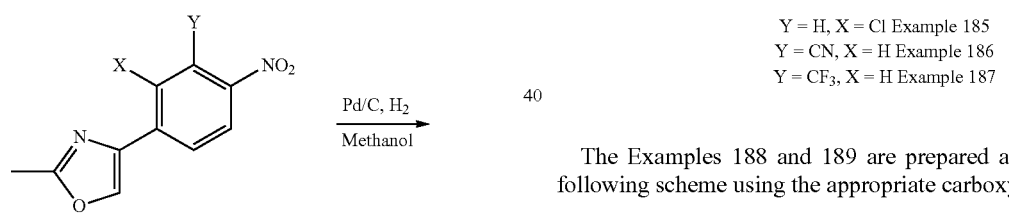

Y = H, X = Cl Example 183

The Examples 185-187 are prepared according to the following scheme.

Y = H, X = Cl Example 185
Y = CN, X = H Example 186
Y = CF3, X = H Example 187

The Examples 188 and 189 are prepared according the following scheme using the appropriate carboxylic acid.

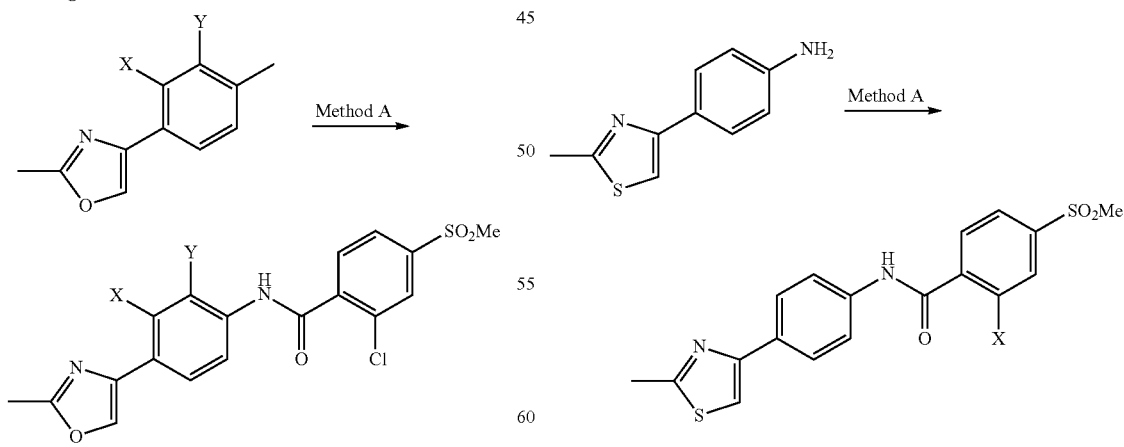

X = CN Example 188
X = CF3 Example 189

The Example 190-193 are prepared according to the following scheme using the appropriate carboxylic acid.

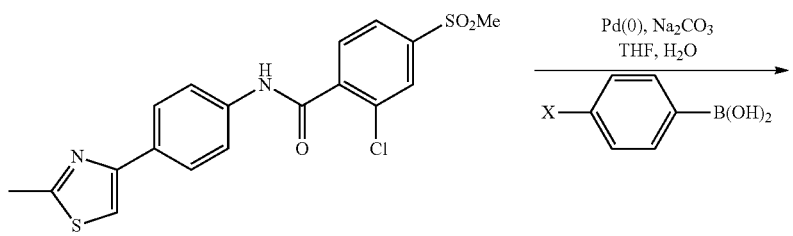

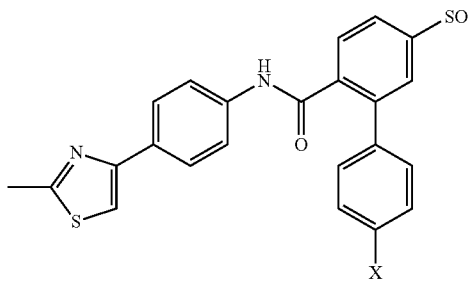

X = H Example 190
X = CF3 Example 191
X = F Example 192
X = OMe Example 193

II. Biological Evaluation

The ability of compounds described in the current invention to inhibit hedgehog pathway signaling was determined from the following cell differentiation assays (Method A, or Modified Method A as described below) in which cellular alkaline phosphatase activity is assessed in the presence of control vehicle or test compound, as previously described in the literature (Wu et al., Chemistry & Biology, 11: 1229-1238, 2004; Couve-Privat, et al., Cancer Research, 64; 3559-3565, 2004; Dwyer et al., J. Biological Chemistry, 282: 8959-8968, 2007) with modifications as described below.

Figure 2:
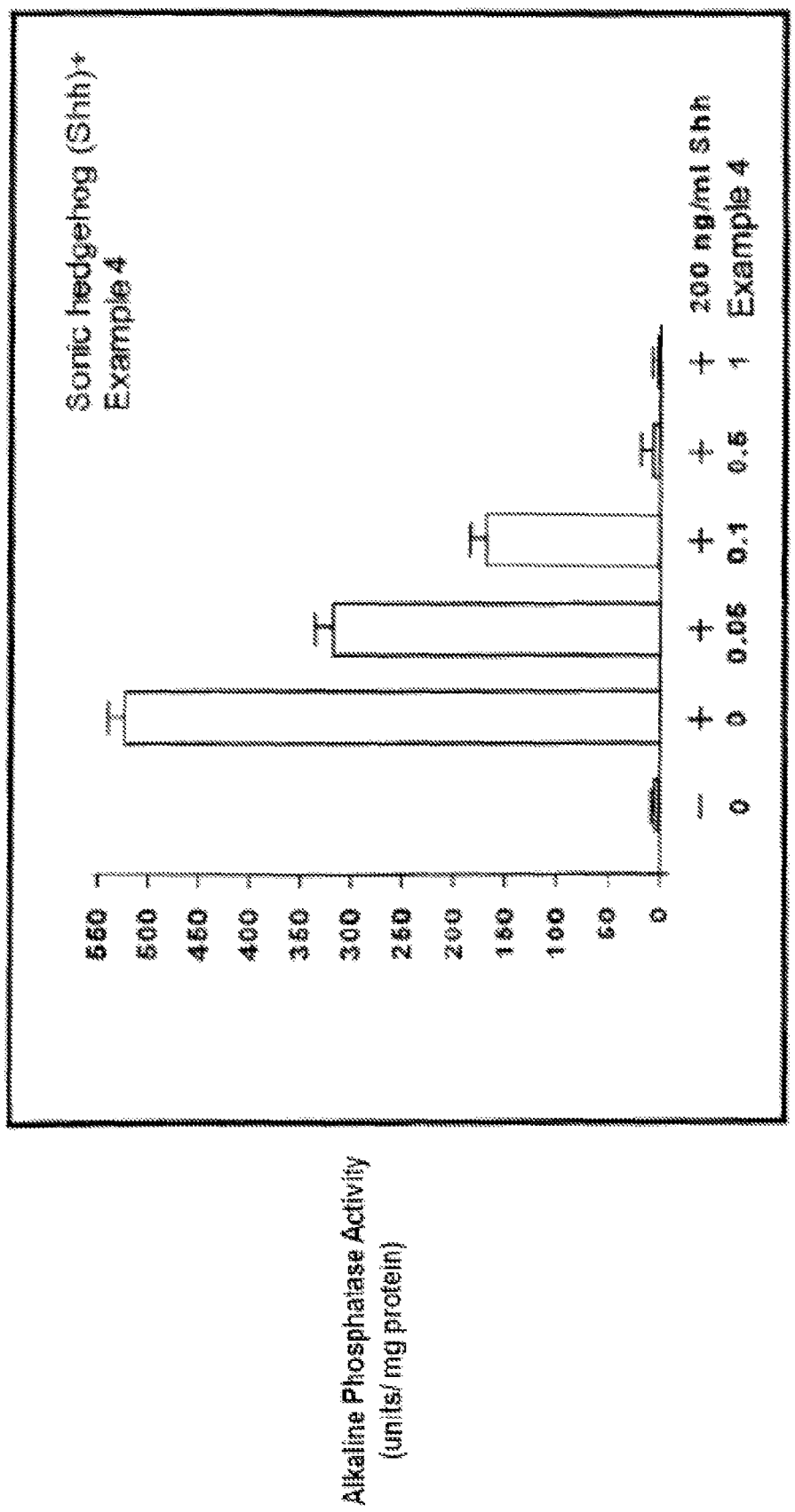
FIG. 2 shows the dose-response of the compound of Example 4 in the alkaline phosphatase assay described herein.

Method A: Mouse $C_3H_{10}T1/2$ (CCL-226™) or M2-10B4 (CRL-1972™) cells obtained from the American Type Tissue Culture Collection (Maryland, USA) were cultured to 60-80% confluence in Dulbecco's modified Eagle's Medium ($C_3H_{10}T1/2$ cells) containing heat-inactivated 10% fetal bovine serum or RPMI-1640 media (M2-10B4 cells) containing heat-inactivated 10% fetal bovine serum. Cell cultures were maintained in 10 U/mL penicillin, 100 µg/mL streptomycin and 2 mM glutamine. Cells were then trypsinized, counted and plated into 96-well microtiter plates prior to incubation overnight at 37° C. in 5% CO2. The following morning, control vehicle (DMSO) or compound dissolved in 100% DMSO were serially added to individual wells, 30 minutes prior to the addition of Control Buffer or Recombinant Mouse Sonic Hedgehog (Shh-N, CF, 461-5H-025/CF, R&D Systems, Minnesota, USA) to final concentration of 2 µg/mL. The 96-well microtiter plates were then incubated at 37° C. in 5% CO2 for 72 hours before being assayed for alkaline phosphatase activity using p-nitrophenyl phosphate (pNPP, Anaspec, Calif., USA). Briefly, after 72 hours incubation, cell culture media was carefully aspirated from the wells of the 96-well microtiter plates and cells gently washed with phosphate-buffered saline, pH 7.4 (PBS). Following removal of PBS, cells were lysed in 50 µL RIPA lysis buffer and alkaline phosphatase activity assayed following addition of 50 µL pNPP reaction mixture for 30 minutes during which reagents were mixed by gently shaking of the plates. Absorbance was subsequently measured at 405 nm, and the concentration of test compound required to cause 50% inhibition of sonic hedgehog stimulated alkaline phosphatase activity ($IC_{50}$) calculated from the dose-response curve. Similarly, an $IC_{90}$ was determined. At least triplicate determinations for each individual test compound concentration were made and data plotted as mean+standard deviation relative to the DMSO control vehicle. FIG. 1 shows the dose-response of cyclopamine, a positive control, in the assay described above. FIG. 2 shows the dose-response of the compound of Example 4 in the assay described above. The compound of Example 4 was found to have an $IC_{50}$ of 63 nM and an $IC_{90}$ of 300 nM.

Modified Method A: An additional method to assess inhibition of hedgehog pathway signaling was also applied in which 100 nM of the smoothened agonist, purmorphamine (Stemgent, Calif.) was added to confluent C3H10T1/2 cells instead of recombinant sonic hedgehog protein and 72 hours after co-incubation with compounds alkaline phosphatase activity was assayed using the alkaline phosphatase assay kit from BioAssay Systems (Haywood, Calif.).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

We claim:

1. A compound having the structure of Formula (I):

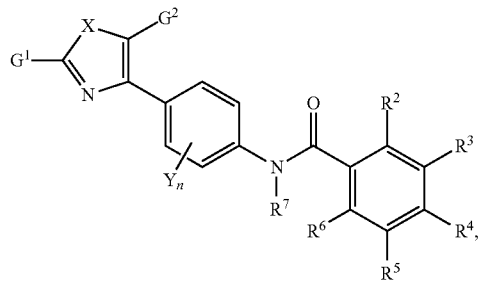

or a stereoisomer, hydrate, solvate or pharmaceutically acceptable salt thereof, wherein:
X is S;
Y is halogen;
n is 0, or 1;
$G^1$ is $C_1$-$C_6$ alkyl;
$G^2$ is hydrogen;
$R^2$ is selected from halogen, —CN, alkyl, —$CF_3$ or —$CH_2$—(N-linked heterocycle);
$R^4$ is selected from alkoxy, or —$SO_2$-alkyl,
$R^3$, $R^5$ and $R^6$ are each hydrogen; and
$R^7$ is H.

2. The compound of claim 1, or a stereoisomer, tautomer, hydrate, solvate or pharmaceutically acceptable salt thereof, wherein n is 0.

3. The compound of claim 1, or a stereoisomer, tautomer, hydrate, solvate or pharmaceutically acceptable salt thereof, wherein n is 1.

4. The compound of claim 1, or a stereoisomer, tautomer, hydrate, solvate or pharmaceutically acceptable salt thereof, wherein $R^2$ is halogen.

5. The compound of claim 1, or a stereoisomer, tautomer, hydrate, solvate or pharmaceutically acceptable salt thereof, wherein $R^2$ is —CN, -alkyl, or —$CF_3$.

6. The compound of claim 1, or a stereoisomer, tautomer, hydrate, solvate or pharmaceutically acceptable salt thereof, wherein $R^2$ is —$CH_2$—(N-linked heterocycle).

7. The compound of claim 6, or a stereoisomer, tautomer, hydrate, solvate or pharmaceutically acceptable salt thereof, wherein the N-linked heterocycle is morpholinyl or piperazinyl.

8. The compound of claim 1, or a stereoisomer, tautomer, hydrate, solvate or pharmaceutically acceptable salt thereof, wherein $R^4$ is —$SO_2$Me or —OMe.

9. The compound of claim 1, or a stereoisomer, tautomer, hydrate, solvate or pharmaceutically acceptable salt thereof, wherein $R^2$ is halogen and $R^4$ is —$SO_2$Me.

10. The compound of claim 1, or a stereoisomer, tautomer, hydrate, solvate or pharmaceutically acceptable salt thereof, wherein $R^2$ is halogen and $R^4$ is —OMe.

11. The compound of claim 1, or a stereoisomer, tautomer, hydrate, solvate or pharmaceutically acceptable salt thereof, wherein n is 0; $G^2$ is H; $G^1$ is alkyl; X is —S—; $R^2$ is halogen and $R^4$ is —OMe.

12. The compound of claim 1, or a stereoisomer, tautomer, hydrate, solvate or pharmaceutically acceptable salt thereof, wherein n is 0; $G^2$ is H; $G^1$ is alkyl; X is —S—; $R^2$ is halogen and $R^4$ is —$SO_2$Me.

13. The compound of claim 1, or a hydrate, solvate or pharmaceutically acceptable salt thereof, represented by the structure:

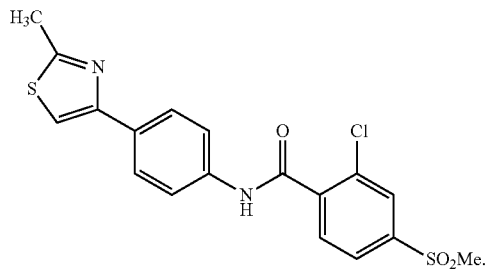 [SMILES: Cc1nc(-c2ccc(NC(=O)c3ccc(S(C)(=O)=O)cc3Cl)cc2)cs1]

14. A compound, or a hydrate, solvate or pharmaceutically acceptable salt thereof, represented by the structure:

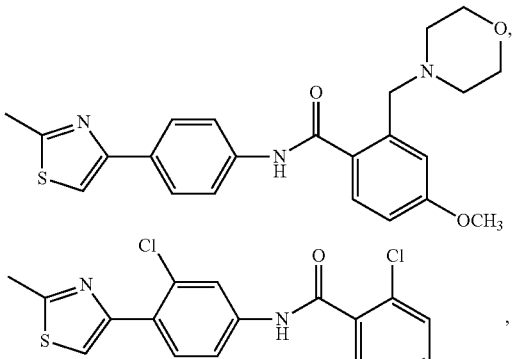

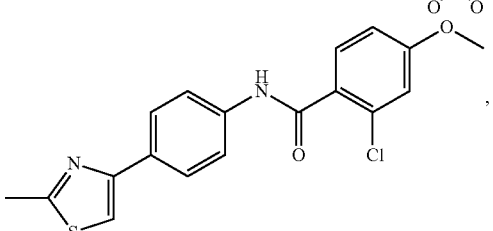

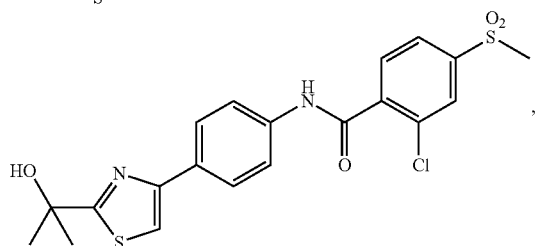

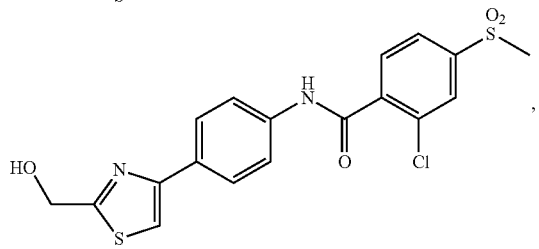

-continued

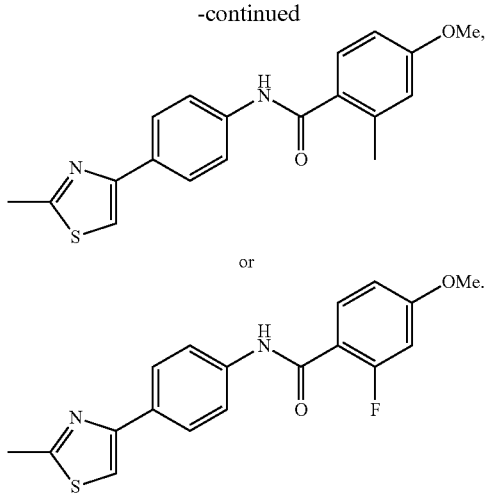

15. A pharmaceutical composition comprising a compound of Formula (I) as described in claim 1, or a stereoisomer, hydrate, solvate or pharmaceutically acceptable salt thereof, and at least one pharmaceutically acceptable excipient.

16. A pharmaceutical composition comprising the compound as described in claim 13, or a hydrate, solvate or pharmaceutically acceptable salt thereof, and at least one pharmaceutically acceptable excipient.

17. A pharmaceutical composition comprising a compound as described in claim 14, or a hydrate, solvate or pharmaceutically acceptable salt thereof, and at least one pharmaceutically acceptable excipient.

* * * * *